US009739594B2

(12) United States Patent
Koerner et al.

(10) Patent No.: US 9,739,594 B2
(45) Date of Patent: Aug. 22, 2017

(54) ROBUST ONE-SHOT INTERFEROMETER

(71) Applicant: Universitat Stuttgart, Stuttgart (DE)

(72) Inventors: Klaus Koerner, Stuttgart (DE); Wolfgang Osten, Stuttgart (DE)

(73) Assignee: Universität Stuttgart, Stuttgart (DE)

(*) Notice: Subject to any disclaimer, the term of this patent is extended or adjusted under 35 U.S.C. 154(b) by 284 days.

(21) Appl. No.: 14/476,301

(22) Filed: Sep. 3, 2014

(65) Prior Publication Data
US 2015/0077760 A1 Mar. 19, 2015

(30) Foreign Application Priority Data

Sep. 3, 2013 (DE) .......... 10 2013 015 031
Oct. 2, 2013 (DE) .......... 10 2013 016 752

(51) Int. Cl.
*G01B 9/02* (2006.01)
*A61B 5/00* (2006.01)
*A61B 5/107* (2006.01)

(52) U.S. Cl.
CPC ........ *G01B 9/02091* (2013.01); *A61B 5/0066* (2013.01); *G01B 9/02008* (2013.01);
(Continued)

(58) Field of Classification Search
CPC ............ G01B 9/02091; G01B 9/02008; G01B 9/02027; G01B 9/0209; G01B 9/02032; A61B 5/0066; A61B 5/1079; A61B 5/0088; A61B 5/1077
See application file for complete search history.

(56) References Cited

U.S. PATENT DOCUMENTS 1,565,533 A 12/1925 Twyman
7,177,029 B2 2/2007 deGroot

FOREIGN PATENT DOCUMENTS

DE 268771 A1 6/1989
DE 19632594 A1 2/1998
(Continued)

OTHER PUBLICATIONS

Hering, Marco et al.: "Correlated speckle noise in white-light interferometry: theoretical analysis of measurement uncertainty" (Applied Optics, vol. 48, No. 3, 2009, pp. 525 to 538).
(Continued)

*Primary Examiner* — Hwa Lee
(74) *Attorney, Agent, or Firm* — Banner & Witcoff, Ltd.

(57) ABSTRACT

Disclosed are methods and an assembly for robust one-shot interferometry, in particular for optical coherence tomography according to the spatial domain approach (SD-OCT) and/or according to the light-field approach. In one embodiment, the method and the assembly may be used for measurements on material and living tissue, for distance measurement, for 2D or 3D measurement with a finely structured light source imaged onto the object in a diffraction-limited way, or with spots thereof. The assembly may comprise an interferometer having object and reference arms and a detector for electromagnetic radiation. In other embodiments, during a detection process, a plurality of spatial interferograms may be formed by making an inclined and/or curved reference wavefront interfere with an object wavefront for each measurement point. The resulting spatial interferograms may be detected in a single detector frame and may be further evaluated via a computer program.

3 Claims, 50 Drawing Sheets

(52) U.S. Cl.
CPC ....... *G01B 9/0209* (2013.01); *G01B 9/02027* (2013.01); *G01B 9/02032* (2013.01); *A61B 5/0088* (2013.01); *A61B 5/1077* (2013.01); *A61B 5/1079* (2013.01)

(56) References Cited

FOREIGN PATENT DOCUMENTS

| DE | 102006015387 A1 | 10/2007 |
|---|---|---|
| DE | 102010006239 B3 | 3/2011 |
| DE | 102010046907 A1 | 2/2012 |
| DE | 102011000213 A1 | 7/2012 |
| EP | 0929978 A1 | 7/1999 |
| WO | 2010139764 A1 | 12/2010 |

OTHER PUBLICATIONS

Hering, Marco et al.: "One-Shot Line-Profiling White Light Interferometer with Spatial Phase Shift for Measuring Rough Surfaces" (Proc. of SPIE, vol. 6188, 2006, pp. 61880E-1 to 61880E-11).

Malacara, Daniel: "Optical Shop Testing" (John Wiley & Sons, Inc., 1992, pp. 140 to 141).

Steel, W. H.: "Interferometry" (Cambridge University Press, 1967, pp. 83 to 84).

Kelsall, D.: "Optical Frequency Response Characteristics in the presence of Spherical Aberration measured by an automatically recording Interferometric Instrument" (Proc. Phys. Soc. 73, 1959, pp. 465 to 479).

Gastinger, Kay et al.: "Optical, mechanical and electro-optical design of an interferometric test station for massive parallel inspection of MEMS and MOEMS" (Proc. of SPIE, vol. 7389, 2009, pp. 73891J-1 to 73891J-12).

Emer, Wolfgang et al.: "Ultraviolet interferometry with apochromatic reflection optics" (Applied Optics, vol. 38, No. 16, 1999, pp. 3516 to 3522).

Goodman, Joseph W.: "Holography Viewed from the Perspective of the Light Field Camera" (Proc. of Fringe 2013, 7th International Workshop on Advanced Optical Imaging and Metrology, pp. 3 to 15, Wolfgang Osten (ed.), ISBN 978-3-642-36358-0, DOI 10.1007/978-3-642-36359-7, Springer, Heidelberg, New York, Dordrecht, London 2014).

Ng, Ren et al.: "Light Field Photography with a Hand-held Plenoptic Camera" (Stanford Tech Report CTSR Feb. 2005, pp. 1 to 11).

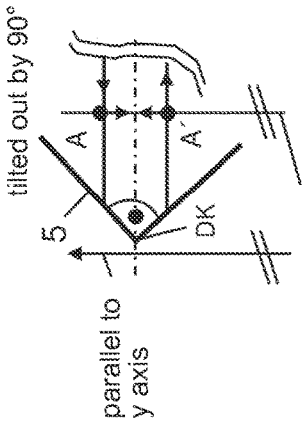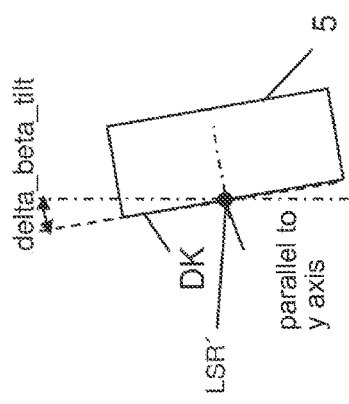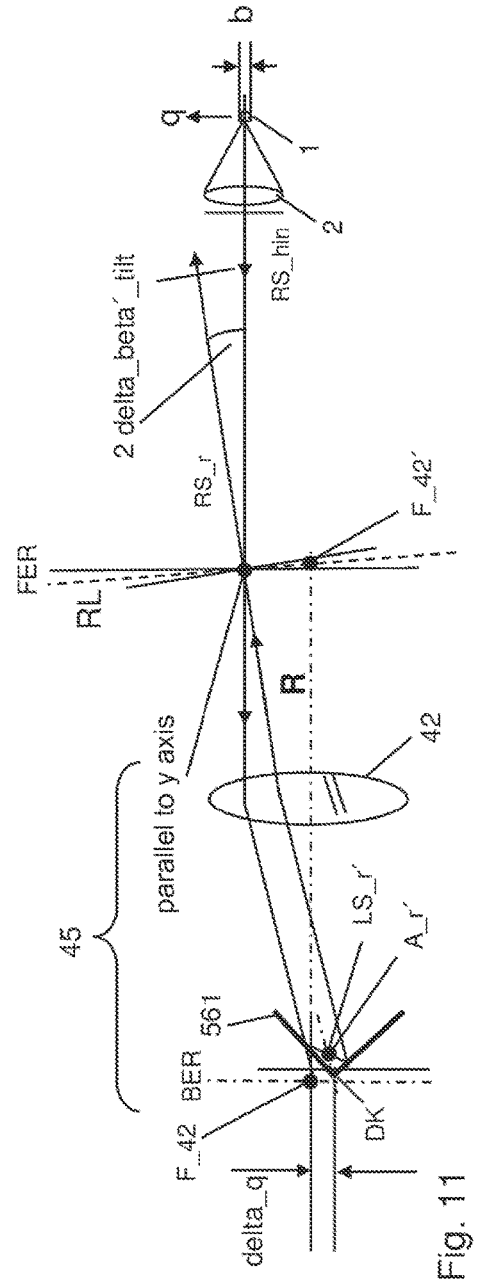

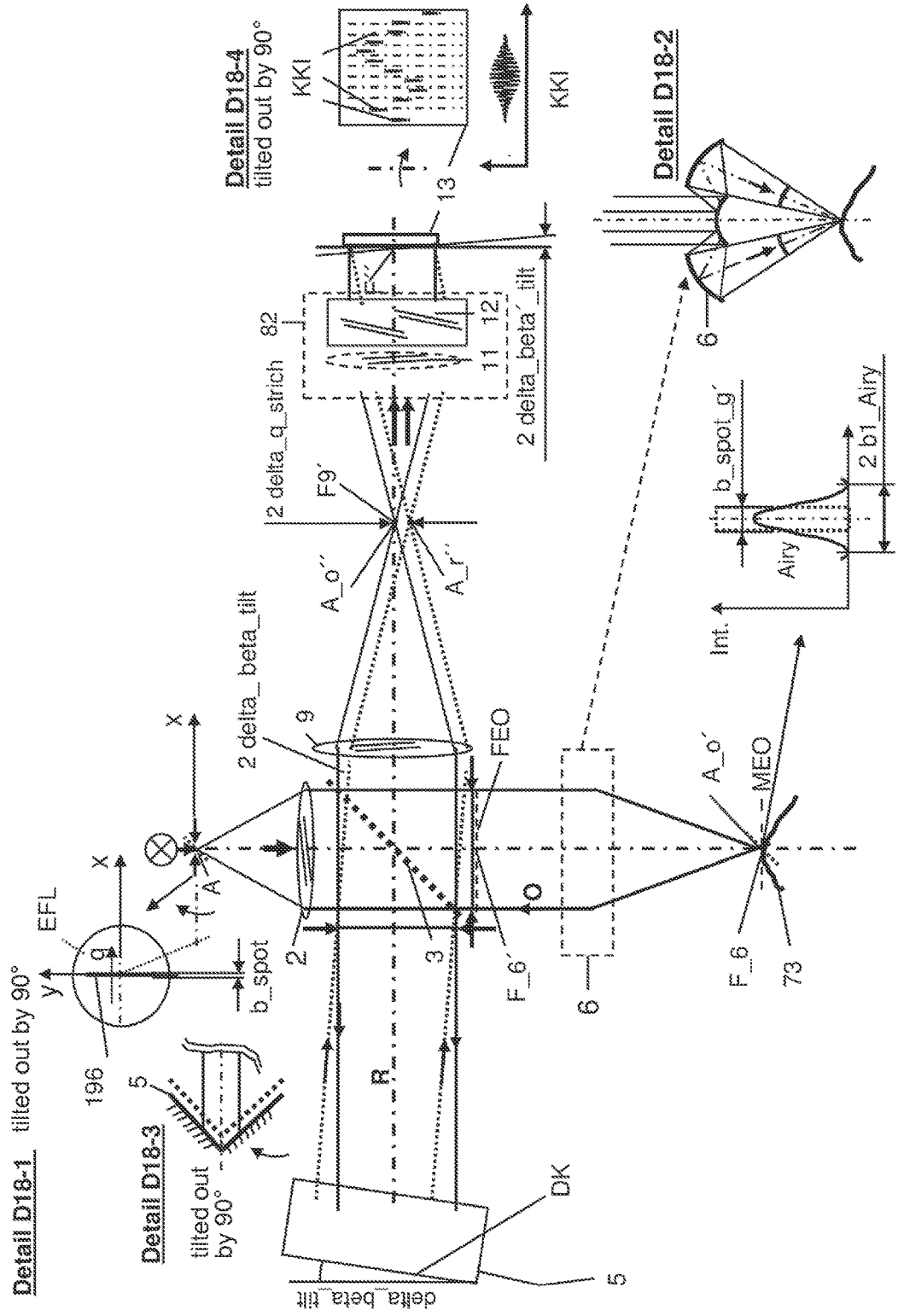

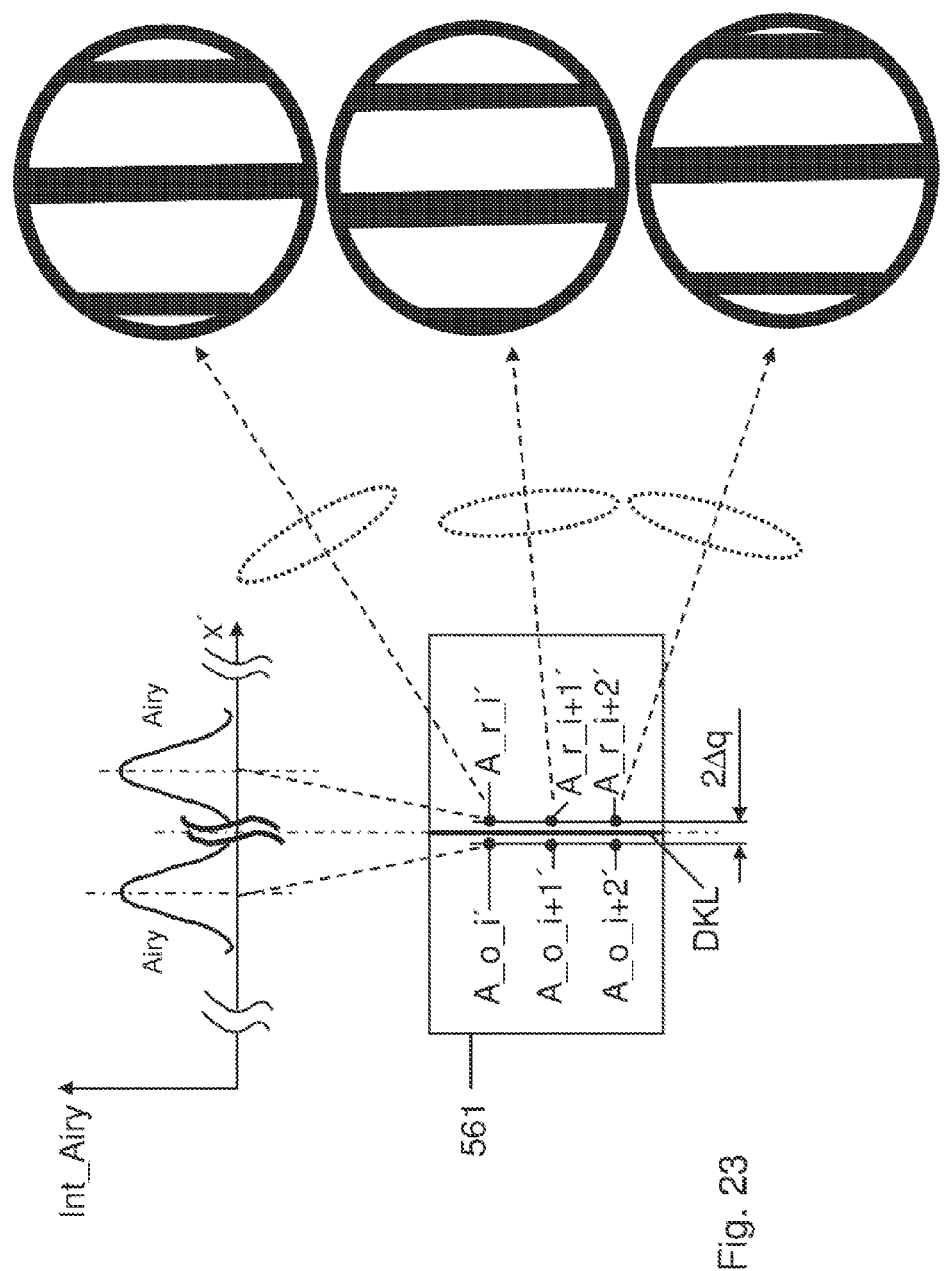

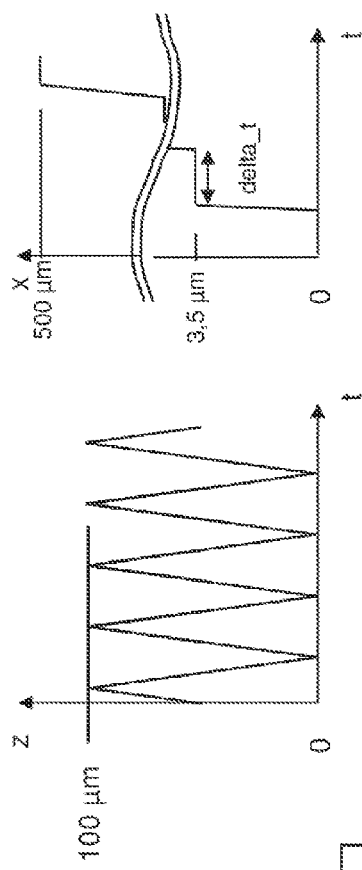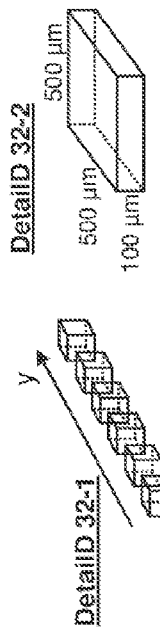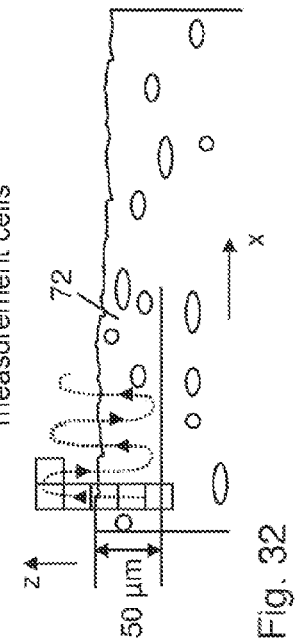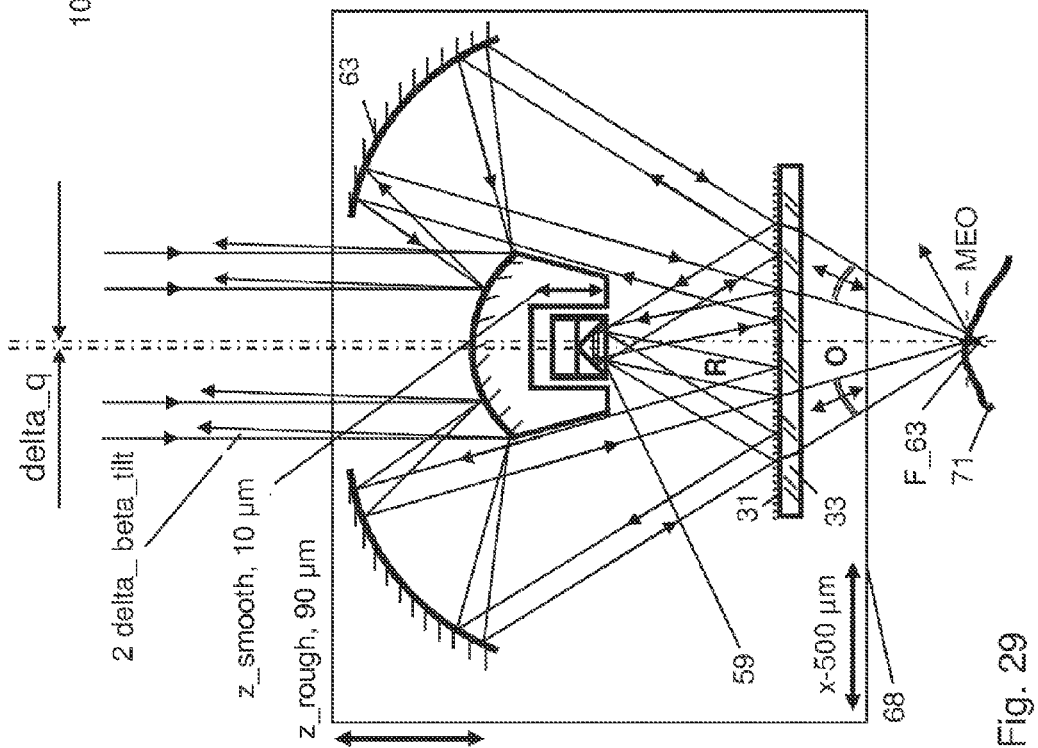

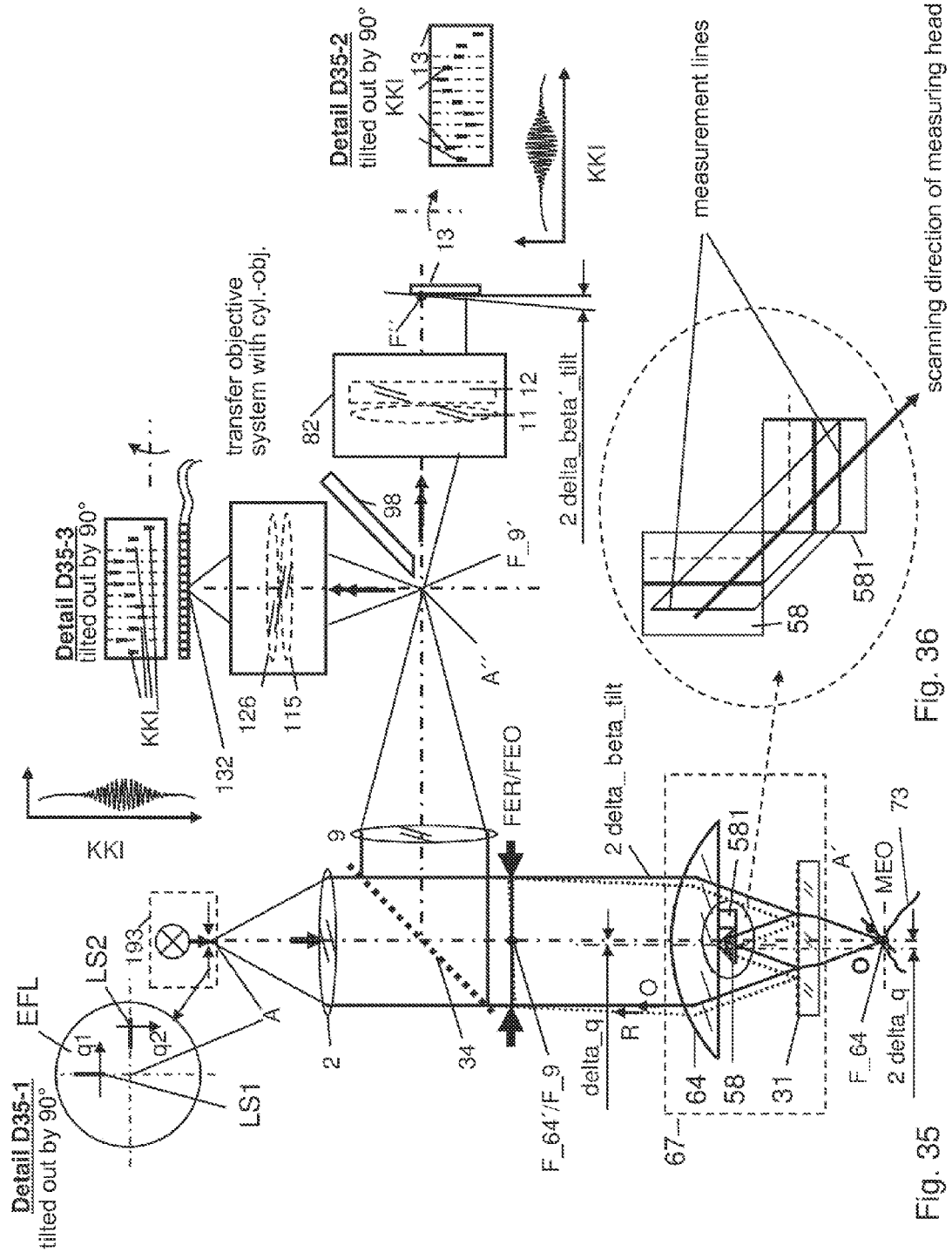

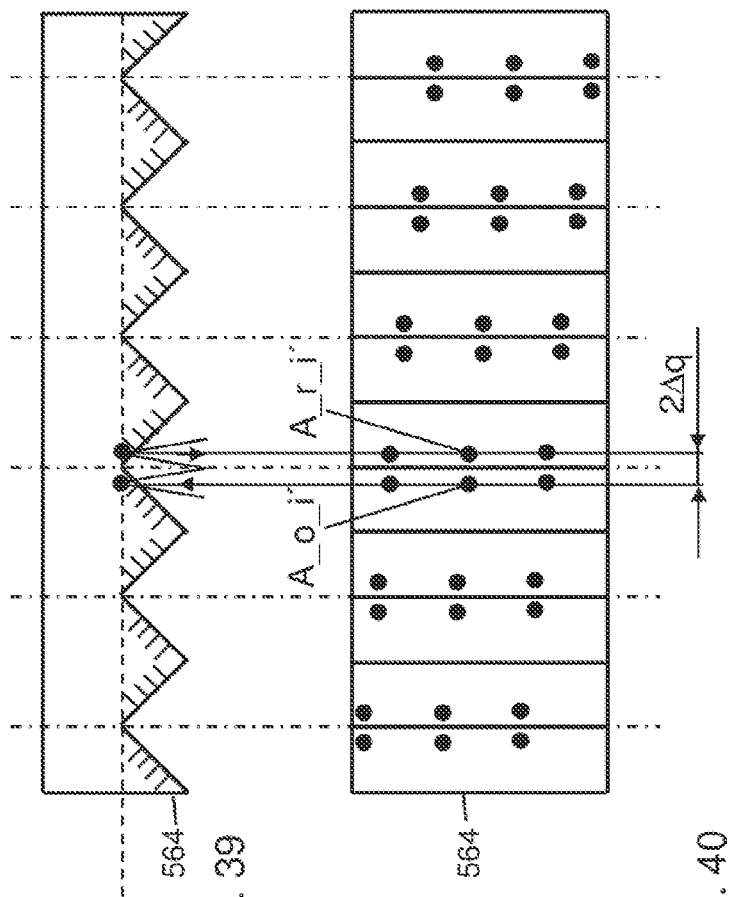
Fig. 39
Fig. 40
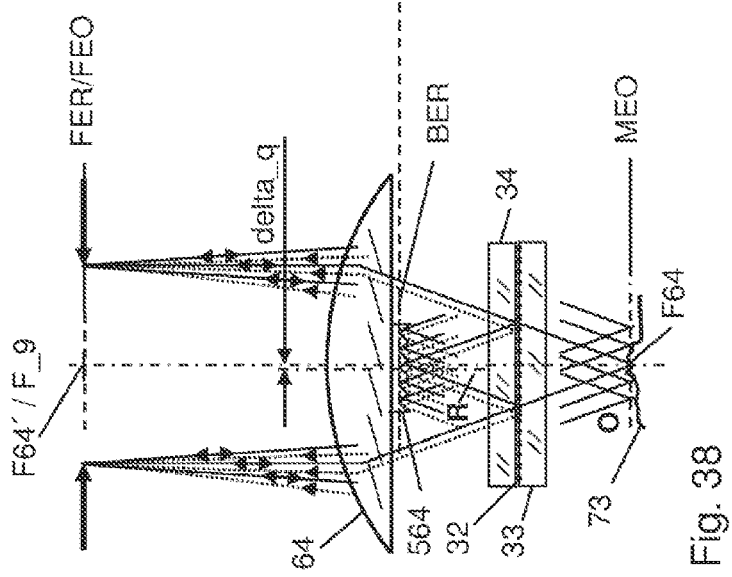
Fig. 38

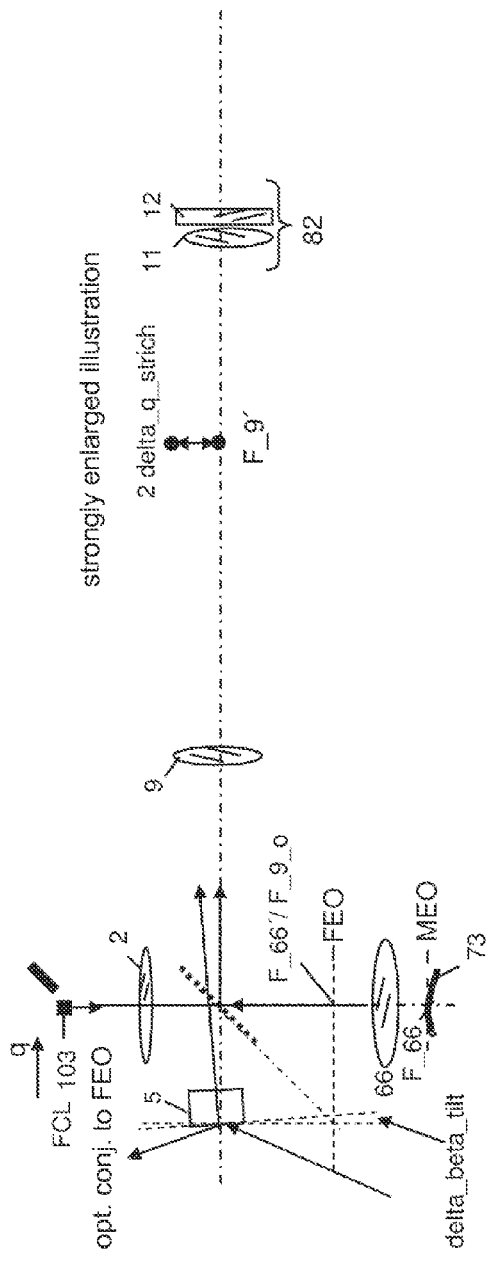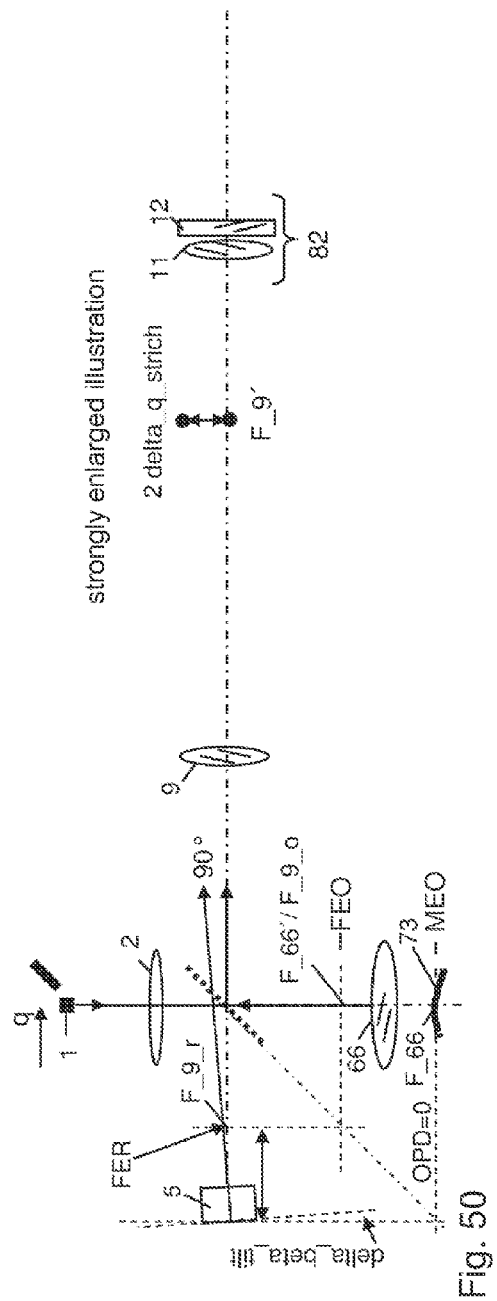

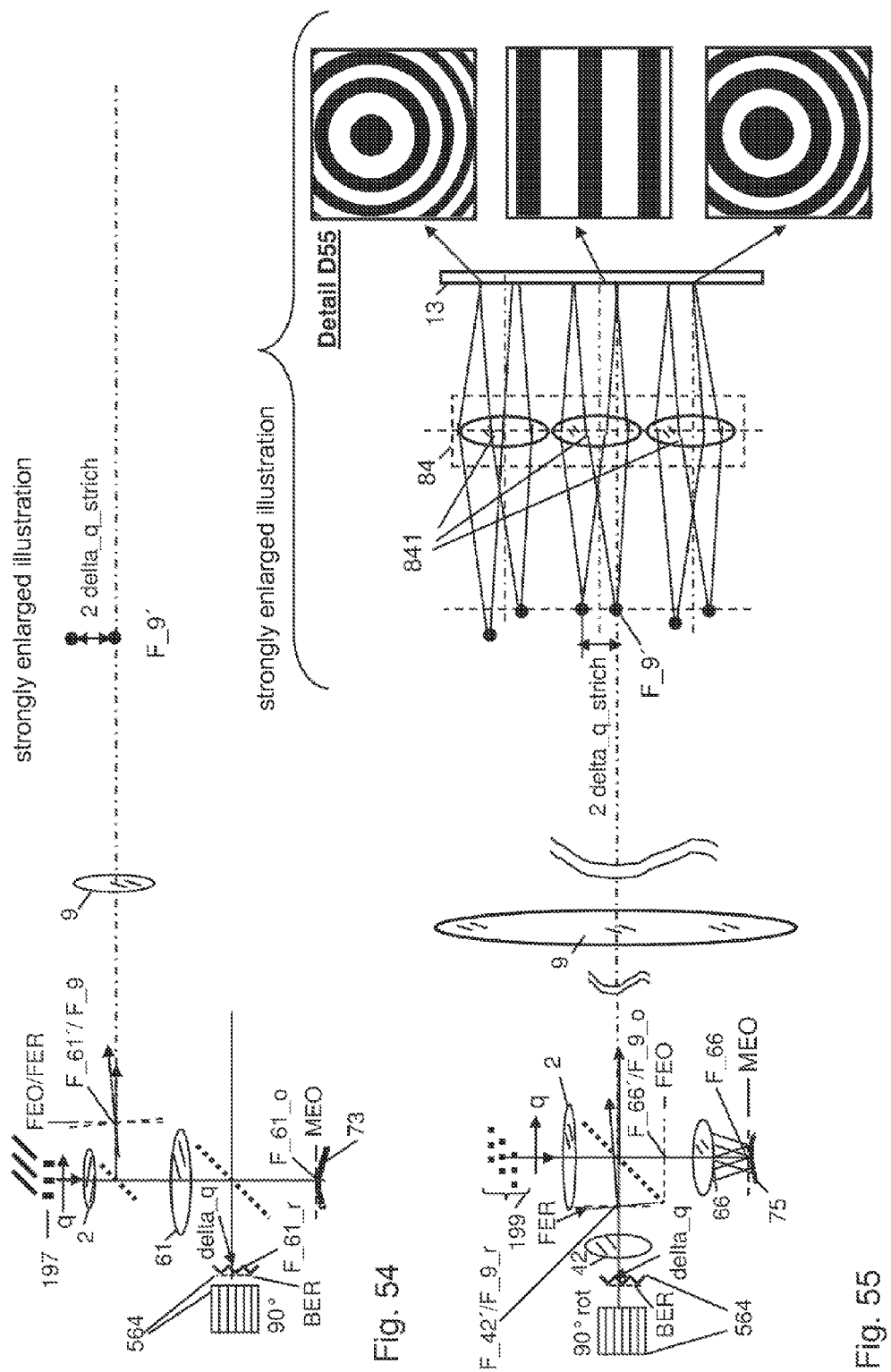

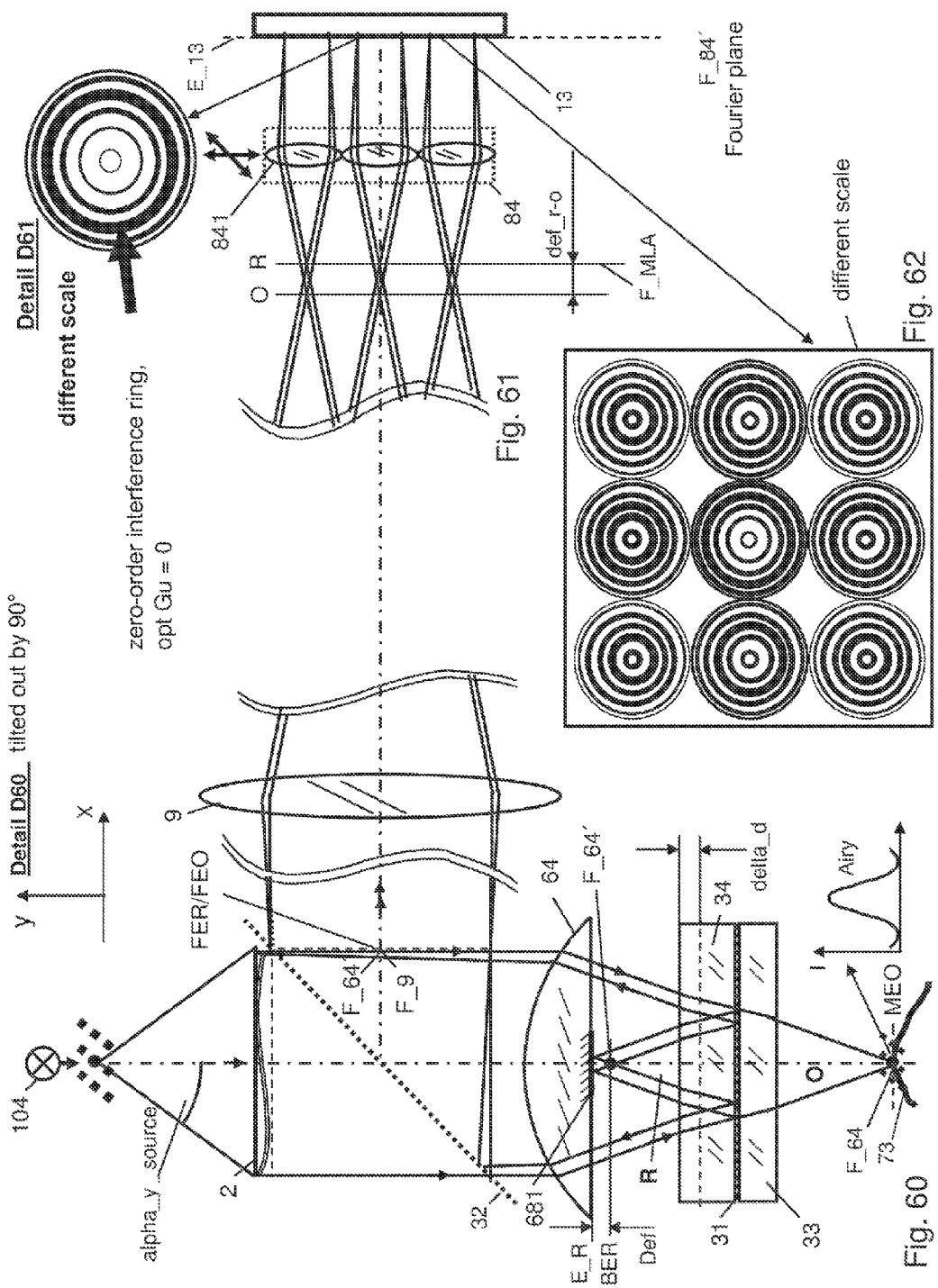

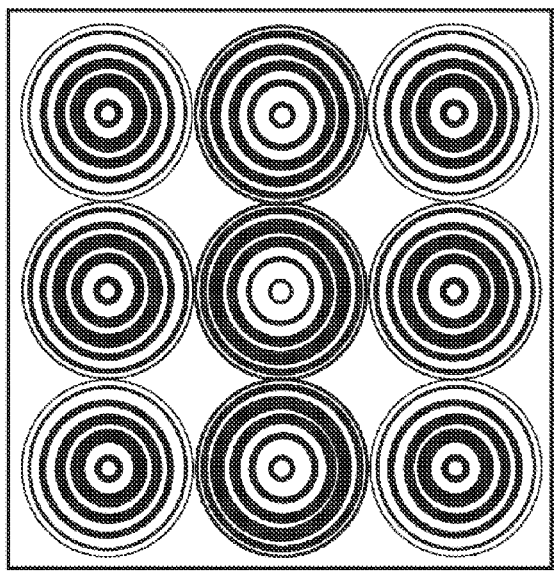
Fig. 64
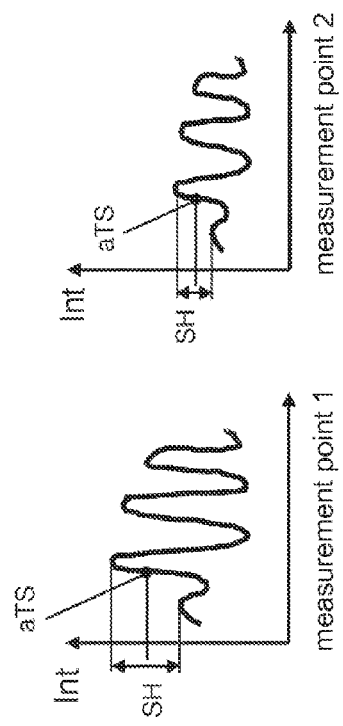
Fig. 65
Fig. 66

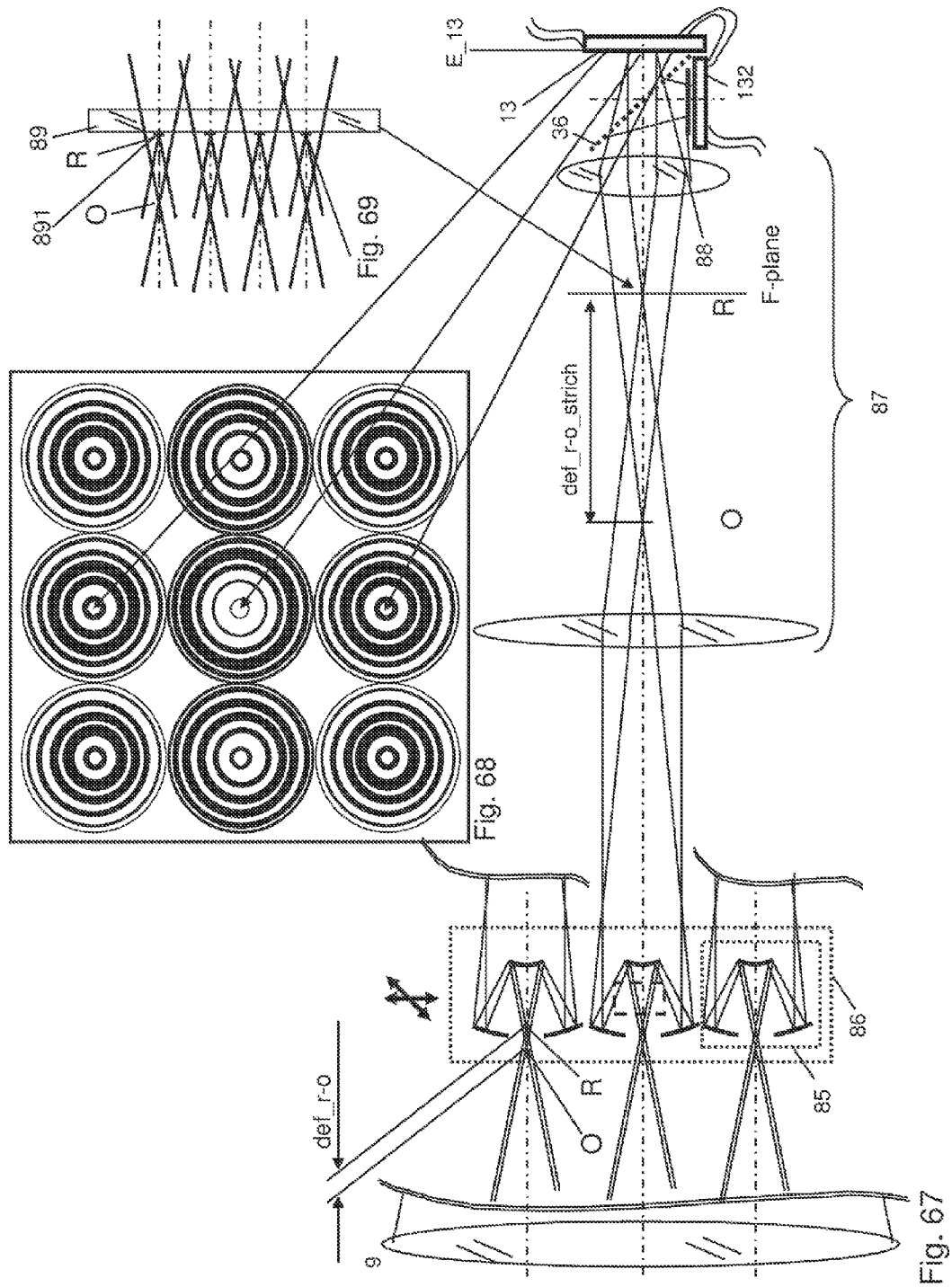

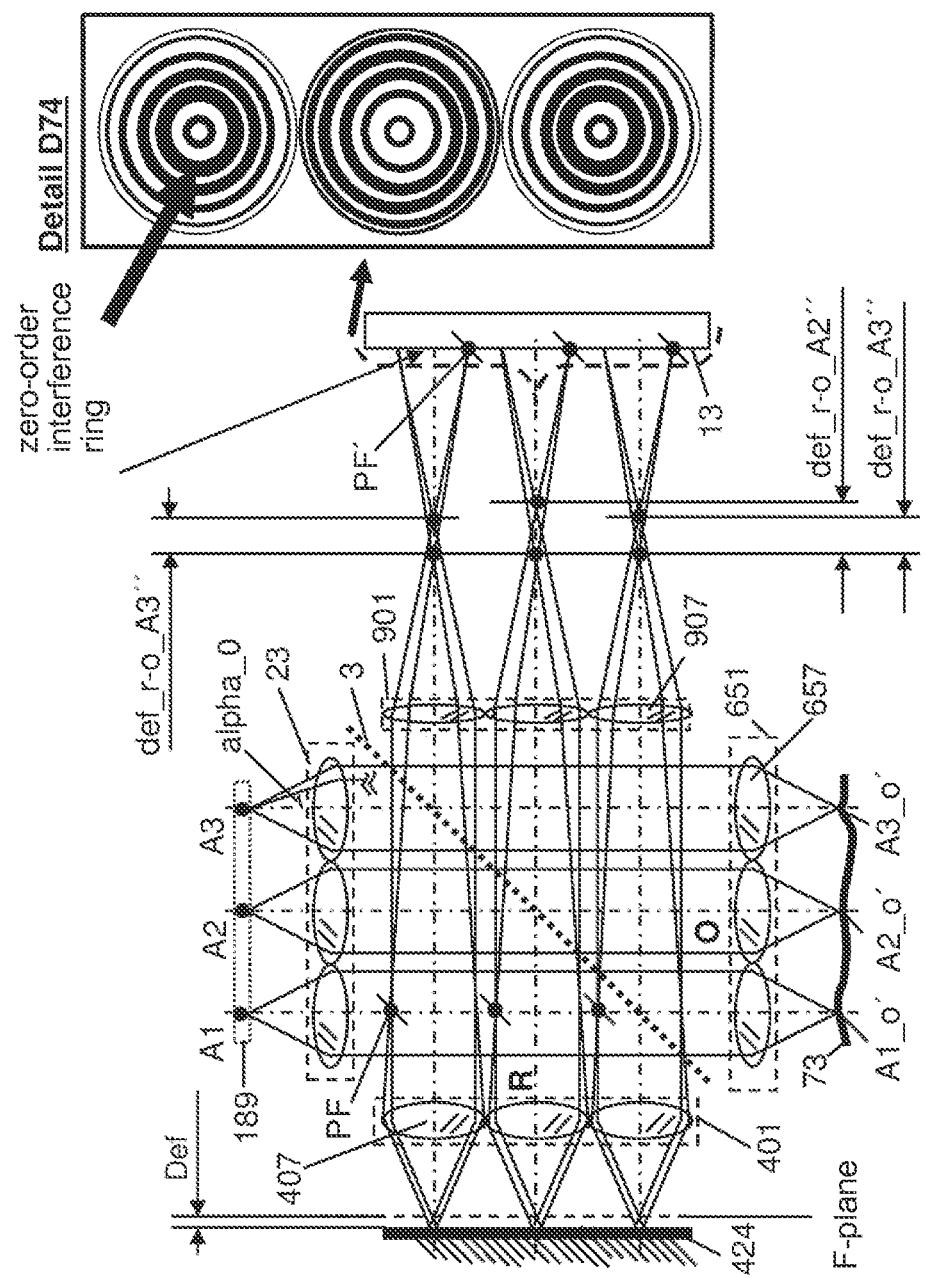

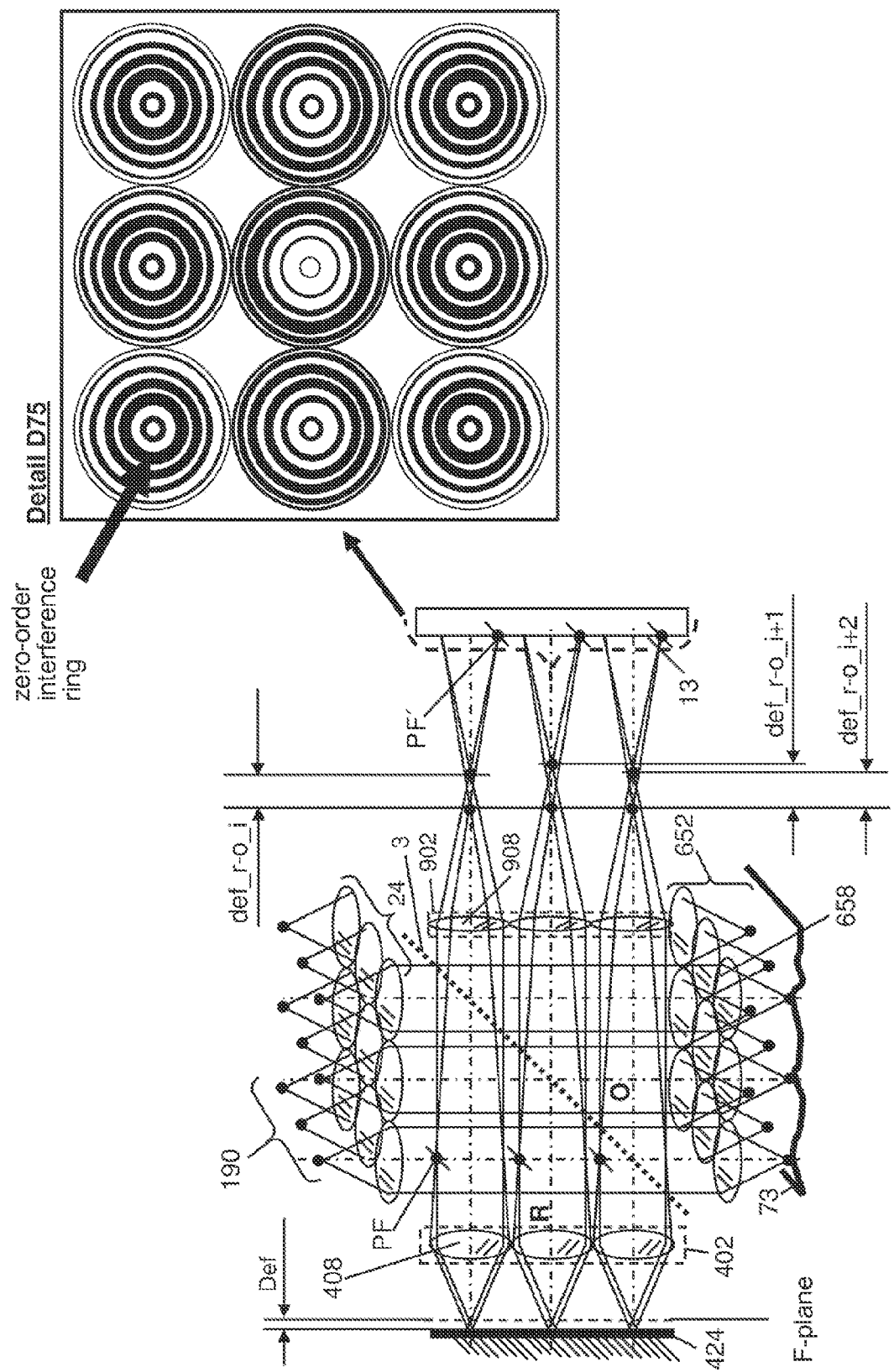

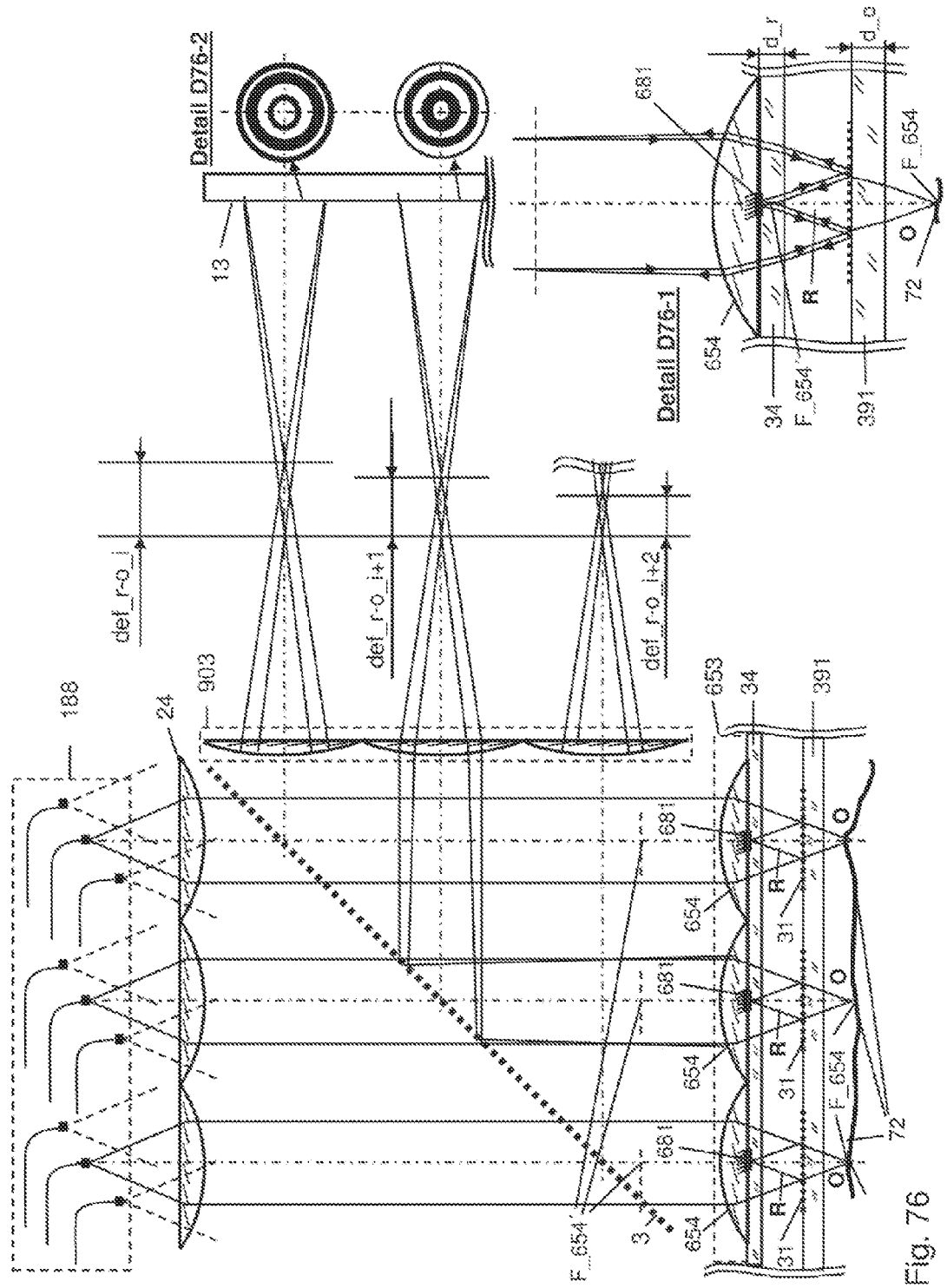

ROBUST ONE-SHOT INTERFEROMETER

RELATED APPLICATIONS

The present application is a U.S. non-provisional filing of German Patent Application No. 10 2013 015 031.0, filed on Sep. 3, 2013, and German Patent Application No. 10 2013 016 752.3, filed on Oct. 2, 2013; and the present application claims priority to and the benefit of both of the above-identified applications, both of which are incorporated by reference herein in their entireties.

BACKGROUND

The present invention relates to a method and an assembly for robust one-shot interferometry, in particular for optical coherence tomography according to the spatial domain approach (SD-OCT) and/or according to the light-field approach. The method and the assembly can be used for measurements on material and living tissue, for distance measurement, for 2D or 3D measurement with a finely structured light source imaged onto the object in a diffraction-limited way, or with spots thereof.

The published patent application DE 10 2006 015 387 A1 [A1] by M. Hering et al. describes an interferometric measuring device on the basis of white light interferometry, also known as short-coherence interferometry, in which the wavefronts of the reflected object beam and those of the reflected reference beam are inclined with respect to each other by a specific angular magnitude by means of an inclination device, such that a spatial interferogram can form as a single one-shot data set. For example, this angular magnitude is realized here in a strongly modified Linnik interferometer arrangement, which also exhibits features of a Mach-Zehnder interferometer, by means of a tilting mirror through which light passes only once on the path to detection. With this optical assembly, it is possible to fully provide one or more spatial interferograms, also as line stacks on a matrix camera, as single-shot data sets in the time period of image acquisition.

It is of particular advantage with this approach that the spatial frequency for the main wavelength, or main wavenumber, in the spatial interferogram at the output of the interferometer is, in a first approximation, not influenced by the inclination of the object surface in relation to the interferometer.

A targeted change in the angular magnitude by means of an inclination device, for example in order to change the spatial frequency for the main wavelength in the spatial interferogram in a predetermined way, may lead to an undesired lateral offset of object wavefront and reference wavefront during detection, which can be compensated for only in a complex manner or cannot be compensated for at all by an alignment in some cases, and may constitute a source of measurement errors or limit the depth measurement range considerably. As a rule, the interferometer is not very stable in the long term.

In the publication by M. Hering et al. in Applied Optics, vol. 48, no. 3, pages 525 to 538 of Jan. 20, 2009 [2], the measured spatial interferograms in image 3 show the potential of this approach according to [1]. The one-shot interferometer measurement assembly illustrated in image 1 represents an experimental setup for purposes of study and is rather too complex and too voluminous to be realized economically. Typical measurement results on the basis of this approach were shown by M. Hering et al. already in 2006 in the Proceedings of SPIE, vol. 6188, 61880E-61880E-1 to 61880E-11 in FIG. 7. By contrast, Michelson-type interferometers having a plane reference mirror, in which the spatial frequency for the main wavelength in a spatial interferogram the output of the interferometer is to be changed by tilting the reference mirror or by tilting the object with respect to the interferometer or the interferometer with respect to the object, are not of interest here for measurement objects having a varying and unknown surface inclination with regard to the evaluation of spatial interferograms. Therefore, such approaches are not considered relevant prior art for this invention and are therefore not dealt with here any further.

Obtaining spatial interferograms for the one-shot measurement technique by means of lateral shear between object and reference wavefronts at the output of a two-beam interferometer is basically a further possibility of generating spatial interferograms for the one-shot measurement technique, for example for detecting distance. In an optical assembly, lateral shear can be used as a basis for generating interferences of mutually tilted wavefronts. A classical approach to this is a Michelson interferometer arrangement having two roof edge reflectors and a laterally extending light source to generate the required lateral shear. This approach with two roof edge reflectors is well known to those skilled in the art, cf. D. Malacara, Optical Shop Testing, John Wiley & Sons, Inc., 1992, pages. 140 to 141, FIG. 4.16 [4] and W. H. Steel, Interferometry, Cambridge University Press, 1967, p. 83 last paragraph to top of p. 84 [5].

In order to be able to use this interferometer approach with two roof edge reflectors for distance measurement and profile measurement, an additional plane mirror needs to be assigned to the object surface in the object arm of the interferometer, wherein this plane mirror together with the object surface then forms a roof edge. Here, the second roof edge reflector is arranged in the reference arm. This assembly, with a corresponding alignment, yields lateral shear between the wavefronts and avoids wavefront inversion, but generally has clear disadvantages owing to the required construction volume in the object arm, for example in the case of measurements in interior spaces.

Also known is the approach published by D. Kelsall in 1959 in Proc. Phys. Society, 73, p. 470, FIG. 1, with two triple reflectors as end reflectors of a Michelson interferometer. The transverse shift of a triple reflector also generates a lateral shear between object and reference wavefronts at the output of a Michelson interferometer. The use of a triple reflector in the reference arm of a Michelson interferometer is, to the best of our knowledge, already known from F. Twyman and A. Green, see also U.S. Pat. No. 1,565,533, FIG. 6, [7].

Using this interferometer approach as an arrangement for an interferometric sensor for distance measurement, inter alia, in which a plane mirror of the triple reflector in the form of a cube corner, also known as corner cube, is replaced by the object surface, has the effect that it is also necessary to assign a roof edge reflector or two plane mirrors to the object or to the object surface in the object arm, as the undesired wavefront inversion between object and reference optical path must be avoided for wide-area measurement, since otherwise the interference contrast will be zero. This approach enlarges the sensor volume considerably, which is very disadvantageous for many applications or entire excludes the use of such a solution.

Document DE 10 2010 006 239 B3 [8] describes an approach in which the use of a triple mirror as an end mirror in the reference arm of the interferometer entails the disadvantage that no focused bundle with a very high numeric aperture can be guided via this reference arm, which is why the measurement range may be limited, since with a high NA, e.g. above 0.7, the light returning from the reference arm is slightly limited in the aperture angle and thus is not able to have the full angular spectrum compared to the object light. This can limit the lateral range of the formation of evaluable interferences on a camera chip noticeably.

The methods and assembly according to DE 10 2010 046 907 B4 [9] have the advantage of using a second interferometer output, and the object points can be arranged almost laterally in an arbitrary manner. Assemblies according to [9] are highly stable with regard to the interferometer alignment state due to the triple reflector in the reference arm, but are also quite complicated in terms of optical circuitry. In addition, in this method, there may be problems with a spherical phase term in the wavelet if the measurement field is extensive, since the effective mirror planes in the reference and object arms do not necessarily coincide, so that a greater number of interferences with the same inclination, also known as Haidinger's rings, may form in the field. This may lead to a violation of the sampling theorem in the detection.

A method according to DE 268771 A1 [10] allows the time-resolved object detection. This approach does rather not allow shot-coherence interferometry for individual measurement points or along individual measurement lines and requires a substantial sensor volume owing to the very high lateral shear.

In Proc. of SPIE 7389, 73891J1 to -73891J12, 2009, [11] and also in PCT document WO2010/139764 A1 [12], K. Gastinger et al. describe the use of micro Mirau interferometers and Twyman-Green interferometers in array form also with a short-coherence light source for parallelized inspection of MEMS and MOEMS. For short-coherence technique, however, the optical path length over time is scanned, so that this is not a one-shot method here. Even moderate vibrations in the surrounding are highly detrimental to wavelet signals to be detected in the scan, according to image 9 at the top in [9], which in the extreme case cannot be evaluated with conventional algorithms any more or yield heavily distorted measurement results.

Already in 1996 did J. Schwider, in DE 196 32 594 A1 [13], suggest a Mach-Zehnder interferometer or a Michelson interferometer with a micro-optical array in the form of a microlens array in the object optical path for the purpose of confocal illumination of the object and confocal discrimination, for two-beam interferometry.

To the best of our knowledge, W. Emer and J. Schwider were the first to describe the use of a Schwarzschild mirror objective in a Mirau arrangement for phase-shift interferometry in the UV range in Applied Optics, 38, no. 16, pp. 3516-3522, 1999 [4]. Here, the optical path difference is varied time-sequentially in order to be able to apply the phase-shift method. Thus, it is neither a one-shot nor a short-coherence method.

In the essay "Holography Viewed from the Perspective of the Light-field Camera" Goodman [15], Joseph W. Goodman describes approaches for Fourier and Fresnel holography with a mask in the image plane. These are derived for the holography by the light-field camera. This essay can be found in the conference documents for Fringe 2013, pp. 3 to 15, 7$^{th}$ International Workshop on Advanced Optical Imaging an Metrology, editor Wolfgang Osten, ISBN 978-3-642-36358-0 ISBN 978-3-642-36359-7 (eBook), DOI 10.1007/978-3-642-36359-7, Springer Heidelberg New York Dordrecht London. This essay was presented in a video conference at the Fringe 2013 in Nürtingen near Stuttgart on Sep. 11, 2013. However, the approach on holography presented by Joseph W. Goodmann does not constitute a teaching for generating two-beam interferograms, in particular also short-coherence interferograms, required for one-shot two-beam interferometry or for optical coherence tomography, which usually can be evaluated numerically very quickly compared to holograms. Here, no teaching is provided for a structured illumination of the object in the light-field approach for two-beam interferometry.

In Stanford Tech Report CTSR 2005-02 [16] in image 1 on page 2, Ren Ng et al. describes light-field photography with a camera according to the plenoptic approach, which has a microlens array in the image plane. However, this assembly cannot be applied to one-shot two-beam interferometry and optical coherence tomography, since usually two-beam interferences cannot be generated with this assembly.

In the patent document U.S. Pat. No. 7,177,029 B2 [17], Peter J. deGroot describes a stroboscopic interferometer, which detects the interferogram data time-serially with a series of light pulses, i.e. based on the time domain method. Consequently, no one-shot measurement can be performed with this approach.

In the published patent application DE 10 2011 000 213 A1 [18], J. Niehues and Peter Lehmann describe an assembly for white-light interference microscopy, in which confocal illumination is produced by means of a spatial light modulator. With this approach, too, it is not possible to perform a one-shot measurement, since it is a time domain approach.

SUMMARY

The following summary is for illustrative purposes only, and it is not intended to limit or constrain the detailed description.

An aim of the invention is to make available for economical use especially robust one-shot measurement technique with a relatively high lateral resolution for detecting distance, depth, profile, shape, waviness and/or roughness or the optical path length in or on technical or biological objects, also in layer form, or for optical coherence tomography (OCT), especially with one-shot multi-point sampling, in which the signals usually arise in wavelet shape. Preferably, the measurement is to be performed in a relatively short measurement time. Furthermore, the tilting and/or inclination of the object surface or its shape, or microform, within certain limits, is to have no or only a minor influence on the signal shape, in particular the spatial frequency of the wavelet.

Particularly preferably, measurements are to be possible also in the case of extreme mechanical impact loads in the measurement field. A further aim is to allow a "flying" multi-point distance measurement, a "flying" 3D measurement, or a "flying" line profile measurement.

Thus, the inventive object to be solved is therefore to provide, during optical scanning of the object surface, of an object point, or of an object volume by means of a two-beam interferometer, optical signals with a signal waveform that can be evaluated in the best possible way, for a punctiform line-like measurement field or for an areal measurement field with many individual measurement points, without a mechanical depth scan that is performed time-serially, said signals allowing a phase evaluation at least for measurement objects that are not or only slightly light-diffusing.

Due to the requirement of a high lateral resolution, it is also an object to form the measuring system with a comparably high numerical aperture up to the boundaries of technical feasibility, including also in immersion technology. By a large and optionally very large numerical aperture, a comparably large proportion of the light radiating onto the object is to be detected, so that the measurement time, according to the objective, can be selected to be comparably short and measurements in a surrounding with strong vibrations, on moved components, or in in-vivo diagnostics of tissue and cells on a living human being are possible. Here, in particular tumor cells are to be reliably detected on the basis of their geometrical structure.

Here, many laterally adjacent object elements or object points are to be measured simultaneously in one measurement. That is, it is the object to provide, for the present state of available evaluation algorithms in short-coherence interferometry and OCT, well evaluable and comparably robust optical signals in the optical scanning of objects by the inventive method and the inventive assembly by means of an interferometer measuring said object, also in the form of a high-aperture interference microscope, in particular with a measuring objective in the object arm, in the fastest possible way.

Here, the spatial frequency for the main wavelength of the signals in wavelet shape, or the main wavenumber, kS in a spatial interferogram is intended to be highly adjustable in a predetermined manner and also highly independent of the inclination of the object surface.

In particular, the object to be solved is to realize the amount of inclination of interfering wavefronts, which form a spatial interferogram on a detector, at least approximately in a predetermined way with simple means.

In particular, the object to be solved is to keep the influence of dispersion for application of refractive components particularly in the interferometric optical path neglectably small or numerically controllable in order to attain a mostly constant center frequency in the arising interference wavelet. This in turn promotes a comparably simple and reliable signal processing of signals derived from spatial interferograms. The influence of dispersion of the object does of course always exist and needs to be taken into account in signal processing and, optionally, be dealt with by suitable algorithms.

In the extreme case, a high-aperture, interferometric 2D or also 3D object detection is to be performed on the basis of the data of a single camera frame, since one-shot data obtained by means of short-pulse technology is self-consistent also in the case of vibrations.

Moreover, information on the angular spectrum are to be obtained for each individual object point. The above objects are solved by the features of the independent claims. Preferred embodiments are subject of the dependent claims.

Fields of Use of the Inventive Solution

Fields of use for the inventive solution are to be: micro-shape and micro-profile measurement, measurement of roughness and also mini-shape measurement, shape measurement on uncooperative or not very cooperative surfaces, such as e.g. human liver tissue. A further field of application is the measurement of polished and also non-polished optical aspheres and freeform surfaces. In this case, an optical material processing system may be assigned to the inventive assembly. This processing system is to be based on the findings of the latest material research and is not part of this invention in terms of its details and the parameterization.

One example of the application of the invention herein includes detection of the microform of living cells, in particular also tumor cells on the living organism.

A special field of application also includes the intraoral measurement of the 3D shape of a tooth, a tooth area, at least in subareas.

The measuring assembly and the method are also intended to be used for optical coherence tomography with spatial interferograms, also known as spatial domain optical coherence tomography (SD-OCT), in particular with fast multi-point scanning for technical or biological objects.

A special field of application may be the biological and medical basic research. For example, the inventive methods and assemblies can be used for understanding the formation and growth, including metabolic processes, of living cells by coupling in particular high-resolution spectral sensor systems.

A further field of use includes the measurement on optically rough object surfaces, where the height values of a measurement point with respect to an adjacent measurement point may differ by more than one fourth of the wavelength.

A further field of application is the in-line measurement of micro-electromechanical systems (MEMS) and micro-opto-electro-mechanical systems (MOEMS). A particular motivation for the application of the invention is the utilization of the interferometric gain of a weak object signal from a rather uncooperative measurement object.

BRIEF DESCRIPTION OF THE DRAWINGS

These and other objects, features, aspects, and advantage of the present disclosure will become better understood with regard to the following description, claims, and drawings. The present disclosure is illustrated by way of example, and not limited by, the accompanying figures in which like numerals indicate similar elements. Moreover, a list of reference numerals and corresponding explanations are provided in Table I.

FIG. 9 illustrates an exemplary tilted roof edge reflector in accordance with one or more aspects of the present disclosure.

FIG. 10 illustrates an exemplary roof edge reflector 5 with a roof edge DK in the reference arm in accordance with one or more aspects of the present disclosure.

FIG. 11 illustrates an exemplary reference optical path in the reference arm in a modified Linnik interferometer in accordance with one or more aspects of the present disclosure.

FIG. 18 illustrates an exemplary hybrid interferometer according to the Linnik approach.

FIG. 19 illustrates an exemplary image of a fine light slit in accordance with one or more aspects of the present disclosure.

FIG. 23 illustrates exemplary coherent Airy spots which are each formed by a finely light source with fine light spots in accordance with one or more aspects of the present disclosure.

FIG. 24 illustrates exemplary spatial interferograms in accordance with one or more aspects of the disclosure.

FIG. 29 illustrates an exemplary Mirau interferometer for white light interferometry with a Schwarzschild objective in accordance with one or more aspects of the present disclosure.

FIG. 30 illustrates an exemplary course of the path of the Mirau interferometer over time in accordance with one or more aspects of the present disclosure.

FIG. 31 illustrates an exemplary path course in x direction over time in the Mirau interferometer in accordance with one or more aspects of the present disclosure.

FIG. 32 illustrates an exemplary scanning path on a living organ in accordance with one or more aspects of the present disclosure.

FIG. 35 illustrates an exemplary Mirau interferometer system for measuring two line profiles arranged perpendicular to each other in accordance with one or more aspects of the present disclosure.

FIG. 36 illustrates an exemplary scanning direction of the measuring head located on a three-coordinates measuring machine in accordance with one or more aspects of the present disclosure.

FIG. 38 illustrates an exemplary multi-line sensor with a 90° hollow roof edge mirror micro end reflector array in combination with a rotationally symmetric reference object in the reference arm in a Mirau configuration in accordance with one or more aspects of the present disclosure.

FIGS. 39-40 illustrate exemplary views of the 90° hollow roof edge mirror micro end reflector array in accordance with one or more aspects of the present disclosure.

FIG. 49 illustrates an exemplary hybrid Linnik interferometer in accordance with one or more aspects of the present disclosure.

FIG. 50 illustrates an exemplary hybrid Linnik interferometer with undesired interferences of the same inclination in the field in accordance with one or more aspects of the present disclosure.

FIG. 54 illustrates an exemplary Michelson interferometer with a g output in accordance with one or more aspects of the present disclosure.

FIG. 55 illustrates an exemplary Linnik interferometer for shape measurement of a small weak asphere in accordance with one or more aspects of the present disclosure.

FIG. 60 illustrates an exemplary Mirau interferometer for micro-shape measurement in accordance with one or more aspects of the present disclosure.

FIG. 61 illustrates an exemplary depth separation of image spots in the detection optical path in accordance with one or more aspects of the present disclosure.

FIG. 62 illustrates exemplary light-field interferences with different phase positions in accordance with one or more aspects of the present disclosure.

FIG. 64 illustrates exemplary ensemble of light-field interferograms—each with a zero-order interference ring—captured by a rasterized detector in accordance with one or more aspects of the present disclosure.

FIGS. 65-66 illustrate exemplary short-coherence wavelets with chirping introduced in a predetermined way in accordance with one or more aspects of the present disclosure.

FIG. 67 illustrates an exemplary interferometer setup operated with pulsed illumination in accordance with one or more aspects of the present disclosure.

FIG. 68 illustrates exemplary spatial interferograms in accordance with one or more aspects of the present disclosure.

FIG. 69 illustrates an exemplary blocking out of the reference light in the interferometer as shown in FIG. 67.

FIGS. 74-75 illustrates an exemplary miniaturized variant of a single-shot approach in the form of a multi-channel Linnik interferometer in accordance with one or more aspects of the present disclosure.

FIG. 76 illustrates an exemplary multi-channel Mirau interferometer approach in accordance with one or more aspects of the present disclosure.

DETAILED DESCRIPTION

Figure 1:
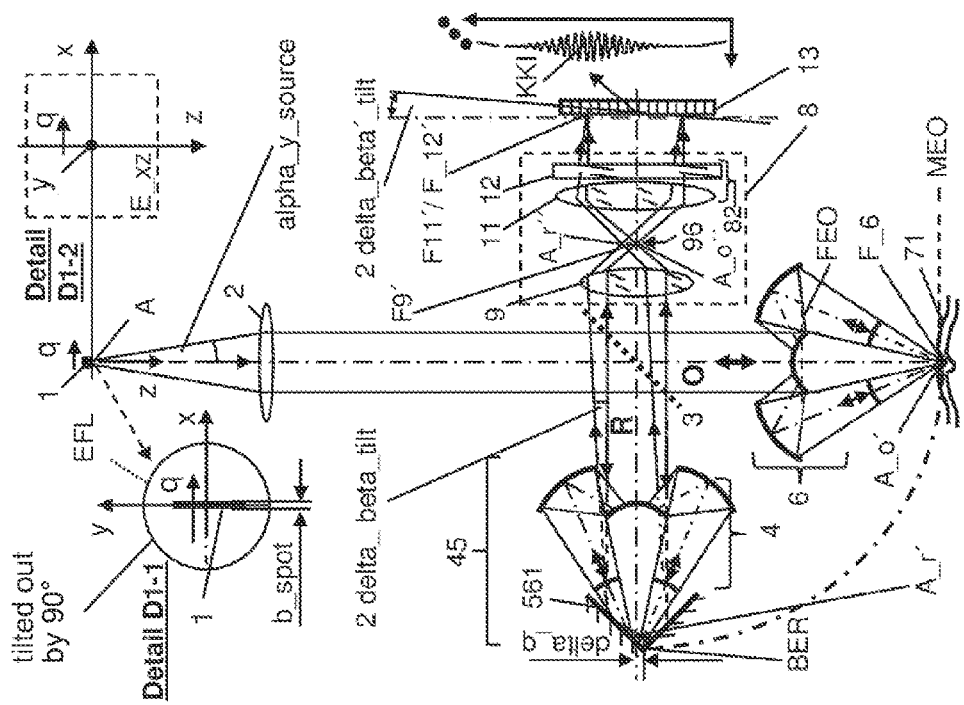
FIG. 1 illustrates an exemplary OCT sensor, measuring in a line-like way, on the basis of a one-shot interferometer in accordance with one or more aspects of the present disclosure.

For the invention described herein, the term light-field interferometry is used by analogy with light-field photography. This approach is described here on the basis of two-beam interferometry and with structured and confocal illumination. Here, the case of two-beam interferometry is intended to be at least approximated, since for light-diffusing objects the transition to multi-beam interference may be smooth. Two-beam interferometer assemblies are used. When a Fizeau interferometer is used, which usually generates interferences—depending on existing reflectivities—with a certain multi-beam characteristic, two-beam interferences arise due to the always existing beam guidance. The illumination of the object—by contrast to holography—is always structured and at least approximately also confocal.

Here, the term light is always used as a synonym for electromagnetic radiation from the terahertz through infrared to the deep UV range.

The difference between the holographic approach according to J. W. Goodman [15] with the light-field camera and the inventive approach is that this case involves two-beam interferometry with confocal, i.e. fine or very finely structured object illumination. Measurement points of the object that are at least approximately in the wave-optical depth of field of the illumination are detected and evaluated. In addition, rather short-coherent light is used for illumination, whereby short-coherence interferograms form.

Evaluating the two-beam interferences described below usually involves less effort than the numerical reconstruction of holograms.

According to of the invention, the following method steps are performed for solving at least one of the objects:
Aspect 1.

In the following, the invention will be described for a measurement method with a single end reflector in the reference arm of a two-beam interferometer.

The method is a method for robust one-shot interferometry, in particular also for spatial domain optical coherence tomography (SD-OCT), particularly for material measurement and also tumor cell detection. It can be used for distance measurement, in particular also for measurement in conjunction with a 3D-coordinates measuring machine, for two or three-dimensional profile measurement, roughness, waviness, and planeness measurement on technical and biological objects, there especially for tumor cell detection by detection of the 3D profile of cells, and for layer measurement.

To this end, a two-beam interferometer having reference and object arms, in particular also in the form of an interference microscope, is used. At least one end reflector is arranged in the reference arm. The two-beam interferometer is particularly formed in an open beam configuration and in particular also as a Michelson, Twyman-Green, Mirau, Linnik, Hybrid-Linnik, or Mach-Zehnder interferometer. The two-beam interferometer comprises the following components:

either at least one line light source formed to be narrow in at least one axial direction
or a line light source array formed with a plurality of at least approximately parallel line spots formed to be narrow in an axial direction.

The axial direction of the narrow configuration is referred to as the transverse axis direction (q).

Moreover, this two-beam interferometer includes the following components:

a light source objective following the line light source or the line light source array, for at least approximately imaging same in a diffraction-limited way,
an objective imaging the object,
a detector objective, wherein the objective imaging the object and the detector objective may also be formed as a single objective,
a rasterized detector with receiver elements for electromagnetic radiation,
and at least one digital computer with at least one evaluation program for detected interferograms for quickly obtaining information on the object.

According to the invention, in the reference arm
either the line light source is formed to be so small in the transverse axis direction (q)
or the line spots of the line light source array are formed to be so small in the transverse axis direction (q)

that for the following light source objective in this transverse axis direction (q), it is/they are at least approximately equal to or below the diffraction-limited lateral resolution thereof, which is determined by the numerical aperture of this light source objective and by the employed wavelength of light or by the employed wavelengths of light of the line light source or the line light source array.

An at least approximately diffraction-limited imaging of the line light source or the line spots of the line light source array onto the object is performed by means of an objective. The Airy width in this imaging situation thus exceeds at least approximately that of the narrow-formed line light source, or the width of the narrow line spots is at least approximately made equal to this Airy width. The Airy width in this imaging situation results from the numerical aperture of the following imaging optical system and the wavelength used.

Moreover, according to the invention:
(i) Either on the one hand
either a hybrid retro reference end reflector (e.g. as the end reflector or as a component of the end reflector) is arranged entirely in the reference arm, said end reflector being formed with a reference objective,
or a hybrid retro reference end reflector system is formed, which is formed with an objective arranged outside the reference arm. The end reflector itself—as a component of the hybrid retro reference end reflector system—is arranged in the reference arm though.

These hybrid retro reference end reflectors are each formed in combination with at least a 90° roof edge end reflector in the reference arm, and the roof edge is respectively at least approximately arranged in the focal plane of the reference objective or of the objective located outside the reference arm. Here, the focal plane of both lenses is always located in the reference space. The roof edge of the 90° roof edge end reflector is respectively arranged at least approximately perpendicular to the transverse axis direction (q) and parallel to the longitudinal direction of the line light source.

By means of this hybrid retro reference end reflector or hybrid retro reference end reflector system, by a transverse offset delta_q of the "roof edge" (DK) at least approximately parallel to the direction of the transverse axis direction (q), either in the focal plane (BER) of the reference objective assigned to the hybrid retro reference end reflector
or in the focal plane (BER) of an objective located outside the reference arm, which objective is assigned both to the reference arm and to the object arm, a transverse offset 2 delta_q_strich of mutually coherent light spots (A_r", A_o") from the reference and object arms is introduced into the focal plane (F_91_r, F_9') upstream of the detector objective.

The transverse offset delta_q of these hybrid retro reference end reflectors is made at most equal to or smaller than the tenth part of the focal length of the reference objective or the objective located outside the reference arm, and at least equal to or greater than the objective-based Airy disk radius for the main wavelength in the detected spatial interferogram.

(ii) Or on the other hand, according to this invention,
a hybrid retro reference end reflector is arranged in the reference arm
which is formed either as a cylinder optics hybrid retro reference end reflector with a cylinder objective having a cylinder axis and a plane mirror in the focal plane of the cylinder objective, and the cylinder axis is respectively perpendicular to the transverse axis direction (q) and parallel to the longitudinal direction of the line light source,
or which is formed as a roof edge reflector and the roof edge is respectively perpendicular to the transverse axis direction (q) and parallel to the longitudinal direction of the line light source.

By a tilt (delta_beta_tilt) the hybrid retro reference end reflector,
wherein the tilt angle is at most made equal to or smaller than 6 degrees (6°) and at least equal to or greater than half a main wavelength in the detected spatial interferogram, based on the illuminated pupil diameter of the objective at the interferometer output (62, 91, 9), respectively about a tilt axis that is at least approximately both perpendicular to the transverse axis direction (q) and perpendicular to the direction of light propagation, respectively based on an unfolded optical path of the two-beam interferometer, a transverse offset 2 delta_q or 2 delta_q_strich of mutually coherent light spots (A_r", A_o") from the reference and object arms is introduced into the focal plane upstream of the detector objective.

In both cases, in the plane of the rasterized detector, by this rasterized detector, preferably upstream optical means for introducing astigmatism into the detection optical path, which are assigned to or downstream of the objective for imaging the object, respectively two interfering wavefronts tilted with respect to each other, one from the object arm (O) and one from the reference arm (R), which preferably have at least approximately a cylinder shape, are formed and made to interfere. Here, at least one spatial interferogram (KKI) is formed and detected by means of the rasterized detector.

Here, the direction of the longitudinal axes of the cylinder wavefronts is respectively at least approximately made to coincide with the transverse axis direction (q)—in the unfolded optical path of the two-beam interferometer—and the tilt axis of the at least one reference cylinder wavefront is respectively at least approximately perpendicular to the transverse axis direction (q).

Aspect 2.

In the following, the invention will be described for a measuring method with an end reflector array in the reference arm of a two-beam interferometer.

The method is a method for robust one-shot interferometry, in particular also for spatial domain optical coherence tomography (SD-OCT), particularly for material measurement and also tumor cell detection. It can be used for distance measurement, in particular also for measurement in conjunction with a 3D-coordinates measuring machine, for two or three-dimensional profile measurement, roughness, waviness, and planeness measurement on technical and biological objects, there especially for tumor cell detection by detection of the 3D profile of cells, and for layer measurement.

To this end, a two-beam interferometer having reference and object arms, in particular also in the form of an interference microscope, is used. At least one end reflector is arranged in the reference arm. The two-beam interferometer is particularly formed in an open beam configuration and in particular also as a Michelson, Twyman-Green, Mirau, Linnik, Hybrid-Linnik, or Mach-Zehnder interferometer. The two-beam interferometer comprises the following components:

either at least one line light source formed to be narrow in at least one axial direction or a line light source array formed with a plurality of at least approximately parallel line spots formed to be narrow in an axial direction.

The axial direction of the narrow configuration is referred to as the transverse axis direction (q).

Moreover, this two-beam interferometer includes the following components:

a light source objective following the line light source or the line light source array, for at least approximately imaging same in a diffraction-limited way, an objective imaging the object, a detector objective, wherein the objective imaging the object and the detector objective may also be formed as a single objective, a rasterized detector with receiver elements for electromagnetic radiation, and at least one digital computer with at least one evaluation program for detected interferograms for quickly obtaining information on the object.

According to the invention, in the reference arm:

either the line light source is formed to be so small in the transverse axis direction (q)

or the line spots of the line light source array are formed to be so small in the transverse axis direction (q)

that for the following light source objective in this transverse axis direction (q), it is/they are at least approximately equal to or below the diffraction-limited lateral resolution thereof, which is determined by the numerical aperture of this light source objective and by the employed wavelength of light or by the employed wavelengths of light of the line light source or the line light source array.

An at least approximately diffraction-limited imaging of the line light source or the line spots of the line light source array onto the object is performed by means of an objective.

The Airy width in this imaging situation thus exceeds at least approximately that of the narrow-formed line light source, or the width of the narrow line spots is at least approximately made equal to this Airy width. The Airy width in this imaging situation results from the numerical aperture of the following imaging optical system and the wavelength used.

According to the invention, on the one hand, either a hybrid retro reference end reflector system is arranged in the reference arm R, said system being formed with a reference objective, or, on the other hand, a hybrid retro reference end reflector system is arranged, which is formed with an objective located outside the reference arm This hybrid retro reference end reflector system is respectively formed in combination with either a hybrid retro reference micro end reflector array with hybrid retro reference micro end reflectors of the 90° roof edge mirror type or 90° roof edge prism type;

or a reference micro end reflector array with hybrid retro micro reference end reflectors of the cylinder objective cat's eye type or of the cylinder mirror cat's eye type in the reference arm.

This hybrid retro reference end reflector system is respectively at least approximately arranged in the focal plane of the reference objective or of the objective located outside the reference arm.

By means of the hybrid retro reference end reflector system, by a transverse offset delta_q of these hybrid retro micro reference end reflectors of the cylinder cat's eye type or of the 90° roof-edge type at least approximately parallel to the direction of the transverse axis direction (q), either in the focal plane (BER) of the reference objective (4 42) assigned to the hybrid retro reference end reflector or in the focal plane (BER) of an objective located outside the reference arm, which objective is assigned both to the reference arm and to the object arm, is introduced.

Thus, a transverse offset 2 delta_q_strich of mutually coherent light spots (A_r", A_o") from the reference and object arms is introduced into the focal plane (F_91_r, F_9') upstream of the detector objective as well.

The transverse offset delta_q of these hybrid retro micro reference end reflectors is made at most equal to or smaller than the tenth part of the focal length of the reference objective or the objective located outside the reference arm, and at least equal to or greater than the objective-based Airy disk radius for the main wavelength in the detected spatial interferogram.

In both cases, in the plane of the rasterized detector, by this rasterized detector, preferably upstream optical means for introducing astigmatism into the detection optical path, which are assigned to or downstream of the objective for imaging the object, a plurality of respectively two interfering wavefronts tilted with respect to each other, one from the object arm (O) and one from the reference arm (R), which preferably have at least approximately a cylinder shape, are formed and made to interfere. Here, a plurality of spatial interferograms (KKI) is formed and detected by means of the rasterized detector.

Here, the direction of the longitudinal axes of the cylinder wavefronts is respectively at least approximately made to coincide with the transverse axis direction (q)—in the unfolded optical path of the two-beam interferometer—and the tilt axis of the at least one reference cylinder wavefront is respectively at least approximately perpendicular to the transverse axis direction (q).

Aspect 3.

In the following, the invention will be described for a measuring method with an end reflector array in the reference arm of a two-beam interferometer.

The method is a method for robust one-shot interferometry, in particular also for spatial domain optical coherence tomography (SD-OCT), particularly for material measurement and also tumor cell detection. It can be used for distance measurement, in particular also for measurement in conjunction with a 3D-coordinates measuring machine, for two or three-dimensional profile measurement, roughness, waviness, and planeness measurement on technical and biological objects, there especially for tumor cell detection by detection of the 3D profile of cells, and for layer measurement.

To this end, a two-beam interferometer having reference and object arms, in particular also in the form of an interference microscope, is used. At least one end reflector is arranged in the reference arm. The two-beam interferometer is particularly formed in an open beam configuration and in particular also as a Michelson, Twyman-Green, Mirau, Linnik, Hybrid-Linnik, or Mach-Zehnder interferometer. The two-beam interferometer comprises the following components:

either at least one finely formed point light source or a finely formed point light source matrix formed with a plurality of finely formed spots, a light source objective following the light source, for at least approximately imaging same or the spots in a diffraction-limited way, an objective imaging the object, a detector objective, wherein the objective imaging the object and the detector objective may also be formed as a single objective, a rasterized detector with receiver elements for electromagnetic radiation, and at least one digital computer with at least one evaluation program for detected interferograms for quickly obtaining information on the object.

According to the invention, in the reference arm, either the finely formed point light source is formed to be so fine, or, in the reference arm, the spots of the finely formed point light source matrix are each formed to be so fine that for the following light source objective it is/they are at least approximately equal to or below the diffraction-limited lateral resolution thereof, which is determined by the numerical aperture of this light source objective and by the employed wavelength of light or by the employed wavelengths of the finely formed light source (198) or the finely formed point light source matrix.

Either by means of a full retro reference micro end reflector system R with a reference objective in the reference arm or with a hybrid retro reference end reflector system, arranged in the reference arm R, having an objective located outside the reference arm, and with full retro reference micro end reflectors respectively in either a micro end reflector array with full retro micro reference end reflectors of the rotationally symmetric lens cat's eye type or a micro end reflector array with full retro reference micro end reflectors of the rotationally symmetric mirror cat's eye type or a triple prism mirror micro end reflector array with triple prism mirror micro end reflectors or a concave triple mirror micro end reflector array with triple mirror micro end reflectors and in the micro end reflectors, respectively a transverse offset delta_q exists in the focal plane of the associated reference objective, said transverse offset being made at most equal to or smaller than the tenth part of the focal length of this reference objective and at least equal to or greater than the objective-based Airy disk radius for the main wavelength in the detected spatial interferogram, a transverse offset 2 delta_q or 2 delta_q_strich of mutually coherent light spots (A_r'', A_o'') from the reference and object arms is introduced into the focal plane upstream of the detector objective. The transverse offset is made at least equal to or greater than the objective-based Airy disk radius for the main wavelength in the detected spatial interferogram, In the plane of the rasterized detector, by this rasterized detector, preferably upstream optical means for introducing astigmatism into the detection optical path, which are assigned to or downstream of the objective for imaging the object, respectively two interfering wavefronts tilted with respect to each other, one from the object arm (O) and one from the reference arm (R), which preferably have at least approximately a cylinder shape, are formed and made to interfere. Here, a plurality of spatial interferograms (KKI) is formed and detected by means of the rasterized detector.

Here, the direction of the longitudinal axes of the cylinder wavefronts is respectively at least approximately made to coincide with the transverse axis direction (q)—in the unfolded optical path of the two-beam interferometer—and the tilt axis of the at least one reference cylinder wavefront is respectively at least approximately perpendicular to the transverse axis direction (q).

Aspect 4.

Moreover, in the method for robust one-shot interferometry according to one or more of the above aspects, the direction of the longitudinal axes of the cylinder wavefronts is preferably at least approximately made to coincide with the transverse axis direction (q)—in the unfolded optical path of the two-beam interferometer—and the tilt axis of the at least one reference cylinder wavefront is respectively at least approximately perpendicular to the transverse axis direction (q). In the case of a line light source, it coincides with the longitudinal extension direction of the line light source or the longitudinal extension direction of elongated light spots of a light source.

Aspect 5.

Moreover, in the method for robust one-shot interferometry according to one or more of the above aspects, in the section including the transverse axis direction (q), the Fourier plane (FEO) of the object-imaging objective is at least approximately imaged sharply onto the rasterized detector by optical means, and in the section perpendicular thereto, which in the unfolded optical path is parallel to the longitudinal direction of the line source, the measurement plane of the object (MEO) is imaged sharply onto the rasterized detector by optical means, so that astigmatic imaging occurs in the detection optical path.

The wavefront inversion does not constitute an explicit advantage here. Instead, one has to accept that. It is not desired, but can be tolerated due to diffraction-limited imaging of small spots of the light source.

Aspect 6.

Moreover, in the method for robust one-shot interferometry according to one or more of the above aspects, preferably in the imaging process in an intermediate image plane ZBE, confocal discrimination at least for the object light is performed by means of optical means for low-pass filtering. Thereby, the stray light from the depth of the object is reduced in a known way. Further, it serves for low-pass filtering of the object light, which can result in an improvement of signal quality in the detected spatial interferograms.

In the method for robust one-shot interferometry, preferably in the object arm, chromatic depth decomposition is performed with the help of means variable in refractive power over the wavelength. Thus, the wave-optically related depth measurement range can be increased substantially in the measuring method.

Aspect 7.

Moreover, in the method for robust one-shot interferometry according to one or more of the above aspects, preferably in the imaging process in an intermediate image plane ZBE, low-pass filtering by means of optical means is performed for the object light.

In the method for robust one-shot interferometry, preferably further spectral decomposition, or splitting, is performed in the detection optical path for increasing the coherence length, and thus a separation of the interferograms of different wavelength or wavelength ranges on the rasterized receiver.

The spectral decomposition in the detection optical path results in an increased coherence length, which in turn causes an increase in the surface area with evaluable high-contrast interferences on the detector and thus also provides the possibility of performing multi-wavelength evaluation with phase evaluation. This phase evaluation yields the optical path difference of zero at least approximately, even if only parts of the interferogram exist or also information on the non-evaluability of the measurement point, for example due to excessive speckling in the interferogram.

In the method for robust one-shot interferometry, preferably a computer-controlled lateral displacement of the line spot(s) of the line light source or the line light source array is performed. Thus, the measurement field can be detected completely.

In the method for robust one-shot interferometry, preferably a computer-controlled lateral displacement of the end reflector(s) or the end reflector array is performed. Thus, the measurement field can be detected completely.

In the method for robust one-shot interferometry, preferably a computer-controlled lateral displacement of the line spot(s) of the line light source or the line light source array is performed. Thus, the measurement field can be detected completely.

In the method for robust one-shot interferometry, preferably a computer-controlled lateral displacement of the end reflector(s) or the end reflector array and the computer-controlled lateral displacement of the line spot(s) of the line light source or the line light source array are performed in a way synchronized to each other.

In the method for robust one-shot interferometry, preferably an immersion technique is used in the object arm. In this way, it is also possible to measure objects in a liquid environment.

In the method for robust one-shot interferometry, preferably an immersion technique is used in the object arm and in the reference arm.

In the method for robust one-shot interferometry, preferably the centroid of the envelope of a short-coherent, spatial interferogram (KKI) is evaluated.

In the method for robust one-shot interferometry, preferably the phase of a spatial interferogram (KKI) is evaluated.

In the following, the invention will be described for a measuring assembly having a single end reflector in the reference arm of a two-beam interferometer.

According to the invention, the following assembly features exist for solving at least one of the objects:

Aspect 8.

In the following, the invention will be described for a measuring assembly having a single end reflector in the reference arm of a two-beam interferometer.

The assembly is an assembly for robust one-shot interferometry, in particular also for spatial domain optical coherence tomography (SD-OCT), particularly for material measurement and also tumor cell detection. It can be used for distance measurement, in particular also for measurement in conjunction with a 3D-coordinates measuring machine, for two or three-dimensional profile measurement, roughness, waviness, and planeness measurement on technical and biological objects, there especially for tumor cell detection by detection of the 3D profile of cells, and for layer measurement.

To this end, a two-beam interferometer having reference and object arms, in particular also in the form of an interference microscope, is used. At least one end reflector is arranged in the reference arm. The two-beam interferometer is particularly formed in an open beam configuration and in particular also as a Michelson, Twyman-Green, Mirau, Linnik, Hybrid-Linnik, or Mach-Zehnder interferometer. The two-beam interferometer comprises the following components:

either at least one line light source formed to be narrow in at least one axial direction or a line light source array formed with a plurality of at least approximately parallel line spots formed to be narrow in an axial direction.

The axial direction of the narrow configuration is referred to as the transverse axis direction (q).

Moreover, the two-beam interferometer includes the following components:

a light source objective following the line light source or the line light source array, for at least approximately imaging same in a diffraction-limited way, an objective imaging the object, a detector objective, wherein the objective imaging the object and the detector objective may also be formed as a single objective, a rasterized detector with receiver elements for electromagnetic radiation, and at least one digital computer with at least one evaluation program for detected interferograms for quickly obtaining information on the object.

According to the invention, in the reference arm either the line light source is formed to be so small in the transverse axis direction (q)

or the line spots of the line light source array are formed to be so small in the transverse axis direction (q)

that for the following light source objective in this transverse axis direction (q), it is/they are at least approximately equal to or below the diffraction-limited lateral resolution thereof, which is determined by the numerical aperture of this light source objective and by the employed wavelength of light or by the employed wavelengths of light of the line light source or the line light source array.

An at least approximately diffraction-limited imaging of the line light source or the line spots of the line light source array onto the object is performed by means of an objective. The Airy width in this imaging situation thus exceeds at least approximately that of the narrow-formed line light source, or the width of the narrow line spots is at least approximately made equal to this Airy width. The Airy width in this imaging situation results from the numerical aperture of the following imaging optical system and the wavelength used. The Airy width in this imaging situation thus exceeds at least approximately that of the narrow-formed line light source, or the width of the narrow line spots is at least approximately made equal to this Airy width.

Moreover, according to the invention:

(i) Either on the one hand
  either a hybrid retro reference end reflector is arranged entirely in the reference arm, said end reflector being formed with a reference objective,
  or a hybrid retro reference end reflector system is formed, which is formed with an objective arranged outside the reference arm. The end reflector itself—as a component of the hybrid retro reference end reflector system—is arranged in the reference arm though.
  These hybrid retro reference end reflectors are each formed in combination with at least a 90° roof edge end reflector in the reference arm, and the roof edge is respectively at least approximately arranged in the focal plane of the reference objective or of the objective located outside the reference arm. Here, the focal plane of both lenses is always located in the reference space. The roof edge of the 90° roof edge end reflector is respectively arranged at least approximately perpendicular to the transverse axis direction (q) and parallel to the longitudinal direction of the line light source.
  By means of this hybrid retro reference end reflector, by a transverse offset delta_q of the "roof edge" (DK) at least approximately parallel to the direction of the transverse axis direction (q),
    either in the focal plane (BER) of the reference objective assigned to the hybrid retro reference end reflector
    or in the focal plane (BER) of an objective located outside the reference arm, which objective is assigned both to the reference arm and to the object arm,
  a transverse offset 2 delta_q_strich of mutually coherent light spots (A_r", A_o") from the reference and object arms is introduced into the focal plane (F_91_r, F_9') upstream of the detector objective.
  The transverse offset delta_q of these hybrid retro micro reference end reflectors is made at most equal to or smaller than the tenth part of the focal length of the reference objective or the objective located outside the reference arm, and at least equal to or greater than the objective-based Airy disk radius for the main wavelength in the detected spatial interferogram.

(ii) Or on the other hand, according to the invention,
  a hybrid retro reference end reflector is arranged in the reference arm
    which is formed either as a cylinder optics hybrid retro reference end reflector with a cylinder objective having a cylinder axis and a plane mirror in the focal plane of the cylinder objective, and the cylinder axis is respectively perpendicular to the transverse axis direction (q) and parallel to the longitudinal direction of the line light source,
    or which is formed as a roof edge reflector and the roof edge is respectively perpendicular to the transverse axis direction (q) and parallel to the longitudinal direction of the line light source.

Here, the tilt angle is at most made equal to or smaller than 6 degrees (6°) and at least equal to or greater than half a main wavelength lambda_S in the detected spatial interferogram, based on the illuminated pupil diameter of the objective at the interferometer output (62, 91, 9), respectively about a tilt axis that is at least approximately both perpendicular to the transverse axis direction (q) and perpendicular to the direction of light propagation, respectively based on an unfolded optical path of the two-beam interferometer.

The rasterized detector preferably has upstream optical means for introducing astigmatism into the detection optical path, which are assigned to or downstream of the objective for imaging the object.

Aspect 9.

In the following, the invention will be described for an assembly with an end reflector array in the reference arm of a two-beam interferometer.

The assembly is an assembly for robust one-shot interferometry, in particular also for spatial domain optical coherence tomography (SD-OCT), particularly for material measurement and also tumor cell detection. It can be used for distance measurement, in particular also for measurement in conjunction with a 3D-coordinates measuring machine, for two or three-dimensional profile measurement, roughness, waviness, and planeness measurement on technical and biological objects, there especially for tumor cell detection by detection of the 3D profile of cells, and for layer measurement.

To this end, a two-beam interferometer having reference and object arms, in particular also in the form of an interference microscope, is used. At least one end reflector is arranged in the reference arm. The two-beam interferometer is particularly formed in an open beam configuration and in particular also as a Michelson, Twyman-Green, Mirau, Linnik, Hybrid-Linnik, or Mach-Zehnder interferometer. The two-beam interferometer comprises the following components:
  either at least one line light source formed to be narrow in at least one axial direction
  or a line light source array formed with a plurality of at least approximately parallel line spots formed to be narrow in an axial direction.

The axial direction of the narrow configuration is referred to as the transverse axis direction (q).

Moreover, this two-beam interferometer includes the following components:
  a light source objective following the line light source or the line light source array, for at least approximately imaging same in a diffraction-limited way,
  an objective imaging the object,
  a detector objective, wherein the objective imaging the object and the detector objective may also be formed as a single objective,
  a rasterized detector with receiver elements for electromagnetic radiation,
  and at least one digital computer with at least one evaluation program for detected interferograms for quickly obtaining information on the object.

According to the invention, in the reference arm
  either the line light source is formed to be so small in the transverse axis direction (q)

or the line spots of the line light source array are formed to be so small in the transverse axis direction (q) that for the following light source objective in this transverse axis direction (q), it is/they are at least approximately equal to or below the diffraction-limited lateral resolution thereof, which is determined by the numerical aperture of this light source objective and by the employed wavelength of light or by the employed wavelengths of light of the line light source or the line light source array.

There is an at least approximately diffraction-limited imaging of the line light source or the line spots of the line light source array onto the object by means of an objective. The Airy width in this imaging situation thus exceeds at least approximately that of the narrow-formed line light source, or the width of the narrow line spots is at least approximately made equal to this Airy width. The Airy width in this imaging situation results from the numerical aperture of the following imaging optical system and the wavelength used.

Moreover, according to the invention,
either a hybrid retro reference end reflector system is arranged in the reference arm R, said system being formed with a reference objective,
or a hybrid retro reference end reflector system is arranged, which is formed with an objective located outside the reference arm This hybrid retro reference end reflector system is respectively formed in combination with
either a hybrid retro reference micro end reflector array with hybrid retro reference micro end reflectors of the 90° roof edge mirror type or 90° roof edge prism type;
or a reference micro end reflector array with hybrid retro micro-reference end reflectors of the cylinder objective cat's eye type or of the cylinder mirror cat's eye type in the reference arm.

This hybrid retro reference end reflector system is respectively at least approximately arranged in the focal plane of the reference objective or of the objective located outside the reference arm.

In the hybrid retro reference end reflector system, there is a comparably small transverse offset delta_q of these hybrid retro micro reference end reflectors of the cylinder cat's eye type or of the 90° roof edge type at least approximately parallel to the direction of the transverse axis direction (q),
either in the focal plane (BER) of the reference objective (4 42) assigned to the hybrid retro reference end reflector
or in the focal plane (BER) of an objective located outside the reference arm, which objective is assigned both to the reference arm and to the object arm,
in the focal plane (F_91_r, F_9') upstream of the detector objective.

Thus, a transverse offset 2 delta_q_strich of mutually coherent light spots (A_r", A_o") from the reference and object arms is introduced.

The transverse offset delta_q of the hybrid retro micro reference end reflectors is made at most equal to or smaller than the tenth part of the focal length of the reference objective or the objective located outside the reference arm, and at least equal to or greater than the objective-based Airy disk radius for the main wavelength in the detected spatial interferogram.

The rasterized detector preferably has upstream optical means for introducing astigmatism into the detection optical path, which are assigned to or downstream of the objective for imaging the object.

Aspect 10.

In the following, the invention will be described for an assembly with an end reflector array in the reference arm of a two-beam interferometer.

The assembly is an assembly for robust one-shot interferometry, in particular also for spatial domain optical coherence tomography (SD-OCT), particularly for material measurement and also tumor cell detection. It can be used for distance measurement, in particular also for measurement in conjunction with a 3D-coordinates measuring machine, for two or three-dimensional profile measurement, roughness, waviness, and planeness measurement on technical and biological objects, there especially for tumor cell detection by detection of the 3D profile of cells, and for layer measurement.

To this end, a two-beam interferometer having reference and object arms, in particular also in the form of an interference microscope, is used. At least one end reflector is arranged in the reference arm. The two-beam interferometer is particularly formed in an open beam configuration and in particular also as a Michelson, Twyman-Green, Mirau, Linnik, Hybrid-Linnik, or Mach-Zehnder interferometer. The two-beam interferometer comprises the following components:
either at least one finely formed point light source
or a finely formed point light source matrix formed with a plurality of finely formed spots,
a light source objective following the light source, for at least approximately imaging same or the spots in a diffraction-limited way,
an objective imaging the object,
a detector objective, wherein the objective imaging the object and the detector objective may also be formed as a single objective,
a rasterized detector with receiver elements for electromagnetic radiation,
and at least one digital computer with at least one evaluation program for detected interferograms for quickly obtaining information on the object.

According to the invention,
in the reference arm, either the finely formed point light source is formed to be so fine,
or, in the reference arm, the spots of the finely formed point light source matrix are each formed to be so fine that for the following light source objective it is/they are at least approximately equal to or below the diffraction-limited lateral resolution thereof, which is determined by the numerical aperture of this light source objective and by the employed wavelength of light or by the employed wavelengths of the finely formed light source (198) or the finely formed point light source matrix.

By means of a full retro reference micro end reflector system with a reference objective and with full retro reference micro end reflectors respectively in
either a micro end reflector array with full retro micro reference end reflectors of the rotationally symmetric lens cat's eye type
or a micro end reflector array with full retro reference micro end reflectors of the rotationally symmetric mirror cat's eye type
or a triple prism mirror micro end reflector array with triple prism mirror micro end reflectors
or a concave triple mirror micro end reflector array with triple mirror micro end reflectors
arranged,
and in the micro end reflectors, respectively a transverse offset delta_q exists in the focal plane of the associated reference objective, said transverse offset being made at most equal to or smaller than the tenth part of the focal length of this reference objective and at least equal to or greater than the objective-based Airy disk radius for the main wavelength in the detected spatial interferogram.

In the focal plane upstream of the detector objective, there is a transverse offset 2 delta_q or 2 delta_q_strich of mutually coherent light spots (A_r", A_o") from the reference and object arms.

The rasterized detector preferably has upstream optical means for introducing astigmatism into the detection optical path, which are assigned to or downstream of the objective for imaging the object.

Further preferably, in an assembly for robust one-shot interferometry, the light source is formed as a multi-wavelength light source. This is a prerequisite for obtaining short-coherent interferograms (KKI).

Further preferably, in an assembly for robust one-shot interferometry, the light source is formed as a short-pulse light source. With pulse lengths in the nano, micro to millisecond range, it is possible to obtain short-coherent interferograms also on moving objects. Preferably, synchronization with the rasterized detector is performed.

Further preferably, in an assembly for robust one-shot interferometry, the light source is formed as a frequency comb light source. In this way, an unbalanced two-beam interferometer can be used for generating short-coherence interferences by balancing the optical path difference of the unbalanced two-beam interferometer by the optical delay length Y or by an integral multiple of the optical delay length Y of the frequency comb light source.

Further preferably, in an assembly for robust one-shot interferometry, the light source is formed as a tunable frequency comb light source. By means of fine-tuning of the frequency comb light source, a phase shift can be produced in two-beam interferograms in a predetermined way.

Further preferably, in an assembly for robust one-shot interferometry, the raster constant of rasterized light source and rasterized reference end reflectors, based on the focal plane of the tube objective or on the focal plane of the object-imaging objective, are at least approximately made equal.

Further preferably, in an assembly for robust one-shot interferometry, at least one micro end reflector array with full retro micro end reflectors of the mirror or lens cat's eye type is arranged, wherein each micro end reflector is laterally displaced by the transverse offset delta_q with respect to the object arm in the unfolded interferometer optical path.

Further preferably, in an assembly for robust one-shot interferometry, a measuring scanning raster in the form of a board of nails, which is determined by a rasterized point light source matrix, is arranged in a way rotated about an acute angle with respect to a flat detector, wherein the rotation of the point light source matrix is at least approximately around the optical axis of the optical assembly in the unfolded optical path.

Further preferably, in an assembly for robust one-shot interferometry, a "roof edge" (DK) of at least one 90° hollow roof edge reflector or the "roof edges" of a 90° hollow roof edge reflector array is/are arranged at least approximately in the plane BER and at least approximately parallel to the direction (lo) of the longitudinal extension of the line light source or the fine line spot of the line light source array. This "roof edge" must be in the wave-optical depth of field, which is a prerequisite for the function of the method.

Further preferably, in an assembly for robust one-shot interferometry, a "roof edge" (DK) of at least one 90° prism roof edge reflector or a 90° prism roof edge reflector array is imaged optically—taking into account the image offset v—at least approximately in the plane BER and at least approximately parallel to the direction (lo) of the longitudinal extension of the line light source or the fine line spots of the line light source array—viewed from the reference object in the reference space.

Further preferably, in an assembly for robust one-shot interferometry, a "roof edge" (DK) of a 90° hollow roof edge reflector is arranged in the plane FER at least approximately perpendicular to the direction lo and parallel to the direction q.

Further preferably, in an assembly for robust one-shot interferometry, a "roof edge" (DK) of at least one 90° prism roof edge reflector is imaged optically at least approximately in the plane FER—taking into account the image offset v—and at least approximately perpendicular to the direction lo and parallel to the direction q—viewed from the reference object. In this case, it is compulsory to use a frequency comb light source, preferably in the form of a frequency comb laser, for compensating for the optical path difference.

Further preferably, in an assembly for robust one-shot interferometry, the triple points (TP) of the triple hollow reflectors are arranged in a hollow triple reflector array, or the triple point of a single triple hollow reflector is arranged at least approximately in the plane BER. These triple points (TP) are preferably intended to be in the wave-optical depth of field.

Further preferably, in an assembly for robust one-shot interferometry, the triple points (TP) of the triple prism reflectors are arranged in a triple prism reflector array, or the triple point of a single triple prism reflector is imaged optically—taking into account the image offset v—at least approximately in the plane BER, viewed from the reference object.

Further preferably, in an assembly for robust one-shot interferometry, the focal point of a rotationally symmetric microlens in a full retro micro end reflector as part of a full micro end reflector is arranged at least approximately in the plane BER. All focal points of all rotationally symmetric microlenses in one full retro micro end reflector of a full micro end reflector are preferably intended to be in the plane BER.

Further preferably, in an assembly for robust one-shot interferometry, the focal points of the cylinder microlenses in a hybrid retro micro end reflector as part of a full micro end reflector are arranged at least approximately in the plane BER. All focal points of all microlenses in one full retro micro end reflector of a full micro end reflector are preferably intended to be in the plane BER.

Further preferably, means with variable refractive power for chromatic depth decomposition are arranged in the object arm. Thus, the wave-optically established depth measurement range can be increased substantially.

The inventive approach will be summarized in the following:

It relates to a method and an assembly for robust one-shot interferometry, in particular for spatial domain optical coherence tomography (SD-OCT), on material and living tissue, for distance measurement, particularly also for measurements in a measuring machine, for 2D or 3D profile measurement on technical and biological objects, particularly also for tumor cell detection by means of detection of the geometric cell profile on tissue surfaces and measurements in the near surface region, with a finely structured light source imaged onto the object in a diffraction-limited way, with an interferometer having object and reference arms as well as with a detector for electromagnetic radiation. Either at least one hybrid retro reference end reflector or an array of hybrid retro reference end reflectors or an array of full retro reference end reflectors for generating tilted wavefronts is arranged in the reference arm. After transfer optical system is passed by the interfering bundles, spatial interferograms with mutually inclined reference and object wavefronts form during the detection, said interferograms being detected for determining distance, profile, or optical path length in a detector frame, and being evaluated by means of digital computer and computer program.

In another approach, in the reference arm, reference light is defocused in the reference arm of the two-beam interferometer, wherein in the latter the light-field approach is employed. In the detection, spatial interferograms with ring-shaped interference stripes are formed by differently curved reference and object wavefronts of each detected object point, which are detected for determining distance, profile, or optical path length in a detector frame and are evaluated by means of digital computer and computer program.

Both approaches may be combined with each other.

The measuring system is formed with a finely structured radiation source imaged onto the object in a diffraction-limited way at least in one dimension, said radiation source being preferably formed as a fine line source and preferably as a short-pulse short-coherence light source, wherein, by definition, its longitudinal direction is formed in the direction of the y axis, preferably with a sub-spectral range that may extend from the EUV to the terahertz range, and this radiation source is preferably short-coherent.

The rasterized detector for electromagnetic radiation is preferably sensitive in a spectral subrange that may extend from the EUV to the terahertz range.

In the reference arm, either at least one hybrid retro reference end reflector, preferably in the form of a roof edge reflector, both for generating one or more tilted reference wavefronts and a wavefront inversion compensation either is inclined about its tilt-sensitive axis or there is a lateral offset of said at least one roof edge reflector in connection with an objective in the reference arm, so that lateral shear is generated. Moreover, one-dimensional retro end reflectors in the form of arrays may be formed as well. In all cases—after subsequent passage of transfer optical system by the interfering bundles with preferably confocal discrimination of object radiation—at least one spatial two-beam interferogram with mutually inclined reference and object wavefronts forms during the detection, said interferogram being detected for determining distance, depth, profile, or the optical path in a single detector frame and being evaluated by means of digital computing technology.

A one-dimensional retro end reflector is also referred to as a hybrid retro reflector. A hybrid retro reflector either has a "roof edge"—in the case of a roof edge reflector—or a cylinder axis—in the case of a cylinder cat's eye reflector. Both the roof edge (DK) and a line parallel to the cylinder axis ZA, which includes the reflection plane in a model-like way, will in general be referred to as the DK line (DKL) of the hybrid retro reflector in the following.

The one-dimensional retro end reflector in the reference arm, when a focusing objective imaging the object is arranged in the object arm but no focusing objective is arranged in the reference arm, is located with its DK line (DKL) perpendicular to the longitudinal direction lo of the line light source.

The one-dimensional retro end reflector in the reference arm, when a focusing objective is arranged both in the object arm and in the reference arm, is located with its DK line (DKL) parallel to the longitudinal direction lo of the line light source.

Aspect 13.

In the following, the invention will be described for a measuring method with an end reflector in the reference arm of a two-beam interferometer according to the light-field approach.

The method is a method for robust one-shot interferometry, in particular also for optical coherence tomography according to the spatial domain approach (SD-OCT) and particularly also according to the light-field approach, particularly for material measurement and also tumor cell detection. It can be used for distance measurement, in particular also for measurement in conjunction with a 3D-coordinates measuring machine, for two or three-dimensional profile measurement, roughness, waviness, and planeness measurement on technical and biological objects, there especially for tumor cell detection by detection of the 3D profile of cells, and for layer measurement.

To this end, a two-beam interferometer having reference and object arms, in particular also in the form of an interference microscope, is used. At least one end reflector is arranged in the reference arm. The two-beam interferometer is particularly formed in an open beam configuration and in particular also as a Michelson, Twyman-Green, Mirau, Linnik, Hybrid-Linnik, Mach-Zehnder interferometer or also as a multi-channel interferometer arrangement. The two-beam interferometer comprises the following components:

- either at least one finely formed point light source
- or a finely formed point light source matrix formed with a plurality of finely formed spots,
- at least one light source objective following the light source, for at least approximately imaging same or the spots in a diffraction-limited way,
- at least one objective imaging the object,
- at least one detector objective, wherein the objective imaging the object and the detector objective may also be formed as a single objective,
- at least one rasterized detector with receiver elements for electromagnetic radiation,
- and at least one digital computer with an evaluation program for detected interferograms for quickly obtaining information on the object.

According to the invention,

- either the finely formed point light source is formed to be so fine
- or the spots of the finely formed point light source matrix are each formed to be so fine
- that for the following light source objective it is/they are at least approximately equal to or below the diffraction-limited lateral resolution thereof, which is determined by the numerical aperture of this light source objective and by the employed wavelength of light or by the employed wavelengths of the finely formed light source or the finely formed point light source matrix.

Here, object points of the object are illuminated with optical means

- in the case of optically rough objects, with at least approximately diffraction-limited sharply focused image points of the point light source or the finely formed point light source matrix
- or in the case of optically smooth objects, with slightly defocused image points of the point light source or the finely formed point light source matrix.

After beam unification, geometrically-optically defocused imaging of these illuminated object points onto the detector is performed with optical means, and light from each object point illuminates a subregion with a plurality of detector elements of the rasterized detector. In the reference arm R, geometrically-optically defocused imaging of points of the point light source or the finely formed point light source matrix is performed with optical means, and light from each luminous point of the point light source or the finely formed point light source matrix illuminates a subregion with a plurality of elements of the rasterized detector after beam unification. The subregion surfaces on the rasterized detector of mutually coherent beam bundles from O and R are at least approximately made to overlap. Further, at least one spatial interferogram of coherent radiation from reference arm R and object arm O is formed, wherein the interference area in the lateral extension is at least 30% of the maximum extension of the two subregion surfaces.

At the output of the two-beam interferometer, in the space behind the tube objective
or an at least approximately focusing objective from the illuminating optical path, which is also used for detection
both image points A_r" from the point light source or the finely formed point light source matrix, which are imaged via the reference arm R,
and image points A_o" from the point light source or the finely formed point light source matrix, which are imaged via the object arm O,
are at least approximately sharply imaged in a diffraction-limited way in the case of optically rough objects
or are imaged in a slightly defocused way in the case of optically smooth objects.
formed in a way separated from each other at least in depth.

The depth separation def_r-o has the following minimum amount:
Half the main wavelength (lambda_S) in the detected signal of the spatial interferogram divided
by the square of the effectively used numerical aperture
either of the tube objective
or of the at least approximately focusing objective
or of the at least approximately focusing objective from the illumination optical path, which is also used for detection.

The maximum of this amount def_r-o is equal to the focal length
either of the tube objective
or of the at least approximately focusing objective
or of the at least approximately focusing objective from the illumination optical path, which is also used for detection.

In the case of optically smooth, aspherical surfaces slightly outside the wave-optical depth of field of the objective in the object arm of a Linnik interferometer, which comprises a light source in the form of a point matrix, there might be some astigmatism in the object bundles behind the tube objective, so that no sharp spots can form in the detection optical path. Nevertheless, in the case of a comparably small offset of the illuminating spots from the objective focal plane on the object surface, it is still possible to detect and evaluate light-field interferograms in the object arm of a Linnik interferometer in the detection optical path behind a microlens array.

Aspect 14:
Further preferably, in the method for robust one-shot interferometry according to the above aspect 13, the depth separation def_r-o_strich of foci A_r", A_o" of light from the reference arm R and the object arm O in the detection optical path, in the case of an at least approximately equal optical path length in the two arms of the two-beam interferometer
is either provided in a predetermined way by using slightly different travel paths in different optical media in the reference and object arms of the two-beam interferometer
or is provided in a predetermined way by separation of the foci in the detection optical path by forming slightly defocused spots in the reference arm on the end reflector.

Aspect 15:
Further preferably, in the method for robust one-shot interferometry (such as in the method according to aspect 13 and/or 14), prior to detection, beam shaping is performed with elements of positive or negative refractive power of an array having focal planes thereof at least approximately in a common plane, and these focal planes coincide with the detection plane of the rasterized detector or are made optically conjugated thereto by means of an optical transfer stage.

The elements of positive negative refractive power of an array constitute an optical Fourier transform. An object point-wise/measurement point-wise Fourier transform is performed and an areal spatial interferogram is formed, which may also be referred to as a light-field interferogram. It is detected with a plurality of pixels by the rasterized detector. If Schwarzschild objectives are used, the construction-related center shading is not disturbing since enough pixels are illuminated and redundancy is provided in the spatial interferogram.

In addition to defocusing, it is possible to introduce lateral shear in the way described. This can yield unambiguity as to the depth location of an object point for specific arrangements, in particular if light having a large coherence length is used. This is an approach with carrier frequency, which may be optimally adapted.

Aspect 16:
Further preferably, in the method for robust one-shot interferometry (such as in the method according to one or more of the aspects 13 to 15), the ring ordinal number is determined from the spherical component in the spatial interferogram. This allows using long-coherent light sources, such as that of a HeNe laser for absolute shape measurement.

By separation of the foci in the detection optical path in a lateral manner or in depth, it is also possible to block out reference foci in the detection optical path in a predetermined way in the approaches described here. Thereby, it is possible to detect also the angular spectrum of the object light in a measurement point-wise way without influence by the reference light, which in the case of little cooperative objects can help obtaining further information on the object. Here, the detection of the object light angular spectrum is preferably performed in a separated, comparably small spectral channel or in several, comparably small spectral channels in order to be able to obtain short-coherence two-beam interferograms for the measurement points by means of remaining spectral channels with two-beam interferences. Coupling out of the object light for the angular spectrum may be performed by means of micro-apertures or micro-reflectors. For example, if the red component of the reference light is blocked, the observation may take place in the red channel of a color or hyper-spectral camera. Also, the simultaneous observation of the object light propagation in depth, without the reference light being present to a noticeable extent, after focusing of the object light and simultaneous detection in different discrete depths is basically available in these approaches with separation of foci. This can be used to also adopt phase retrieval methods.

Aspect 17:

Aspect 17 relates to an assembly for robust one-shot interferometry, in particular also for optical coherence tomography according to the spatial domain approach (SD-OCT) and particularly also according to the light-field approach, particularly for material measurement and also tumor cell detection, for distance measurement, in particular also for measurement in conjunction with a 3D-coordinates measuring machine, for two or three-dimensional profile measurement, roughness, waviness, and planeness measurement on technical and biological objects, there especially for tumor cell detection by detection of the 3D profile of cells, and for layer measurement, and to this end, a two-beam interferometer having reference and object arms, in particular also in the form of an interference microscope, wherein at least one end reflector is arranged in the reference arm, in particular formed in an open beam configuration and in particular also as a Michelson, modified Michelson, Twyman-Green, Mirau, Linnik, Hybrid-Linnik, Mach-Zehnder interferometer or also as a multi-channel interferometer arrangement, comprising the following components:
  either at least one finely formed point light source
  or a finely formed point light source matrix formed with a plurality of finely formed spots,
  at least one light source objective following the light source, for at least approximately imaging same or the spots in a diffraction-limited way,
  at least one objective imaging the object,
  at least one detector objective, wherein the objective imaging the object and the detector objective may also be formed as a single objective,
  at least one rasterized detector with receiver elements for electromagnetic radiation,
  and at least one digital computer with an evaluation program for detected interferograms for quickly obtaining information on the object.

According to the invention,
  either the finely formed point light source is formed to be so fine
  or the spots of the finely formed point light source matrix are each formed to be so fine
  that for the following light source objective it is/they are at least approximately equal to or below the diffraction-limited lateral resolution thereof, which is determined by the numerical aperture of this light source objective and by the employed wavelength of light or by the employed wavelengths of the finely formed light source or the finely formed point light source matrix.

In the two-beam interferometer there is slight asymmetry caused
  either by different travel paths of the light in different materials of different refractive power
  and/or by refractive powers of optical components, which are distributed unevenly in the two interferometer arms R and O
  and/or by components with refractive power positioned unevenly in the depth of the two interferometer arms.

Moreover, either
  in the space behind the tube objective
  or an at least approximately focusing objective
  or the at least approximately focusing objective from the illuminating optical path, which is also used for detection there are two separated focal planes in depth, which are at least approximately separated from each other by an amount Def_strich in a predetermined way.

The amount Def_strich represents an apparatus constant fixedly set by optical system design, construction, assembly and also apparatus adjustment. This amount Def_strich is made at least or greater than
  half the main wavelength lambda_S in the detected signal of spatial interferograms divided
  by the square of the effectively used numerical aperture of the tube objective
    or of the at least approximately focusing objective
    or of the at least approximately focusing objective from the illumination optical path, which is also used for detection.

Moreover, this amount Def_strich is made smaller than the focal length
  of the tube objective
  or of the at least approximately focusing objective
  or of the at least approximately focusing objective from the illumination optical path, which is also used for detection.

However, it is also possible to operate a strongly unbalanced interferometer—i.e. with an optical path difference significantly different to zero—with a frequency comb radiation source in order to be able to generate short-coherence interferograms. Here, the components in the two interferometer arms R and O can be formed as refractive, reflective, or also mirror lens components. Preferably, structurally similar components are used in the reference arm R and in the object arm O. Preferably, different components are used in the reference arm R and in the object arm O.

Aspect 18:

Moreover, in the assembly for robust one-shot interferometry (such as in the assembly according to aspect 17), in the image plane of the two-beam interferometer, an optical array with elements of positive or negative refractive power is arranged in the style of a light-field camera or plenoptic camera, and each pair consisting of a diffraction-limited image spot from the reference arm R and the object arm O, which each represent coherent spots, is assigned at least one of these elements of positive or negative refractive power.

Preferably, a microlens array or an array of micromirrors with positive or negative refractive power is arranged.

Aspect 19:

Moreover, in the assembly for robust one-shot interferometry (such as in the assembly according to aspect 17 and/or aspect 18), the optical array with elements of positive or negative refractive power is formed to be at least approximately slightly curved. "Slightly curved" means that the elements of positive or negative refractive power (with their pupil centers) are at least approximately located on a spherical shell having a spherical shell radius of greater than/equal to (at least equal to) the focal length of the associated tube objective.

This serves for adaptation to the residual image field curvature of a tube objective. Preferably, it is also possible that the respective focal length of the elements of positive or negative refractive power is adapted to this residual image field curvature. This allows generating at least approximately plane reference waves on a detector, whereby, on the one hand, undesired crosstalk by a partial overlap of adjacent interference fields on the detector is minimized and, on the other hand, the detector area is used to the best possible extent.

Further, in the assembly for robust one-shot interferometry, the focal length of the elements of positive or negative refractive power in the array corresponds at least approximately to the predetermined depth separation Def_strich.

Aspect 20:

Moreover, in the assembly for robust one-shot interferometry (such as in the assembly according to one or more of the aspects 17 to 19), the focused object image spots A_o" are located at least approximately in the pupil of the elements of positive or negative refractive power in the array.

Aspect 21:

Moreover, in the assembly for robust one-shot interferometry (such as in the assembly according to one or more of the aspects 17 to 20), there is at least approximately the optical path difference of zero in the two-beam interferometer. Thus, it is possible to use a light source with a small coherence length.

Aspect 22:

Moreover, in the assembly for robust one-shot interferometry (such as in the assembly according to one or more of the aspects 17 to 20), the microlens array in the detection optical path is formed with diffractive optical elements, DOEs, on the basis of a switchable spatial light modulator.

Thus, if a switchable spatial light modulator as the first array for the point light source is used, which is part of a pulsed light source, it is possible to perform a strict temporal and spatial synchronization to this second array in the detection optical path in order to be able to quickly laterally scan the object with a sequence of pulsed illuminations which each are slightly offset laterally. Here, the diffractive optical elements, which preferably represent Fresnel lenses of positive or negative refractive power, wherein only one diffraction order is used, preferably remain at least approximately centered to the focused light spot pairs from the two-beam interferometer. These are preferably spatial interferograms, also referred to as light-field interferograms here, which can be evaluated entirely separate from each other. The detector frames with spatial interferograms, which have been recorded several times, increase the density of the measurement points on the object and can be united in a data set by means of suitable algorithms, so that 3D information on the object as complete as possible—in conformity with the measuring task—can be obtained.

The array, preferably a microlens array, in the detection optical path may also be formed as an array with refractive lenses, which are made to follow up, or track, the lateral movement of point light sources between the individual exposures by a lateral scanner.

In the case of optically rough surfaces, the measurement object or the detecting measurement points needs to be at least approximately in the wave-optical depth of field, also referred to as depth of view (DOV), in order to obtain an interference contrast sufficiently high for the interferogram evaluation.

By contrast, in this approach for light-field interferometry, it is also possible to detect objects having smooth and uniform surfaces that are outside the wave-optical depth of field of optical scanning, provided that the coherence length of the light used is made sufficiently great. On this condition, spatial interferograms can be observed and detected in this case. Thus, this is also an approach for measuring aspheres on the basis of a Michelson interferometer in a Twyman-Green assembly or, in the case of micro-spheres or in subregions of aspheres with rather greater gradients, also on the basis of a modified Mirau or a modified Linnik interferometer according to the light-field interferometer approach. For this application, it may make sense to limit the number of light spots, for example to 30×30 in a matrix point light source with adapted temporal coherence of the radiation used. In addition to the depth information, the light-field interferograms also provide information on the gradient of the object. This may be very advantageous to the evaluation, particularly in the measurement of aspheres.

In selected cases, it may be advantageous to use a Fizeau interferometer with the light-field approach. To this end, as described by J. Schwider in "Multiple beam Fizeau interferometer with filtered frequency comb illumination", Opt. Comm. 282 3308-3324 (2009), a frequency comb light source can be used in order to bridge, or accommodate, the optical path difference always present in the Fizeau interferometer.

To obtain the angular spectrum of measurement points on the object in real time in the case of interferometers with asymmetry, due to the occurring focus position differences between beam bundles from the reference arm and from the object arm in the detection optical path, it is further possible to permanently arrange a spectral band stop filter matrix of microspot diaphragms in the raster of the reference foci on a thin substrate, which all bundles from R and O pass together. This matrix of microspot diaphragms blocks the foci in a spectral range. This is done preferably in the blue spectral range. An RGB color camera or a color camera system detects the spatial interferences only in the green and red ranges, and only object light in the blue spectral range, since here the associated reference light has been blocked. For each measurement point, a range of the angular spectrum is reserved on the rasterized detector in the blue spectral range preferably by using a transfer optical system, so that the angular spectra are detected in parallel with the spatial interferences. The angular spectrum of separated object light is preferably detected in the Fourier plane of an objective or a microlens array.

Moreover, object light can be observed simultaneously in an object point-wise manner in different depths in order to be able to apply the phase retrieval method.

Preferably, due to a comparably small asymmetry in the optical path of the two-beam interferometer, it is further achieved that for an angle in the middle range of the angular spectrum the optical path difference in the detection plane is zero. In a Mirau interferometer having a plate beam splitter consisting of splitter and compensation plate made of the same material, the geometric path length is made different in the range from 5 µm to 50 µm. For example, for this approach, a difference of 10 µm or 20 µm can typically be sufficient. It is also possible to generate a chirped short-coherence interferogram (chirped white light) in a targeted manner, with geometric path length differences in the range of up to 100 µm at most, which may be completely different depending on the spectral range and the material dispersion. The result is a chirped short-coherence interferogram having asymmetry that is deliberately intended. The asymmetry is that the two first-order stripes have strongly different intensity maxima. There is a strong deviation on the one side of the short-coherence wavelet—i.e. between zero-order stripes and one of first order), and a small deviation on the other side of this wavelet. The location of half the deviation can advantageously be determined for the z position of an object point. This is not the exact location of the optical path different equal to zero, but does represent a very good reference. This is usually an acceptable offset, which for common measurement objects should have an at least approximately equal value far in the submicrometer range.

In a Linnik interferometer, preferably small focusing error is introduced into the reference arm. The optical path difference can be set to a value by finely shifting the entire end reflector in the reference arm, so that the optical path difference results in the detection plane for a beam inclination at least approximately in the middle of the angular range of the angular spectrum. For a Linnik interferometer, this can be adjusted comparably easily in the reference arm as a combination of defocusing and shift of the end reflector system with objective. This does not require very tight component tolerances, such as in the case of a Mirau interferometer, with respect to plate thickness. There, the only possibility to accomplish the adjustment of the optical path difference of zero at a suitable point is via the difference of the plate thickness of splitter and compensation plates and the depth location (z) of the plane reference mirror or also via the introduction of weak refractive power by introducing a surface curvature on the beam splitter system. Shifting of the end reflector system with objective usually produces a small spherical phase component by interferences of the same inclination, which is comparably easy to correct numerically though.

In another approach for one-dimensional profile measurement, roughness, waviness, and planeness measurement, or for optical coherence tomography (OCT) on technical and biological objects with a two-beam interferometer on the basis of a Michelson interferometer, which comprises an object-imaging measuring objective in the object arm, the end mirror is preferably formed as a slightly curved mirror. This approach works with a point light source at least approximately located on the optical axis of the object-imaging measuring objective. The use of a fine point light source is necessary since there is a centrosymmetric wavefront inversion in the interference. Preferably, this end mirror is arranged in the reference arm R of the two-beam interferometer at a distance from the beam, which also results in an optical path difference of zero on the rasterized detector. Thus, if a spectrally broadband light source is used, short-coherence interferograms can be detected. For optical components between light source and detector with sufficiently small aberrations, ring-shaped interferences can be observed in the detection plane.

Preferably, the end mirror is formed as a slightly curved concave mirror in the reference arm R of the two-beam interferometer. Preferably, its focal length is such that behind the tube objective the resulting focus spot A_r" is in the front focal plane of a microlens. Behind it there forms a plane reference wave for interference with coherent light with a curved wavefront from an object point A_o, detected in the wave-optical depth of field, in the Fourier plane of the microlens. Since ring-shaped interferences are observed here, the center shading in the case of a Schwarzschild mirror objective is of no disadvantage, since the two-beam interferometer can be adjusted such that the interference rings are detected with the zero-order interference ring in the remaining circular ring.

To compensate for the optical path difference in the two-beam interferometer, which exists when the curved mirror is arranged in a position that does not lead to an optical path difference of zero, a laser with a sufficiently great coherence length is preferably used. Short-coherent interferograms do not occur in this case. In order to be able to also detect short-coherence interferences, use is preferably made of a frequency comb light source, which compensates for this optical path difference in the two-beam interferometer in a known manner, so that short-coherence interferograms can be detected.

The chromatic residual aberrations, in particular the chromatic longitudinal aberrations, which occur in a two-beam interferometer with a spectrally broadband light source and which are nearly unavoidable, can preferably be used to generate a short-coherence interferogram with a moderate predetermined, comparably tightly tolerated chirping, which results in an asymmetric intensity wavelet. Chirping is preferably set such in the signal that between the absolute maximum short-coherence interferogram and a first minor maximum there is a largest possible intensity deviation on one side, which e.g. in the case of a sufficient spectral bandwidth of the detected light and the appropriate chirping may well be 50% of the intensity maximum in the short-coherence interferogram. Here, there is preferably a difference of the travel paths in refractive materials above the refractive index 1.4 for object light and reference light of up to maximally 100 µm in the two-beam interferometer in the visible and near-infrared range. In the material BK7, for example, a travel path difference in the two interferometer optical paths in the lower two-digit micrometer range is sufficient in the visible spectral range in order to achieve noticeable asymmetry in the short-coherence interferogram wavelet, which then requires a special signal evaluation though. To this end, preferably, a moving trigger threshold can numerically be set on half the value of the intensity deviation. The use of refractive microlenses in an array for light-field interferometry can also cause chirping, since object light and reference light usually go separate ways through the microlens or have different beam incidence angles on the microlens surface.

For chirped spatial interferograms, it is preferably possible to numerically set a high-precision trigger point on the long edge between the zeroth stripe and the smaller intensity maximum of a first-order stripe in the case of a sufficiently broad spectral range.

Additional Description of FIGS. 1-76

The invention is described by way of example with reference to FIGS. 1 to 76.

The term light is always used herein as a synonym for electromagnetic radiation from the terahertz through infrared to EUV spectrum.

FIG. 1 illustrates an OCT sensor, measuring in a line-like way, on the basis of a one-shot interferometer on the basis of a modified interferometer of the Linnik type, having a focusing objective 6 in the object arm, which is also intended to be used for measuring skin on a human being. FIG. 1 illustrates the approach of moving the entire measuring head.

The pulsed light source 1 is formed by a superluminescence diode battery with downstream and quickly rotating slot chopper wheel having high-precision speed control and rotational angle control by a digital computer. The slot width on the wheel is relatively approximately 40% of the average slot intervals. In this way, a pulsed line light source illuminating a downstream fixed slit is provided, the longitudinal axis of the slit facing in the y direction. The width of the slit is 5 µm and the illuminated length is 5 mm.

The most important parameters of the pulsed line source 1 are:

Line source in NIR with 800 nm to 900 nm center wavelength, with a pulse rate of 400 Hz and an average pulse time of 100 µm (40% relative switch-on time, trapezoidal shape, lights comes from chopper), coherence length 6 µm, continuous-wave performance of a superluminescence diode battery: 20 mW.

The sensor head moves with 1 mm/s in the depth direction across a depth range of 500 µm in the line direction (z direction).

The light coming from the pulsed short-coherent light source 1 is detected and collimated by a collimator objective 2, operating in a diffraction-limited way, with half the aperture angle alpha_y_source, which yields a numeral aperture of 0.1. The collimated light reaches a beam splitter 3 in the interferometer. The width b_spot is below the diffraction-limited lateral resolution of the collimator objective 2. The interferometer operates at least approximately at the optical path difference of zero. In the reference arm, the reflected light reaches a diffraction-limited Schwarzschild objective 4 with a roof edge reflector 561, with the roof edge thereof in the focal plane. The roof edge reflector 561 has a transverse offset delta_q. The radiated light is offset transversely and is subjected to a mirror symmetric wavefront inversion and, after passing the Schwarzschild objective 4, is incident on the beam splitter 3 again in an inclined way, where it transmits and enters the detection optical path. In the object arm O, the transmitted light is incident on a diffraction-limited Schwarzschild objective 6 having a numerical aperture of 0.25.

The light coming from the beam splitter 3 is focused onto the human skin 71 in line form in a diffraction-limited way and reflected in a scattered way by means of the Schwarzschild objective 6. The depth range of the mechanically moved sensor head is 500 μm in this case, so that also focused light can enter the human skin 71, where it is scattered and propagates toward the Schwarzschild objective 6. This Schwarzschild objective 6 detects the light returning from the human skin 71 and guides it toward the beam splitter 3, where it is reflected into the detection optical path. Located in the detection optical path is an astigmatic imaging system 8 with a slit diaphragm 9 for the confocal discrimination of the object light, with two rotationally symmetric objectives 10 and 11 and a cylinder objective 12 with lying cylinder axis for forming cylinder waves on the camera chip 13 of the digital camera. This digital camera is operated at 400 Hz. The associated digital computer determines the temporal clock and forces the strictly synchronized motion of the quickly rotating slot chopper wheel with high-precision speed control and rotational angle control.

On the digital camera, from each focusing measurement point in or on the human skin 71, a focused cylinder wave comes onto the digital camera, which is made to interfere with a focused reference cylinder wave from the reference arm, which is inclined toward the object cylinder wave. In this way, a spatial, line-like interferogram KKI forms along a line of the camera chip 13 for each individual measurement point. The line-like interferogram KKI is detected with 256 pixels per detected measurement point. The camera chip 13 has a frame rate of 400 Hz. Thus, in 1024 columns, 1024 measurement points are detected in line in the measuring space where the human skin 71 is located. Each measurement point has an associated interferogram KKI, so that a maximum of 1024 interferograms KKI can be detected in a single camera frame as one-shot interferograms.

Per 5 μm depth value of focusing, a camera image is captured on average, wherein the blur by the pulse illumination with 100 μs of duration is less than 0.1 μm in depth. The optical path difference between the interfering wavefronts changes by the short pulse with 100 μs of average pulse time in trapezoid-triangle form by about 0.2 μm, which for the wavelengths in the NIR leads to an effective phase change in the interferogram of less than Pi/2. This is well acceptable as regards the contrast of the interferograms averaged with respect to time.

With this system, it is possible to perform a depth scan (A scan) with 460 μm of detected measuring depth and 1024 laterally detected measurement points per 100 ms. Here, a lateral spatial resolution of 2 μm and a resolution of 5 μm in depth are assumed.

The evaluation of the spatial interferograms, the spatial frequency of which is at least approximately known, is performed by means of methods known in white-light interferometry, which yield the 3D OCT data set of the detected skin.

Figure 2:
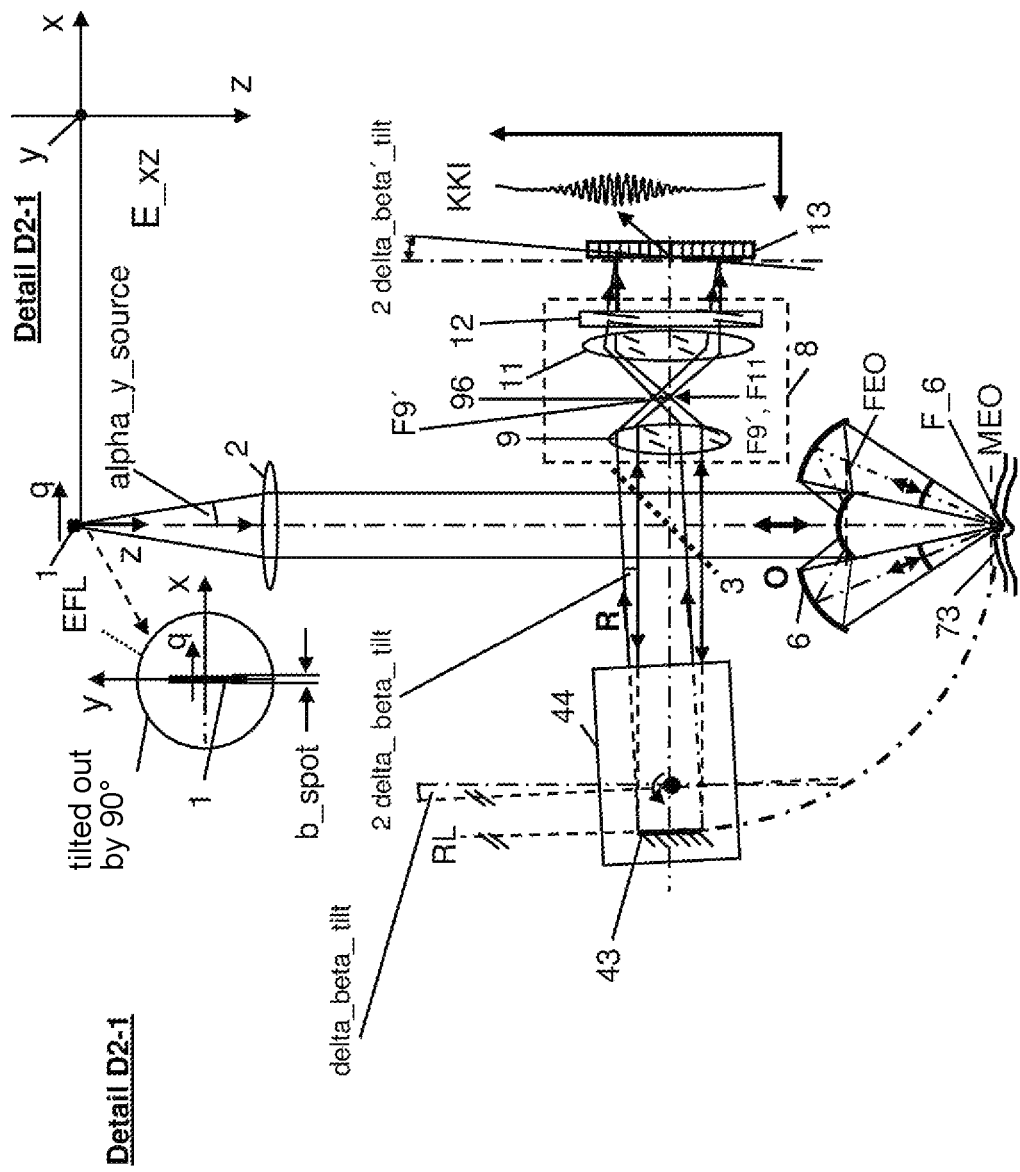
FIG. 2 illustrates a further exemplary OCT sensor, measuring in a line-like way, on the basis of a one-shot interferometer in accordance with one or more aspects of the present disclosure.
Figure 8:
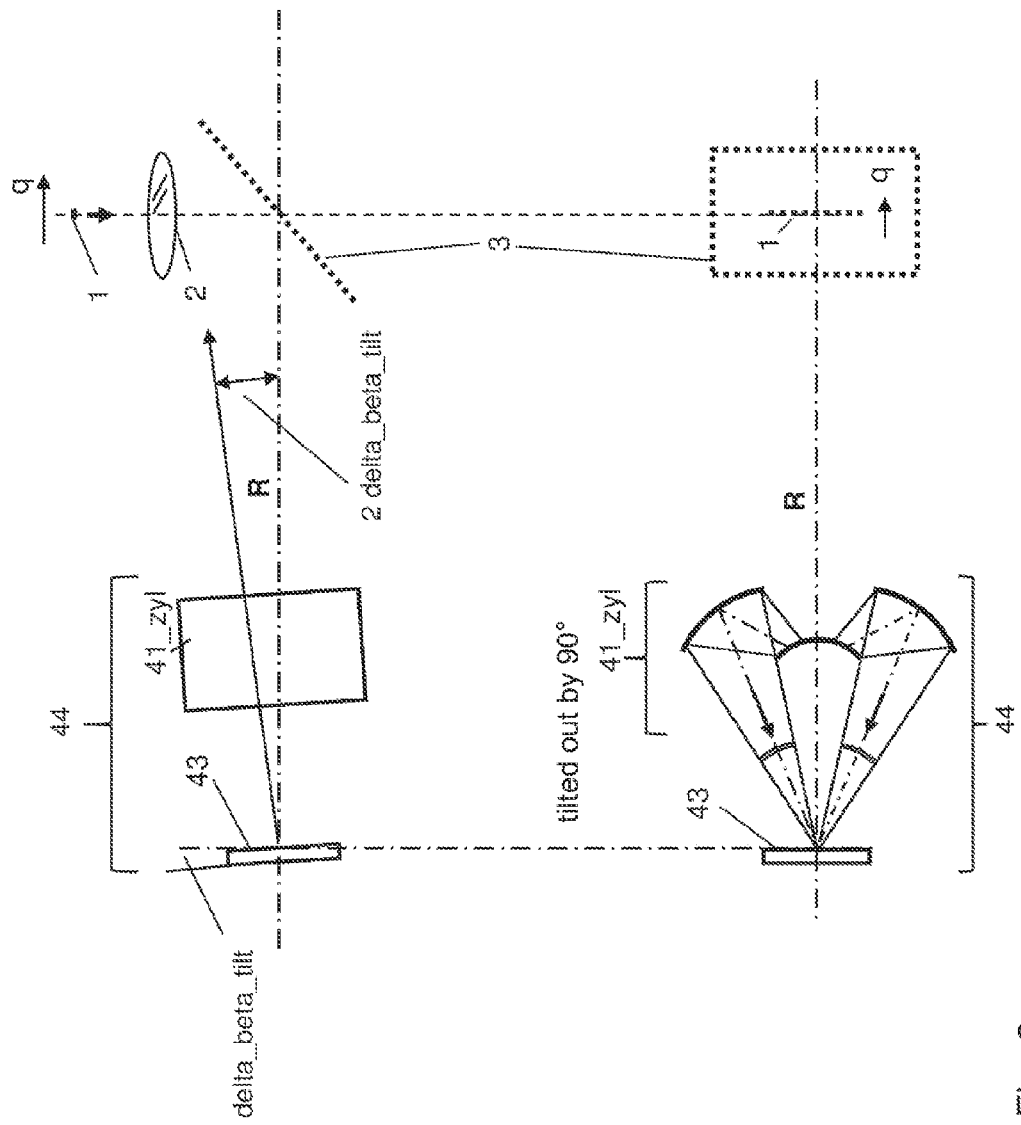
FIG. 8 illustrates an exemplary unfolded reference arm in accordance with one or more aspects of the present disclosure.

FIG. 2 illustrates an OCT sensor, measuring in a line-like way, on the basis of a one-shot interferometer on the basis of a modified interferometer of the Linnik type, having a focusing Schwarzschild objective 6 in the object arm, which is also intended to be used for measuring skin on a human being. A cylinder mirror hybrid retro reference end reflector 44 is inserted in the reference arm, with a cylinder mirror objective 41 as can be seen in FIG. 8. Here, its cylinder objective axis (CA) is perpendicular to the longitudinal direction lo of the line source 1. The tilt axis of the cylinder mirror hybrid retro reference end reflector 44 is at least approximately parallel to the y axis. The rotationally symmetric tube objective 9 images at least approximately the Fourier plane FEO of the Schwarzschild objective 6 in the plane of the rasterized detector 13. By means of an astigmatic imaging stage 8 with the cylinder objective 12, elongated and mutually laterally separated short-coherence interferograms KKIs form in the plane of the rasterized detector 13. The detail A represents the light source plane, tilted out by 90°, with the width b of the fine line light source 1.

Figure 3:
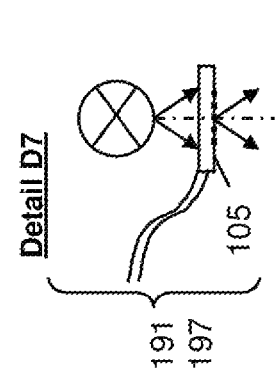
FIG. 3 illustrates an exemplary light source-related coordinate system in accordance with one or more aspects of the present disclosure.

With regard to FIG. 3: It illustrates a light source-based coordinate system in which the longitudinal direction of the light source, here a fine light slit 196, represents the y axis and the direction of the minimum extension of the light source represents the x axis. The azimuthal position of the fine light slit 196 may be arbitrary. The end reflector components in the reference arm are to be geared thereto. In the x direction or transverse direction q, the extension of the fine light slit 196 is below the lateral resolution provided by the diffraction limitation of the numerical aperture NA of the following collimator objective 2 and the light spectrum used.

Figure 4:
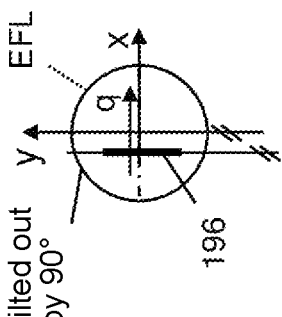
FIG. 4 illustrates an exemplary fine light slit arranged in a laterally offset manner in accordance with one or more aspects of the present disclosure.

FIG. 4 illustrates a fine light slit 196 arranged in a laterally offset manner. End reflector components in the reference arm are to be geared thereto. At least in the transverse direction q is the extension of the fine light slit 196 at or below the lateral resolution provided by the diffraction limitation of the numerical aperture NA of the following collimator objective 2 and the light spectrum used.

Figure 5:
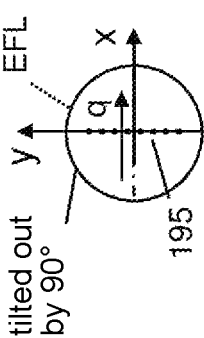
FIG. 5 illustrates an exemplary fine point light source in chain form in accordance with one or more aspects of the present disclosure.

FIG. 5 illustrates a fine point light source in chain form 195. At least in the transverse direction q is the extension of the fine points of the point light source in chain form 195 at or below the lateral resolution provided by the diffraction limitation due to the numerical aperture NA of the following collimator objective 2 and the light spectrum used.

Figure 6:
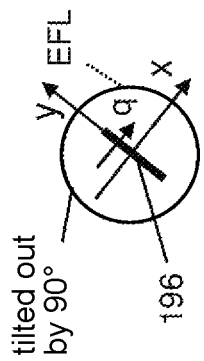
FIG. 6 illustrates an exemplary finely formed point light source matrix in accordance with one or more aspects of the present disclosure.

FIG. 6 illustrates a finely formed point light source matrix. At least in the transverse direction q is the lateral extension of the individual light spots at or below the lateral resolution provided by the diffraction limitation due to the numerical aperture NA of the following collimator objective 2 and the light spectrum used.

Figure 7:
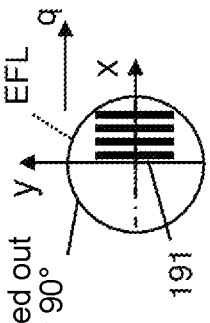
FIG. 7 illustrates an exemplary fine line light source in accordance with one or more aspects of the present disclosure.

FIG. 7 illustrates a fine line light source formed by means of computer-controlled spatial light modulator in transmission on liquid crystal-basis and upstream short-coherent light source, which is not illustrated here. The addressed line-like transmission regions can be shifted in a computer-controlled way in order to be able to detect a measurement field almost over the entire area in the detection process. In the transverse direction q, the extension of the individual light spots is at or below the lateral resolution provided by the diffraction limitation due to the numerical aperture NA of the following collimator objective 2 and the light spectrum used.

FIG. 8 illustrates an unfolded reference arm R in which a cylinder mirror hybrid retro reference end reflector (ZSHRRER) 44 with cylinder mirror objective 41 is located. The cylinder objective axis (CA) of the cylinder mirror objective 41 is oriented perpendicular to the longitudinal direction lo of the line source 1. The entire cylinder mirror hybrid retro reference end reflector 44 is tilted slighted by the angle delta_beta_tilt, so that the tilt angle 2 delta_beta_tilt exists for reference bundles.

FIGS. 9 to 12 describe possible hybrid retro reference end reflector assemblies. FIG. 9 illustrates a tilted roof edge reflector 5. FIG. 10 illustrates a roof edge reflector 5 with the roof edge DK in the reference arm.

FIG. 11 illustrates the reference optical path in the reference arm R in a modified Linnik interferometer with a rotationally symmetric reference objective 42 and a hollow 90° roof edge end reflector 561. The fine line light source 1 has a width b. The roof edge mirror reflector 561 does not necessarily have a tight tolerance of the 90° roof edge angle. For illumination, the interferometer has a fine light slit, which is not illustrated. An angle 2 delta_beta_strich forms from the lateral offset for the returning light RS_r.

Figure 12:
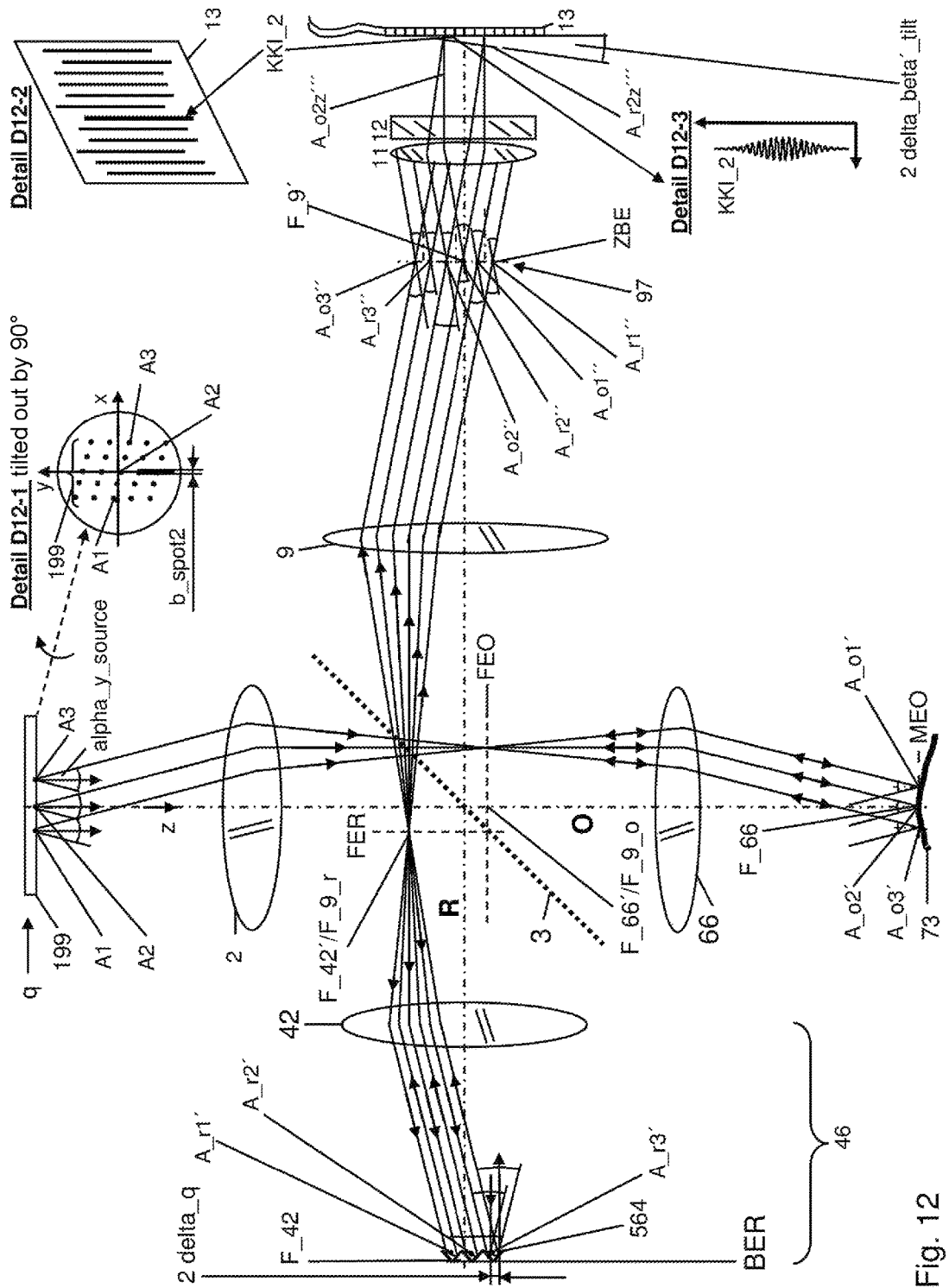
FIG. 12 illustrates an exemplary Linnik interferometer with a finely formed point light source matrix in accordance with one or more aspects of the present disclosure.

FIG. 12 basically illustrates a Linnik interferometer with a finely formed point light source matrix 199, which is formed to be spectrally broadband and exhibits an extension of the light spots below the diffraction-limited lateral resolution of the following collimator objective 2. A rough metal surface 73 as the object is located in the measuring plane MEO of the interferometer. Arranged in the reference arm is a hybrid retro reference end reflector system 46 with a rotationally symmetric reference objective 42 with which a 90° hollow roof edge mirror micro end reflector array 564 is associated. The 90° roof edge mirror reflectors do not necessarily have a tight 90° angle tolerance. The 90° hollow roof edge mirror micro end reflector array 564 is slightly offset laterally, so that also the small 90° hollow roof edge mirrors are offset slightly and the image points A_r1', A_r2', and A_r3' as luminous spots A1, A2, and A3 from the point light source matrix 199 are not imaged into the roof edges, but at least approximately sharply into the roof edge plane. Thus, a transverse offset 2 delta_q often forms in this way.

Astigmatic imaging of points of the rough metal surface 73, which are illuminated by light spots of the finely formed point light source matrix 199, onto the rasterized detector 13 is achieved by a cylinder objective 12 in combination with a rotationally symmetric objective 11.

Figure 13:
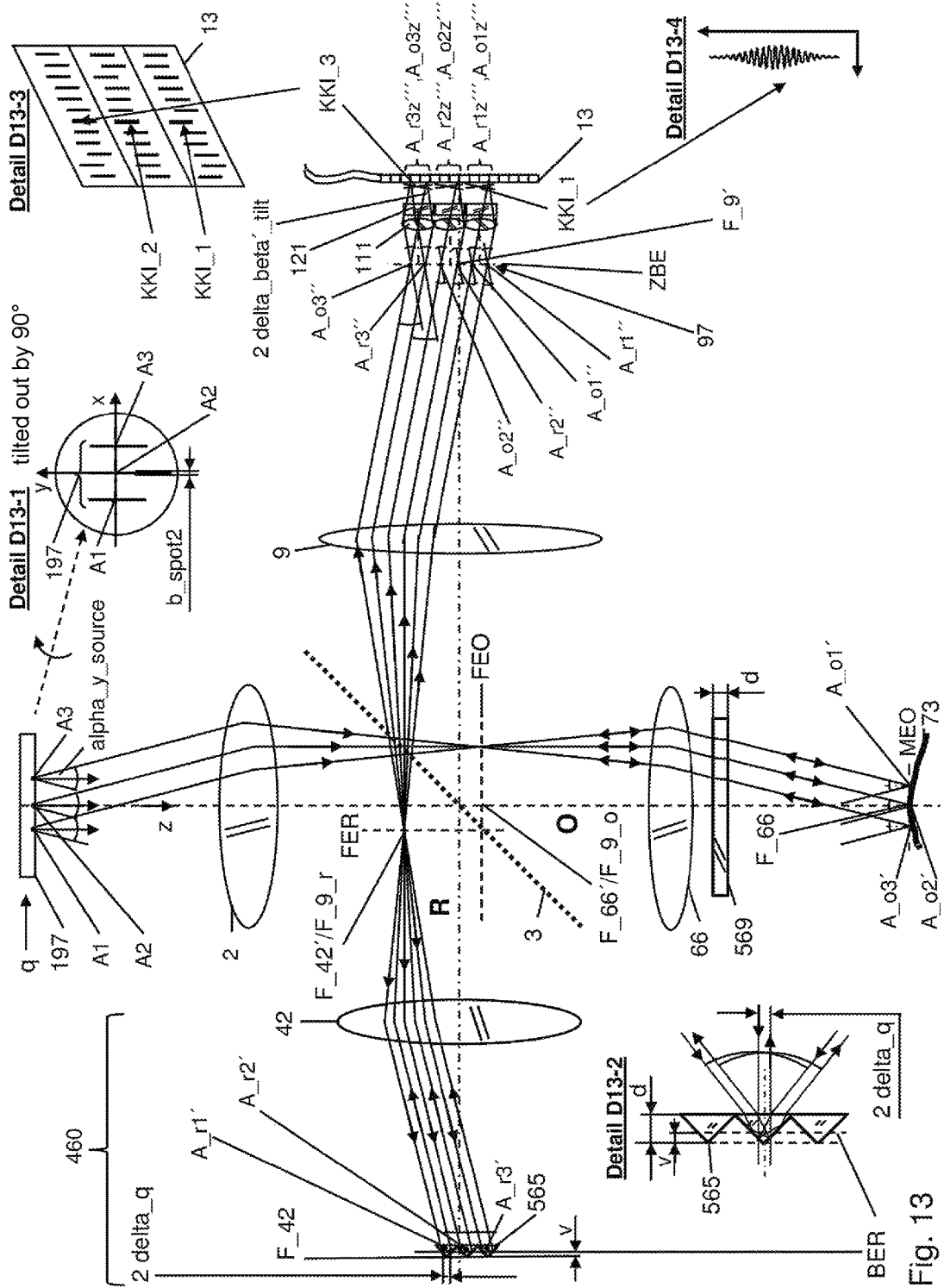
FIG. 13 illustrates an exemplary assembly for robust one-shot interferometry with a Linnik interferometer in accordance with one or more aspects of the present disclosure.

FIG. 13 illustrates an assembly basically according to FIG. 12. Arranged in the reference arm is a hybrid retro reference end reflector system 460 with a rotationally symmetric reference objective 42, which in contrast to FIG. 12 is assigned a 90° roof edge prism mirror micro end reflector array 565. To compensate for the optical thickness of the 90° prisms in the 90° roof edge prism mirror micro end reflector array 565 for the purpose of avoiding strong uncompensated dispersion in the interferometer, a compensation plate 569 of the same optical thickness as the 90° prisms in the micro end reflector array 565 is located in the object arm. In this way, the undesired and also excessively strong chirping in the short-coherence interferogram KKI is prevented. Astigmatic imaging of points of the rough metal surface 73, which are illuminated by light spots of the finely formed point light source matrix 199, onto the rasterized detector 13 is achieved by cylindrical microlenses 121 in a cylinder microlens array, which can be combined with rotationally symmetric microlenses 111 in a microlens array. The detail D13-1 shows the illumination with three light slits. The detail D13-2 illustrates the 90° roof edge prism mirror micro end reflector array 565. The detail D13-3 shows the arrangement of the short-coherence interferogram KKI on the rasterized detector 13. The detail D13-4 shows the signal progress in a detected short-coherence interferogram KKI.

Figure 14:
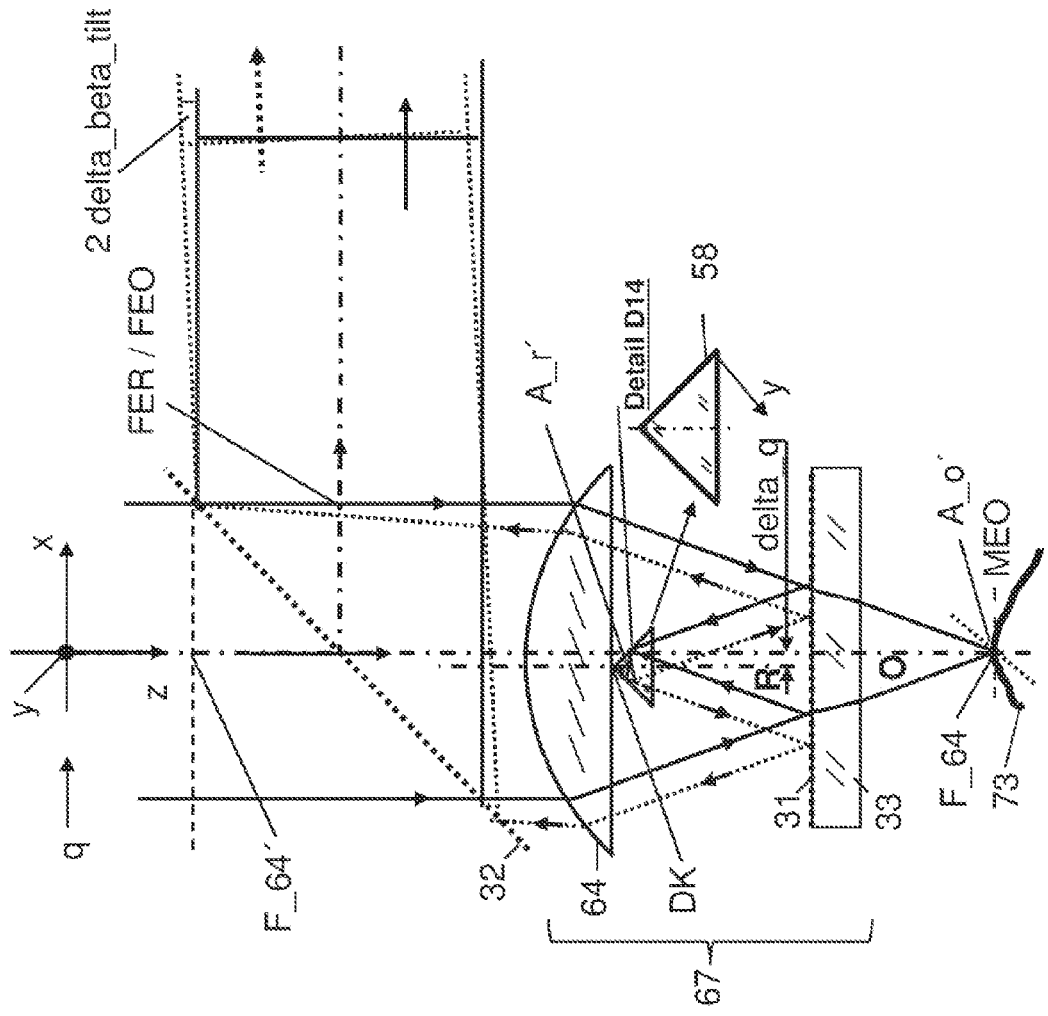
FIG. 14 illustrates an exemplary an assembly for robust one-shot interferometry with a Mirau interferometer in accordance with one or more aspects of the present disclosure.

FIG. 14 illustrates an assembly with a Mirau interferometer 67. Illumination is performed via a fine light slit not illustrated here. A stationary 90° roof edge prism 58 having its roof edge DK located optically in the focal plane of the objective 64 is arranged in the reference arm R of the Mirau interferometer. The roof edge DK of the 90° roof edge prism 58 is oriented parallel to the y axis and parallel to the longitudinal extension of the fine light slit for interferometer illumination, which is not illustrated here. The 90° angle tolerance of the 90° roof edge prism is rather great here. In this Mirau interferometer arrangement, a lateral shear 2 delta_q is introduced between the wavefronts, which, after the objective 64 has been passed, results in a tilt of the wavefronts of object and reference arms of 2 delta_beta_tilt. The optical path length of the 90° roof edge prism 58 is compensated for by the optical path length of the beam splitter 33. The detail D14 illustrates the roof edge prism 58, the optical path length of which corresponds to the plate 33 in the beam splitter 31.

Figure 15:
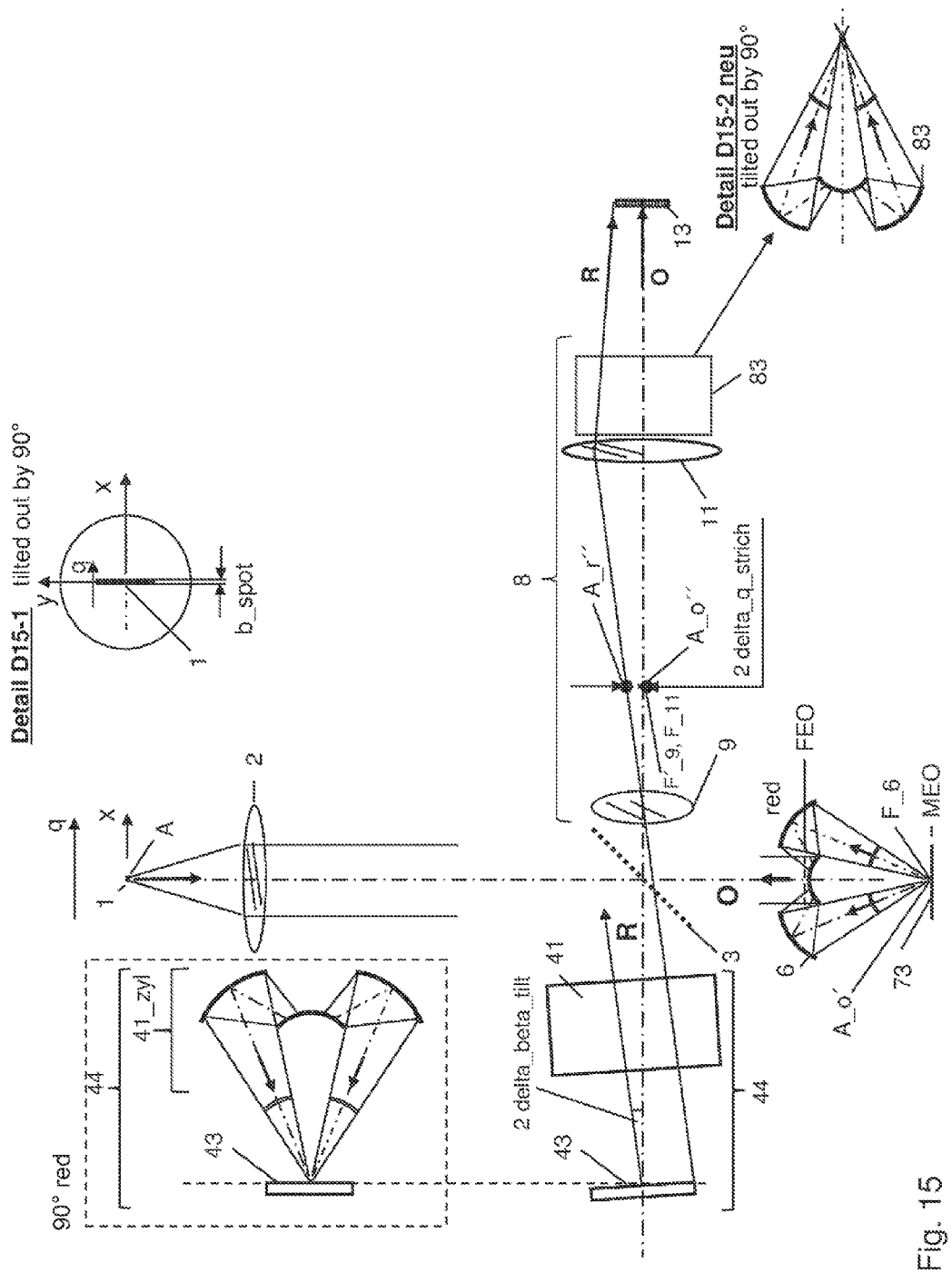
FIG. 15 illustrates an exemplary interferometer arrangement with a narrow line source in accordance with one or more aspects of the present disclosure.

FIG. 15 illustrates an interferometer arrangement with a narrow line source 1, illustrated in detail D15, and with a Schwarzschild cylinder mirror objective 41. The width b_spot of the narrow line source 1 is below the diffraction-limited resolution of the light source objective 2, cf. detail D15-1. The detail D15-2 shows a Schwarzschild cylinder mirror objective 83 in the detection optical path for generating cylinder waves on the rasterized detector 13.

Figure 16:
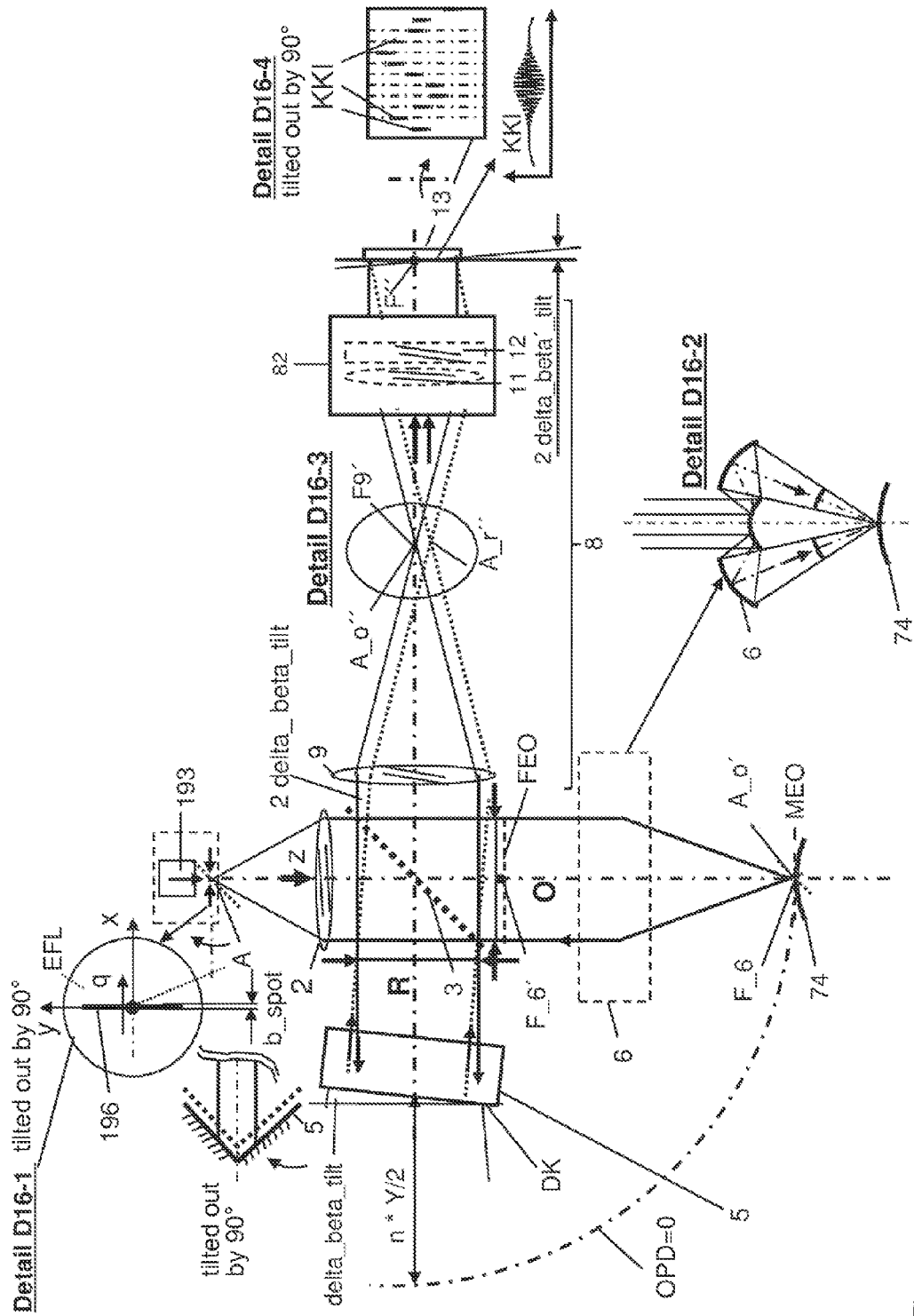
FIG. 16 illustrates an exemplary assembly for robust one-shot interferometry with a hybrid interferometer in accordance with one or more aspects of the present disclosure.

FIG. 16 illustrates an assembly with a hybrid interferometer according to the Linnik approach, or may also be understood as a two-beam arrangement on the basis of a Michelson interferometer with an object-imaging objective in the object arm. This two-beam interferometer is operated with a frequency comb laser. A line-like illumination by means of the fine light slit 196 is performed, illustrated in detail D16-1, wherein the line width b_spot is below the lateral resolution of the collimator objective 2. The assembly is used for measuring the residual roughness of an optically smooth metal surface 74. The image of the slit (A_o') is located on the optical axis of the Schwarzschild mirror objective 6. Detail D16-2 shows the Schwarzschild mirror objective 6 arranged in the object arm O of the interferometer. By means of the mirror optical system, dispersion in the interferometer is avoided. The lateral shear of the roof edge DK of the roof edge reflector 5 in y direction is made to be zero. The roof edge DK is located optically at least approximately in the Fourier plane of the focusing objective 6, whereby interferences of the same inclination are largely avoided in the detection plane. The detail D16-4 shows short-coherence interferograms KKI on the rasterized detector 13, one for each measurement point on the optically smooth metal surface 74.

Figure 17:
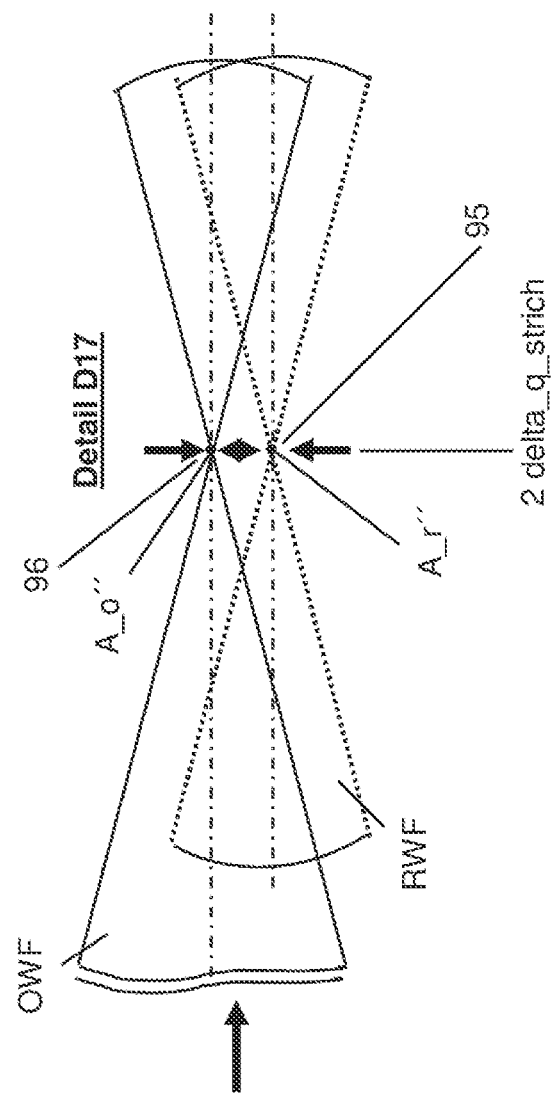
FIG. 17 illustrates an exemplary assembly for robust one-shot interferometry with a hybrid interferometer in accordance with one or more aspects of the present disclosure.

The detail D16-3 is enlarged in FIG. 17. It shows a fine slit diaphragm 96 for object radiation, which is used for low-pass filtering at the Airy limit and below, so that an object wavefront OWF can at least approximately be formed entirely also by a less cooperative measurement point. However, it may be that there is an "undeterminable" phase jump in the detected spatial interferogram on the rasterized detector 13, so that the phase information of an object point gets lost and is not available for the depth determination.

FIG. 18 illustrates a hybrid interferometer according to the Linnik approach, in the reference arm R of which a 90° hollow roof edge reflector 5 with the roof edge DK is located in a way inclined about the tilt angle delta_beta_tilt. According to detail D18-1, illumination takes place via a fine light slit 196. The detail D18-2 illustrates the Schwarzschild objective 6 used in the object arm O in detail. Detail D18-3 shows the 90° hollow roof edge reflector 5 in the reference arm R, which is tilted out by 90°. After beam unification at the beam splitter of the returning light from the reference arm R and the light from a rough metal surface 73 from the object arm O, the bundle is focused by means of the tube objective 9. Due to the tilt of the 90° hollow roof edge reflector 5, the focus spots A_r" and A_o" are laterally separated in the focal plane F_9'. A_r" and A_o" represents images of a luminous point A. By means of an astigmatic detector objective, in the combination rotationally symmetric objective 11 and cylinder objective 12, an object cylinder wave from each object point detected in the depth of field of the Schwarzschild objective 6 is formed on the rasterized detector 13, said object cylinder wave being inclined by the angular magnitude 2 delta_beta'_tilt with respect to the reference cylinder wave, so that a pair of interfering cylinder waves exists there. Detail D18-4 shows the short-coherence interferograms KKI being formed.

The rectangle in FIG. 19 shows the width b_spot_g' of the computed geometrical-optical image from the fine light slit 196, the image of which corresponding to about half the Airy disc width.

Figure 20:
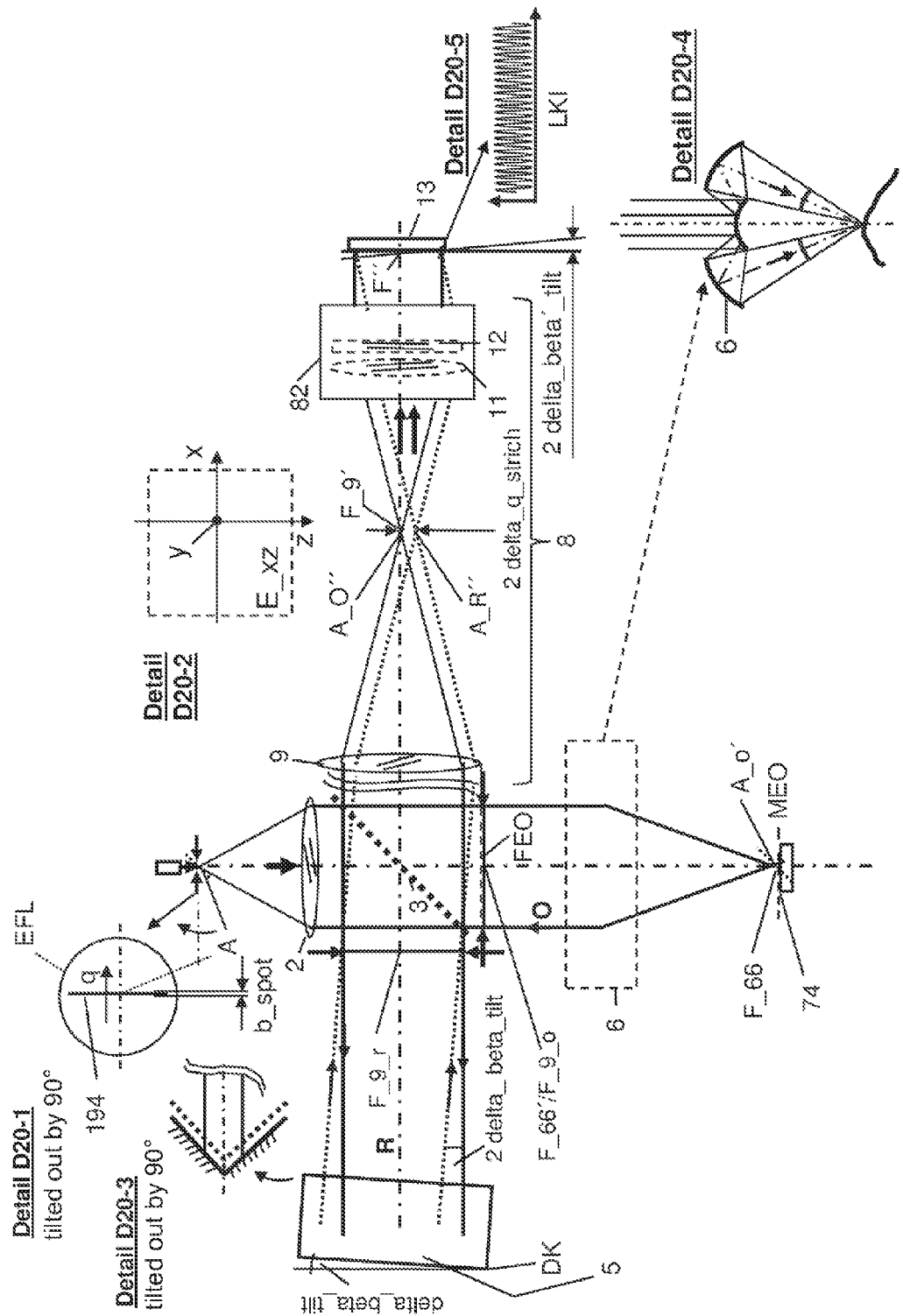
FIG. 20 illustrates an exemplary sensor for respectively measuring a very short profile line in accordance with one or more aspects of the present disclosure.

FIG. 20 is based on the optical circuit according to FIG. 18 and illustrates a sensor for measuring a very short profile line, since there is a quadratic phase term in the spatial interferogram. Detail D20-2 shows the coordinate system.

The light source used is a comparably strong single-mode laser as light source with a rotating chopper wheel synchronized with respect to the rasterized detector 13. The smoothness deviation of a plane and optically smooth metal surface 74 is measured here. Thus, wavelets without a zero-order stripe form on the rasterized detector 13. The height differences of adjacent measurement points in a very short range are clearly below a quarter of the laser wavelength. Accordingly, for measuring the optically smooth metal surface 74, only phase differences clearly below 180 degree (180°) need to be evaluated in order to be able to represent the profile of the optically smooth metal surface 74.

Figure 21:
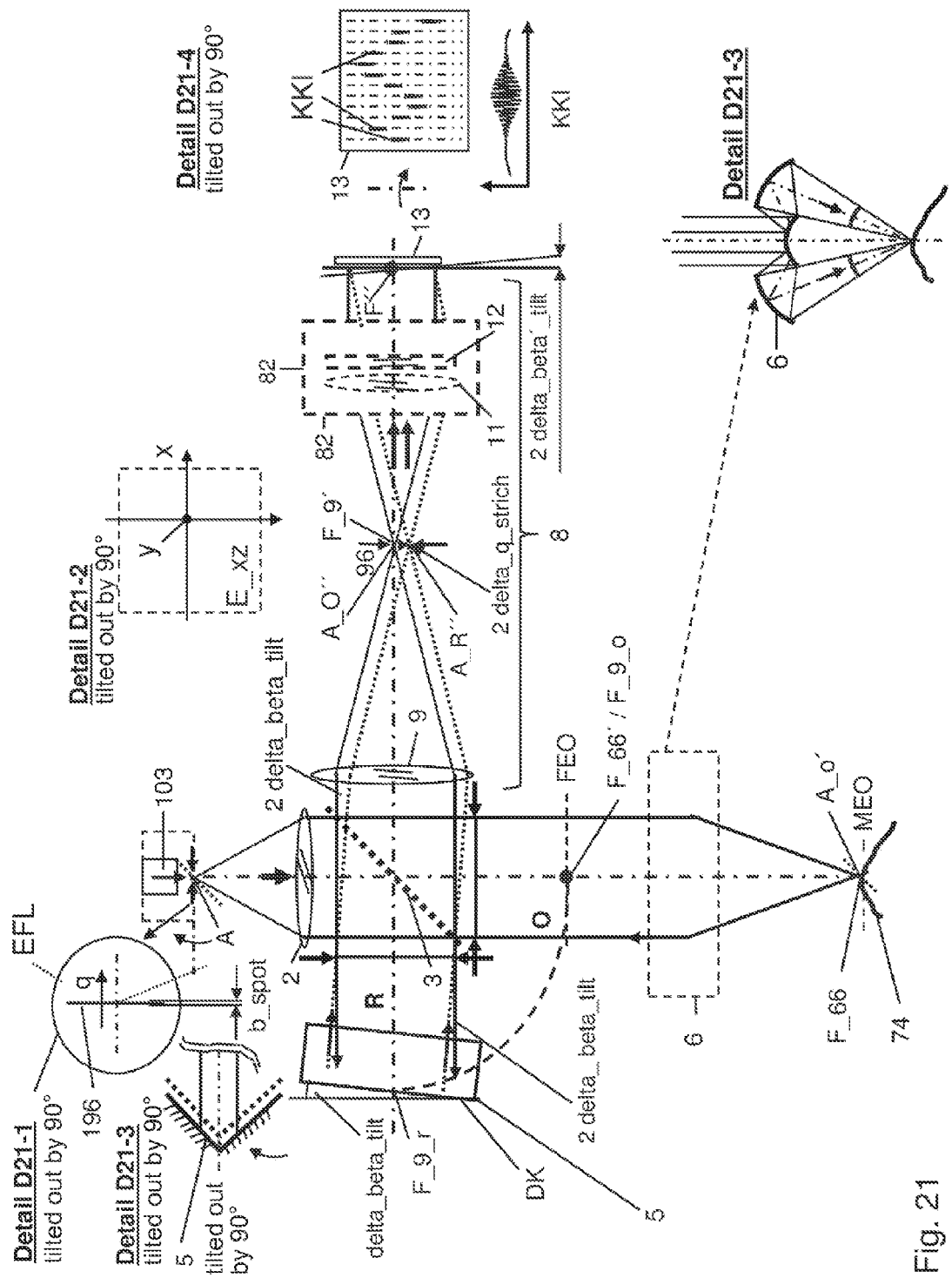
FIG. 21 illustrates an exemplary sensor for respectively measuring a very short profile line in accordance with one or more aspects of the present disclosure.

FIG. 21 illustrates an assembly comparable with that of FIG. 20, except for the reference end reflector position. In this case, however, use is made of a fine light source 103 with a frequency comb laser that is modulated with a rotating chopper wheel in the one-digit kHz range. The frequency comb laser compensates for the comparably great optical path difference of the two-beam interferometer in a known way, so that short-coherence interferograms can be detected. Here, the roof edge reflector 5 is at least approximately in the plane conjugated with respect to the plane FER, so that no quadratic phase term occurs in the wavelet and longer profile measurements compared to the assembly in FIG. 20 can be performed.

Figure 22:
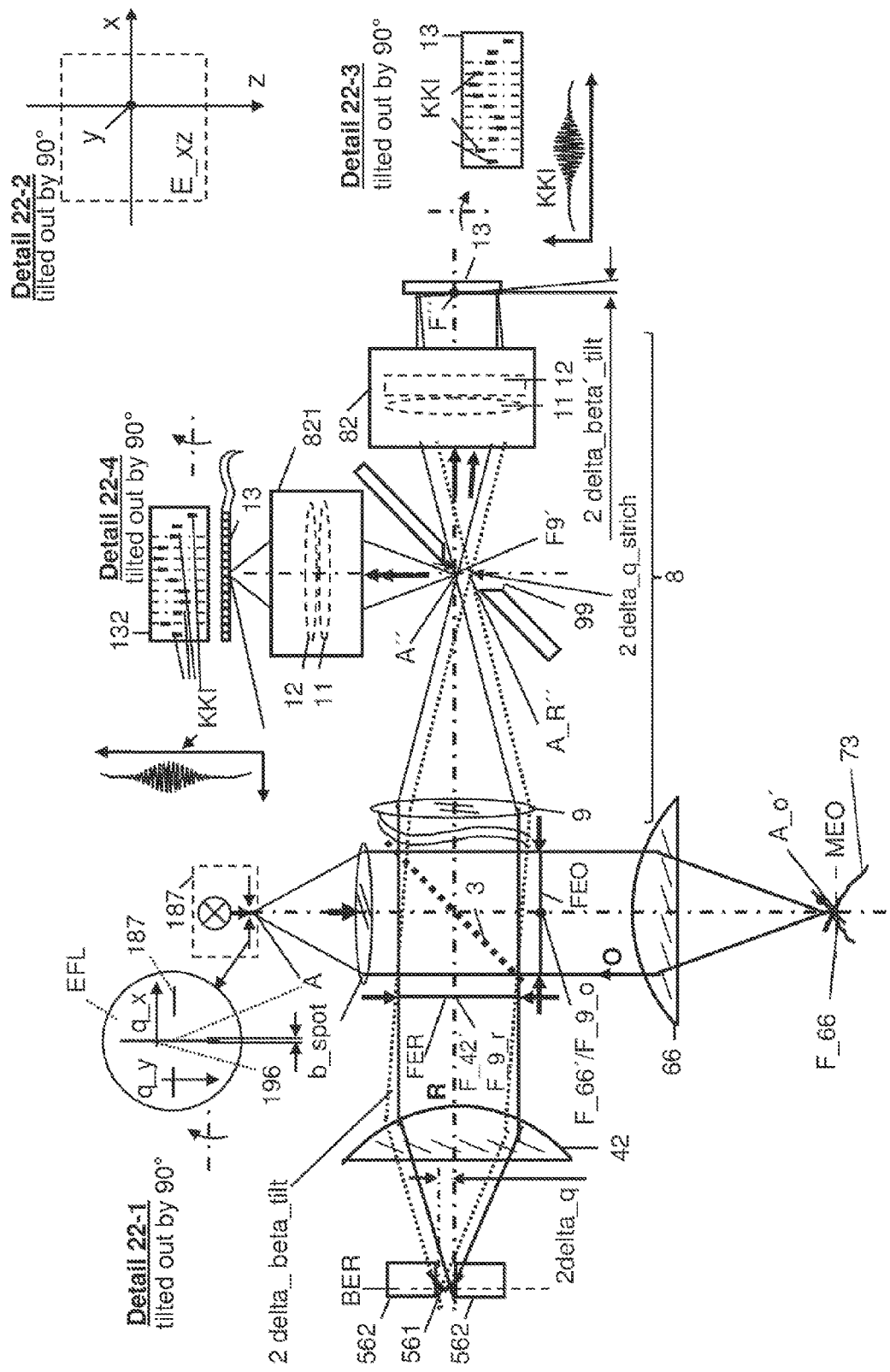
FIG. 22 illustrates an exemplary a Linnik interferometer in accordance with one or more aspects of the present disclosure.

FIG. 22 shows a Linnik interferometer in which a line-like measurement can be performed in two mutually rectangular directions at the same time. To this end, as is illustrated in detail D22-1, two fine light sources 197 are formed as a point light chain in a 90° arrangement, which emit pulsed light in the low kHz range. The lateral extension in q_x and q_y directions is respectively below the lateral resolution in imaging onto the object surface, which is a rough metal surface 73 here. Correspondingly, two 90° hollow roof edge reflectors 561 and 562 arranged by 90° with respect to each are positioned in the reference arm R. This makes up a two-channel-x-y measuring assembly. In the detection optical path, the two channels are separated in terms of geometrical optics by means of a plane deflecting mirror 99 with a fine slit diaphragm, and after passing an astigmatic detector objective 82 and 821, are each supplied to a rasterized detector 13 and 132, where short-coherence interferograms KKI of appropriate measurement points are detected.

In FIG. 23, the coherent Airy spots A_o_i' and A_r_i' as well as A_o_i+1' and A_r_i+1', which are each formed by a fine light source 190 with fine light spots via beam splitting and passage of reference arm R and object arm O, are positioned comparably close together. The illustration refers to the hollow 90° roof edge end reflector 561, to which the object spots are projected back. The distance of the Airy spots is in the order of magnitude of the Airy pattern width. FIG. 24 shows the resulting spatial interferograms for three measurement points, which each are assigned their own optical path through to the detection via microlenses not illustrated here, wherein astigmatic imaging of the interfering bundles with formation of cylinder waves was dispensed with. A possible optical path with microlenses is suggested by the assembly in FIG. 72, where the foci are separated in depth though.

The spatial interferograms illustrated in FIG. 24 may also be referred to as light-field interferograms, one for each individual object point. Due to the small lateral distance of the coherent spots A_o_i' and A_r_i' as well as A_o_i+1' and A_r_i+1', only few stripes form during the detection. The middle stripe represents the zero-order stripe owing to the exact position of the associated object point. The stripe distance is at least approximately constant.

Figures 25, 26:
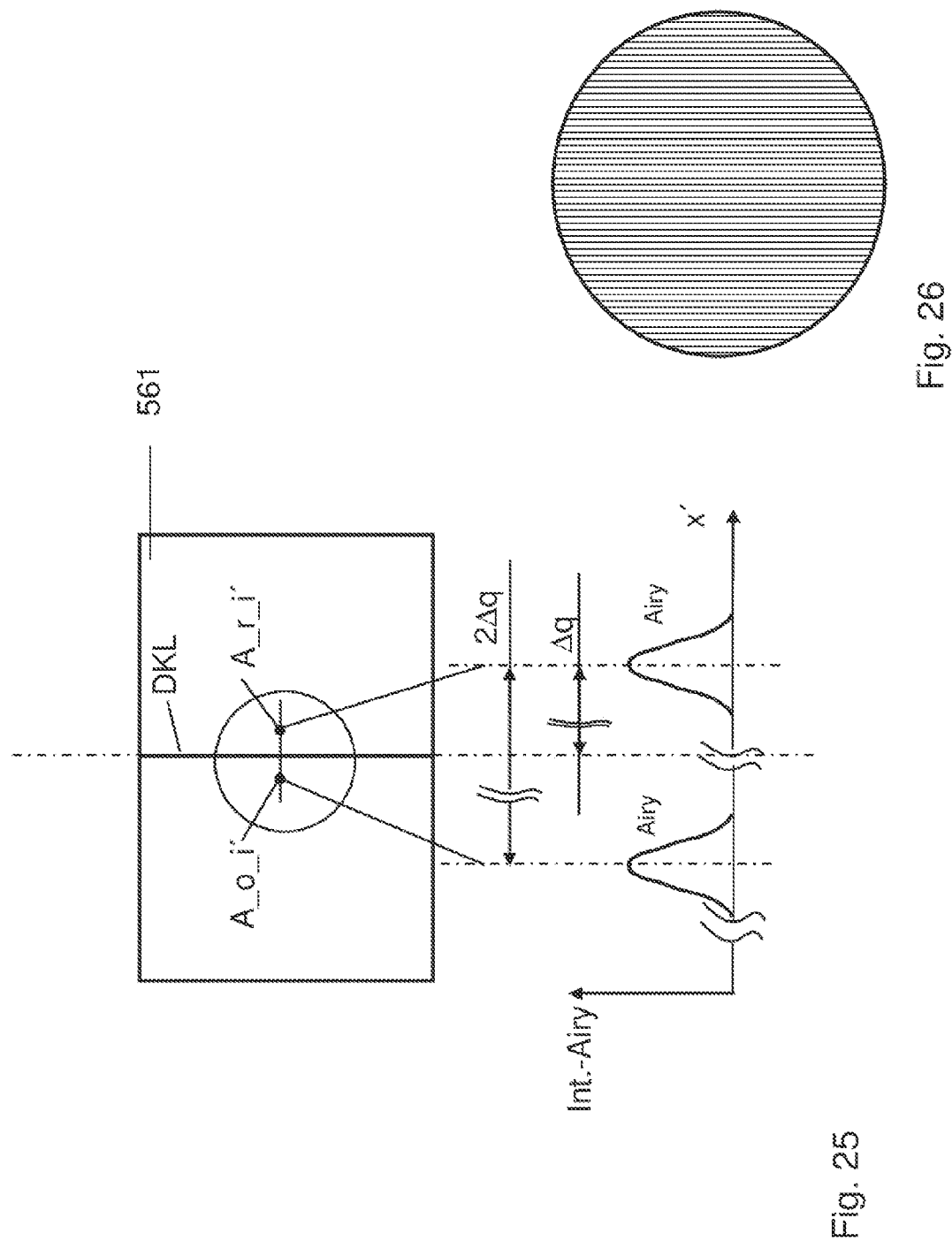
FIG. 25 illustrates exemplary coherent Airy spots in accordance with one or more aspects of the disclosure.
FIG. 26 illustrates an exemplary coherent Airy spatial interferogram in accordance with one or more aspects of the disclosure.

In FIG. 25, Airy spots are positioned together slightly further away from each other on the hollow 90° roof edge end reflector 561 in the reference arm R of the interferometer, with a distance in the order of clearly above ten times the Airy pattern width. In this case as well, the object spots were projected back for presentation on the hollow 90° roof edge end reflector 561. FIG. 26 shows the resulting spatial interferogram as an interference of coherent reference spots and object spots. Due to the transverse offset 2 delta_q, which is clearly greater compared to FIG. 23, a plurality of interference stripes forms during the detection. In this case as well, the stripe distance is at least approximately constant and does rather not carry any information about the measurement object.

Figure 27:
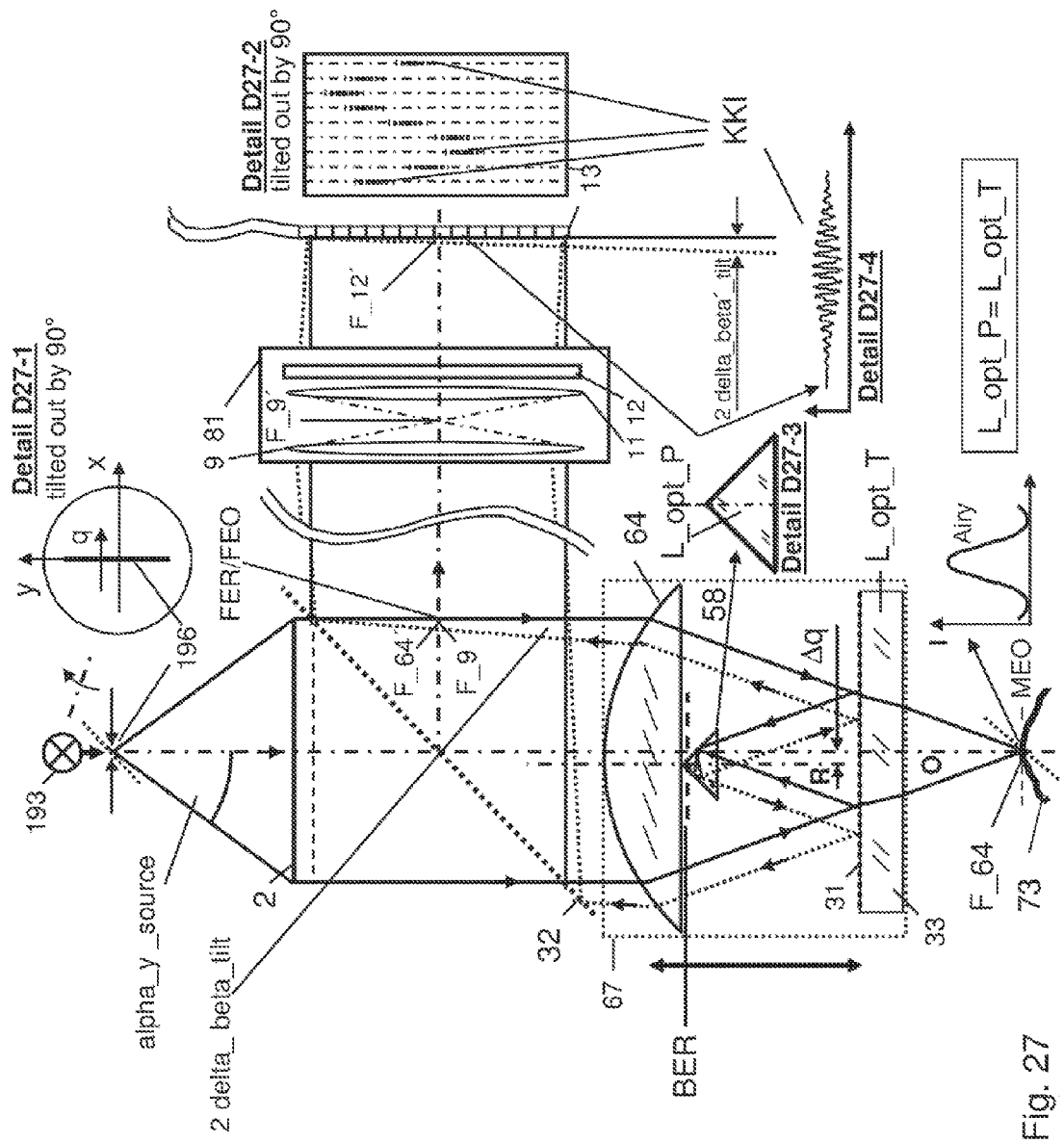
FIG. 27 illustrates an exemplary line sensor in Mirau interferometer arrangement in accordance with one or more aspects of the present disclosure.

FIG. 27 illustrates a line sensor in a Mirau interferometer arrangement. The reference roof edge mirror prism 58 exhibits the same geometric path for principal rays in the same glass type as the splitter plate 33. Thus, there is a compensation of the optical glass path length and no chirping occurs in the short-coherence interferograms. For quickly detecting the miniform of a rough and slightly curved metal surface 73, the Mirau objective interferometer 67 moves in the depth direction by means of a non-illustrated height-adjustable table in order to detect the object points in the depth of field, so that an image with Airy pattern from the fine light slit 196 can form on the object surface. Short-coherence interferograms are formed on the rasterized detector 13 by astigmatic imaging in the detection optical path.

Figure 28:
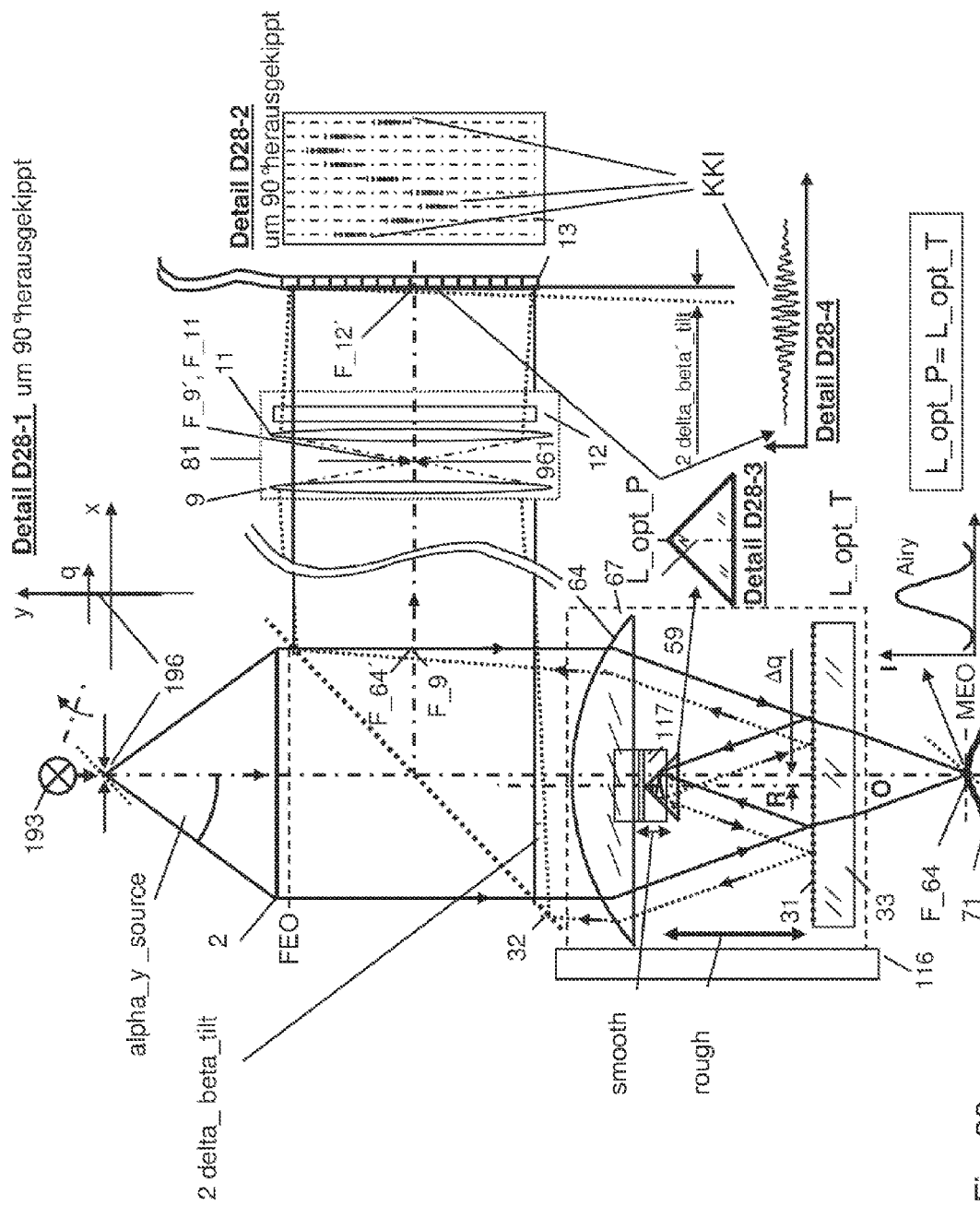
FIG. 28 illustrates an exemplary line sensor for detection the surface of human skin in accordance with one or more aspects of the present disclosure.

FIG. 28 illustrates a line sensor with a fastest possible scan by the Mirau objective interferometer 67 for detecting the surface of human skin 71 on a patient. The optical setup at first corresponds to that of FIG. 27, but in addition to the highly dynamic linear drive 116 for the Mirau objective interferometer 67, a highly dynamic linear drive for the 90° roof edge prism 59, a piezo actuator 117, is arranged as well. Due to the strong acceleration of the piezo actuator 117, this combination allows a path-time course of optical scanning with a comparably well approximated triangular profile and thus virtually no loss of time in the reversal points of the scan. Thus, a depth measuring range for profile detection that is a multiple of the wave-optical depth of field results for the sensor. By means of a lateral scan, it is possible to scan through a comparably large measuring volume in a fast way. In this assembly as well does the reference roof edge mirror prism 59, in the same glass type, exhibit the same geometric path for principal rays as the splitter plate 33. The slit diaphragm 961 also serves to suppress the background light from the depth of the measured skin 71 in order to improve signal contrast.

FIG. 29 illustrates a Mirau interferometer 68 for white light interferometry with a Schwarzschild objective 63. Several positioning systems for fast movement of the Mirau interferometer 68 are arranged. The 90° roof edge prism 59 also moves highly dynamically in the z direction in the reference arm. For example, according to FIG. 30, a triangular profile can be obtained in the course of the path of the Mirau interferometer 68 over time. FIG. 31 shows approximately the path course in x direction over time t. FIG. 32 represents the scan path on a living organ. Detail D32-1 illustrates individual measurement cells, and detail D32-2 illustrates the measurement volume that can be detected in a measurement process.

Figure 33:
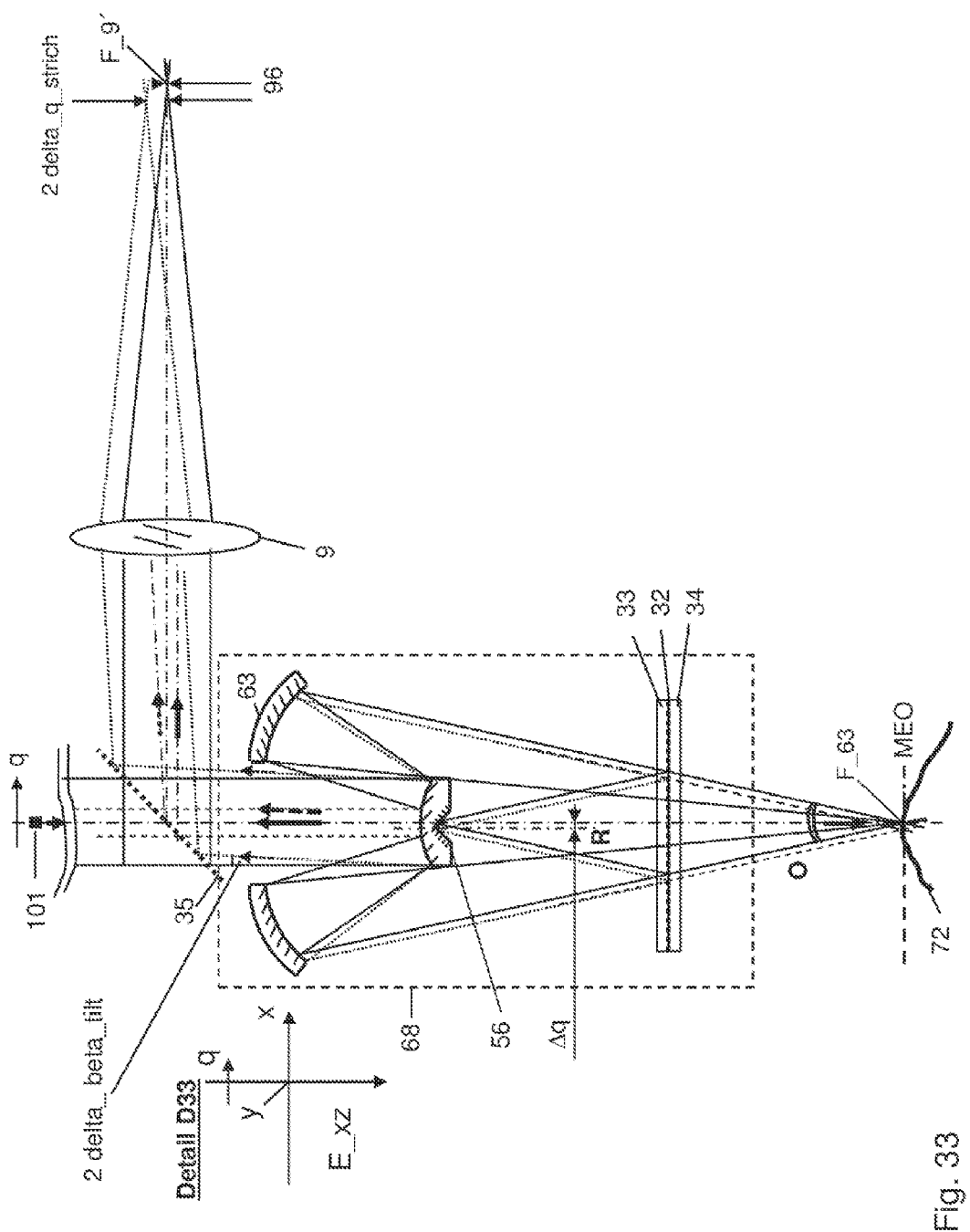
FIG. 33 illustrates an exemplary Mirau interferometer arrangement with a Schwarzschild measuring objective in accordance with one or more aspects of the present disclosure.
Figure 34:
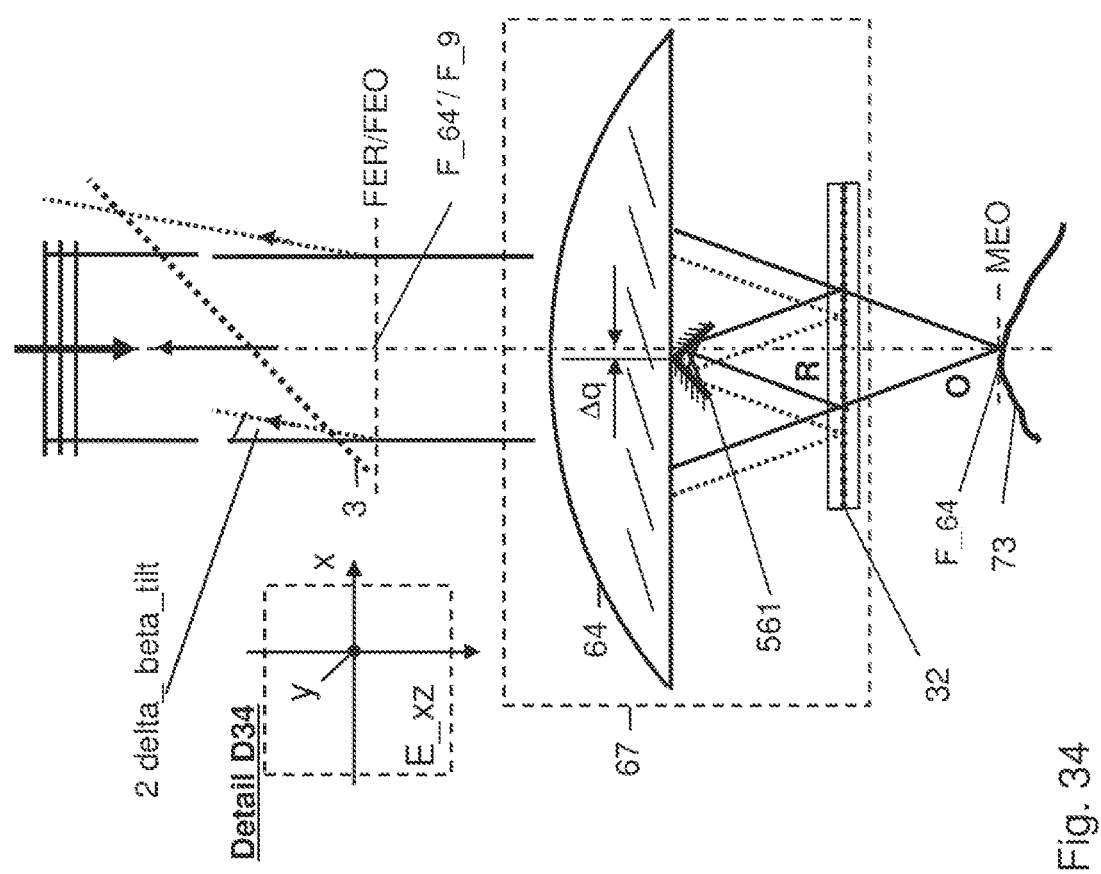
FIG. 34 illustrates an exemplary Mirau interferometer with a refractive measuring objective in accordance with one or more aspects of the present disclosure.

FIG. 33 illustrates a further Mirau interferometer arrangement with a Schwarzschild objective 63. The detail D33 shows the coordinate system. FIG. 34 represents a Mirau interferometer arrangement with a refractive measurement object 64.

FIG. 35 illustrates a Mirau interferometer system for measuring two line profiles arranged perpendicular to each other.

FIG. 36 shows the scanning direction of the measuring head located on a three-coordinate measuring machine, and the rectangularly arranged fine measurement lines originating from the fine, pulsed line light source 193.

Figure 37:
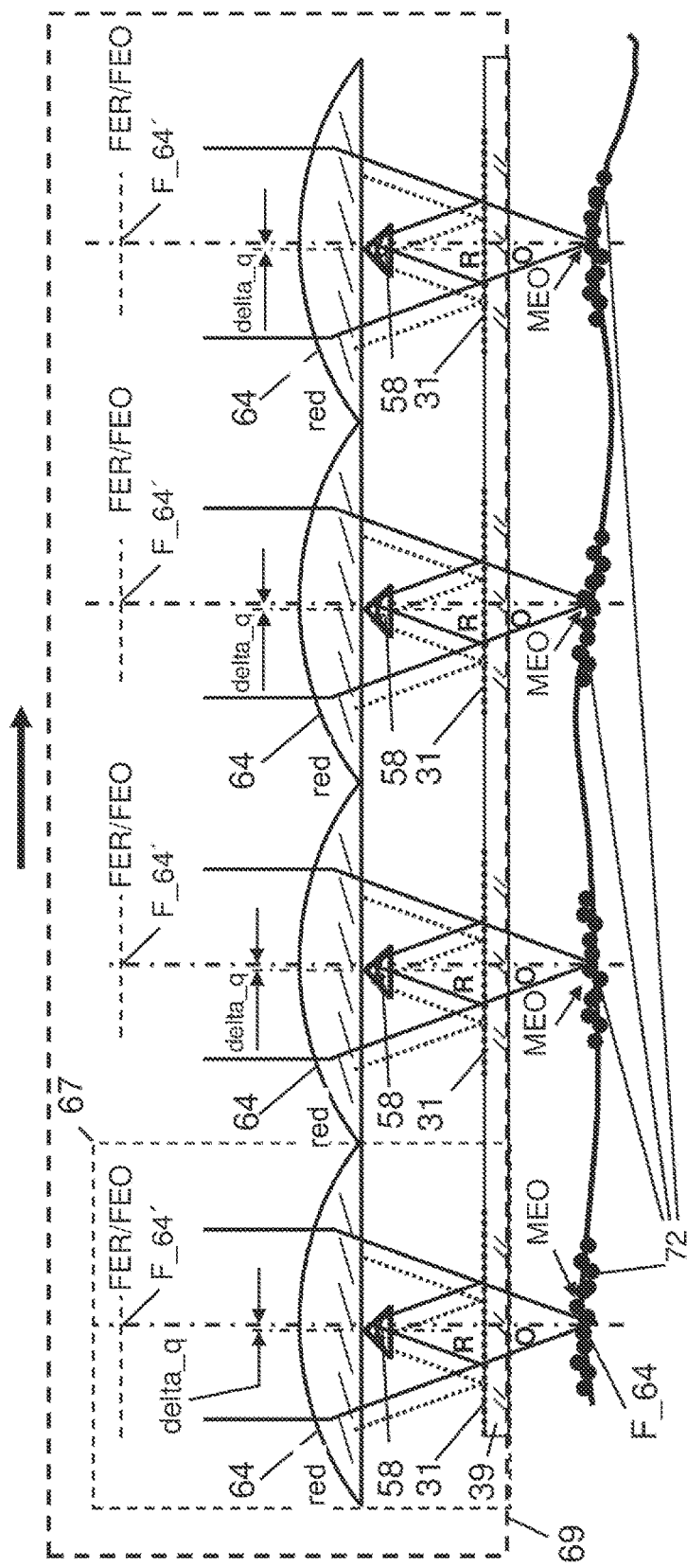
FIG. 37 illustrates an exemplary sensor array for microscopic 3D examination of a human organ in accordance with one or more aspects of the present disclosure.

FIG. 37 shows a sensor array for microscopic 3D examination of a human organ for detecting cancer cells by a fast linear scan on the surface of the living organ 72 during surgery.

FIG. 38 illustrates a multi-line sensor with a 90° hollow roof edge mirror micro end reflector array 564 in combination with a rotationally symmetric reference objective 42 in the reference arm in a Mirau configuration. In this way, it is possible to address several measurement lines simultaneously for profile detection on a rough metal surface 73. FIGS. 39 and 40 each show one view of the 90° hollow roof edge mirror micro end reflector array 564.

Figure 41:
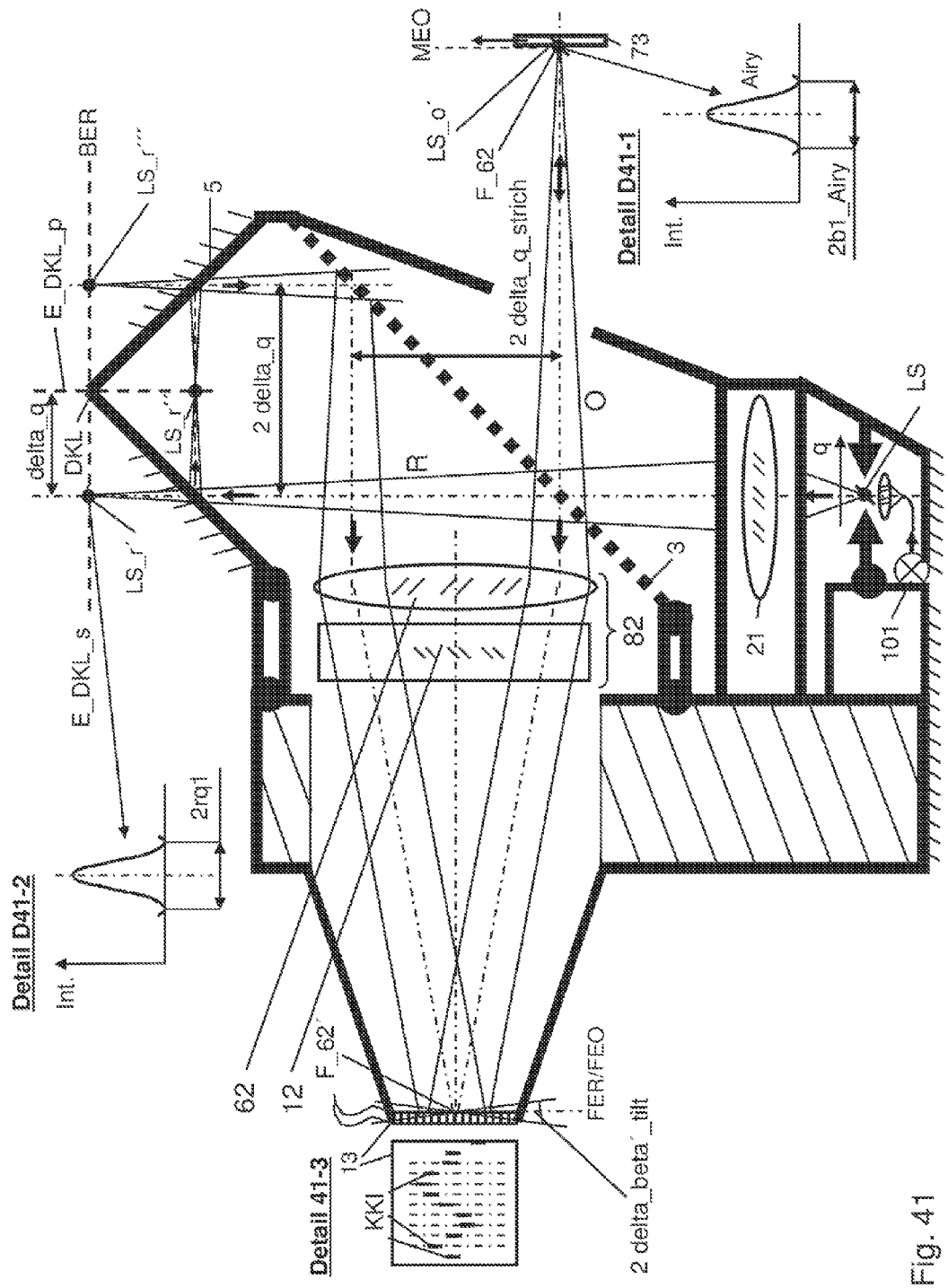
FIG. 41 illustrates an exemplary sensor array for microscopic 3D examination of metallic work-pieces in accordance with one or more aspects of the present disclosure.

FIG. 41 illustrates a sensor array for microscopic 3D examination of metallic workpieces.

Figure 42:
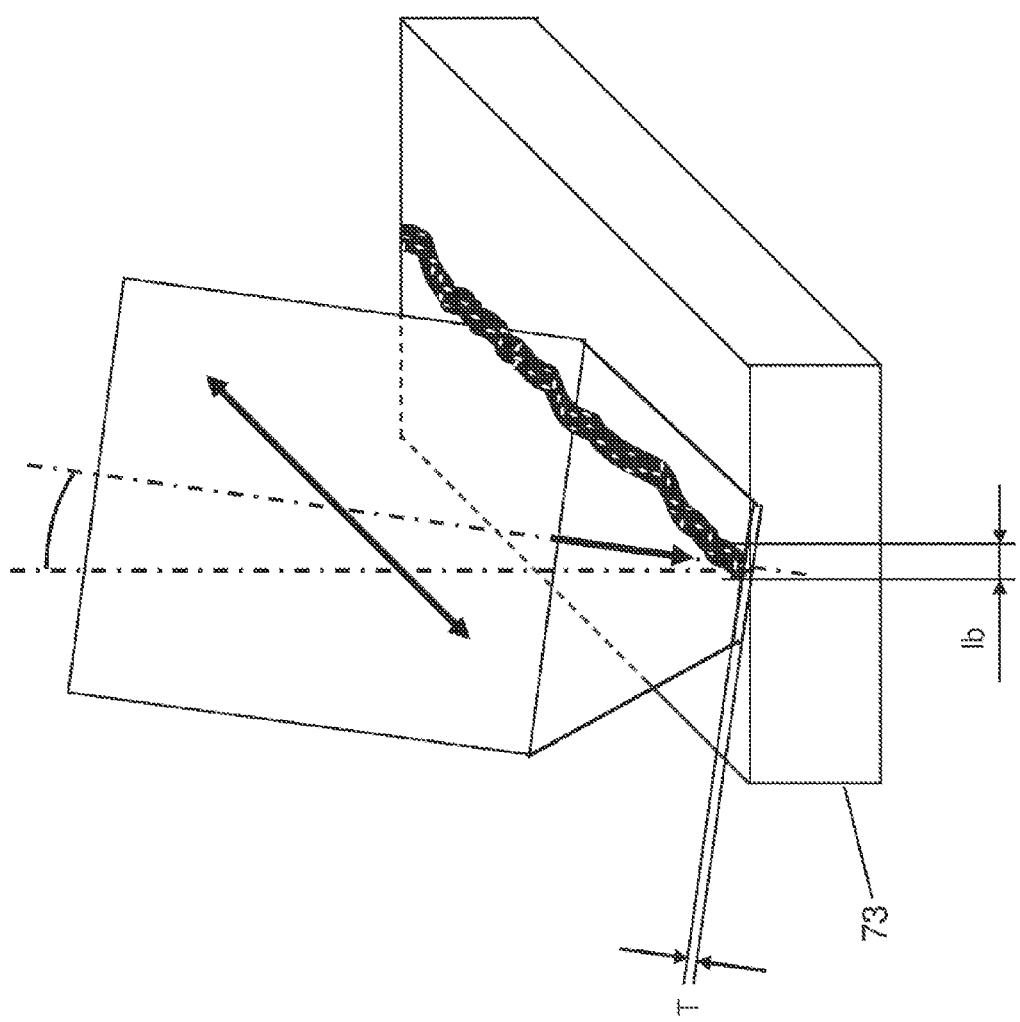
FIG. 42 illustrates an exemplary line sensor head in accordance with one or more aspects of the present disclosure.

FIG. 42 illustrates a line sensor head, which is slightly inclined over a large measurement object 73 and is moved quickly across the measurement object 73 for shape detection. This movement is performed by means of a 3D coordinate measuring machine. "Data excess" is employed in the measurement. Many measurement points on optically rough objects, shown in white here, are non-cooperative, i.e. not evaluable. However, this is usually not a problem due to the parallelized pick-up and the "data excess". From many valid measurement values—the black region represents the valid measurement points here—the 3D profile is determined in subareas even if sometimes the filling degree with valid measurement points is e.g. only 30% in subareas of the measurement field. Each measurement point is subjected to a "quality check" it needs to pass in order to be "admitted" to further processing to a 3D data set. Accordingly, the resulting profile line is not completely rectilinear. This does usually not pose a problem to the numeral evaluation and further use of the data.

Figure 43:
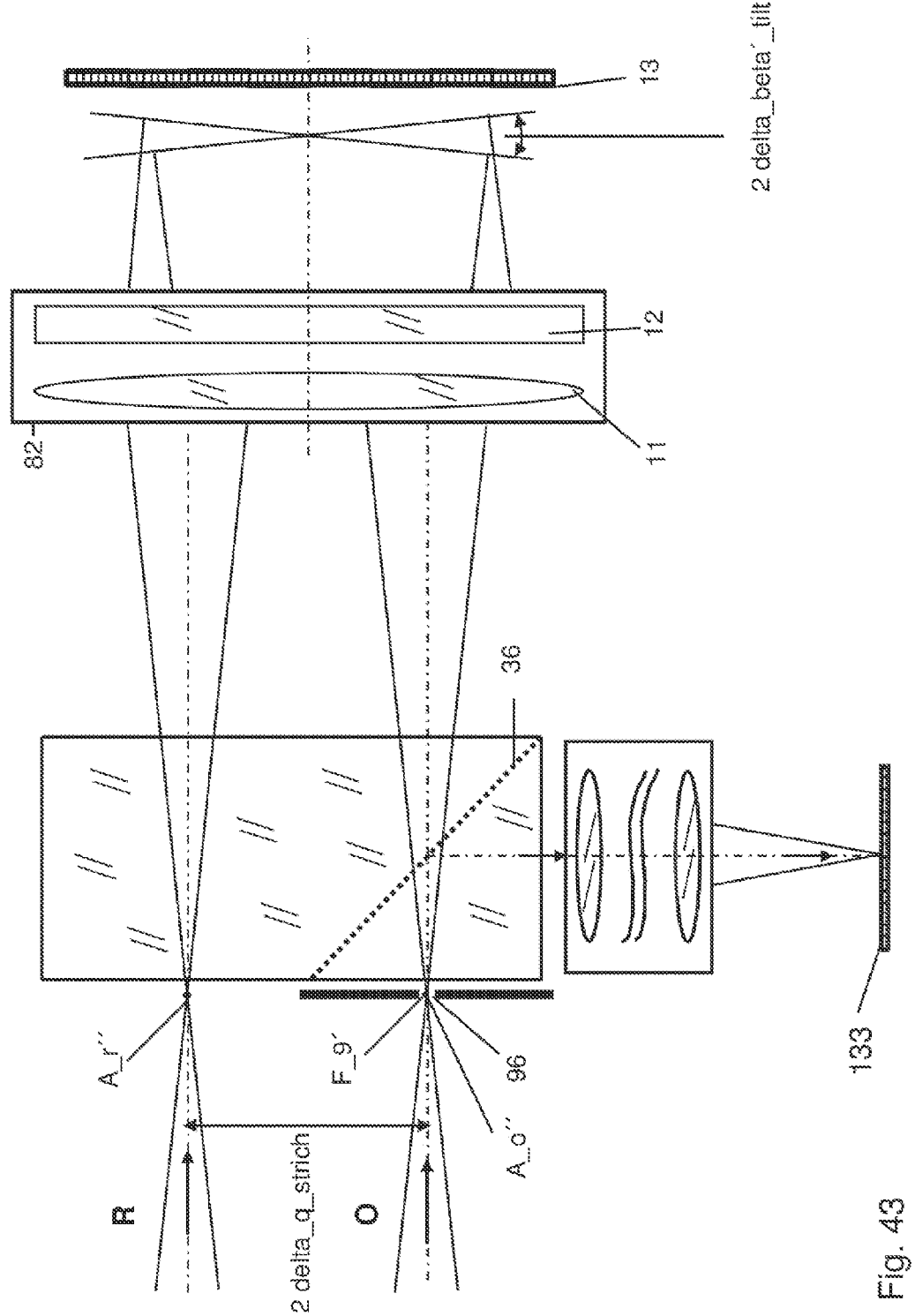
FIG. 43 illustrates an exemplary portion of a detection optical path in accordance with one or more aspects of the present disclosure.

FIG. 43 illustrates a part of the detection optical path with the possibility to couple out object light by means of a beam splitter 36 for spectroscopic analysis.

Figure 44:
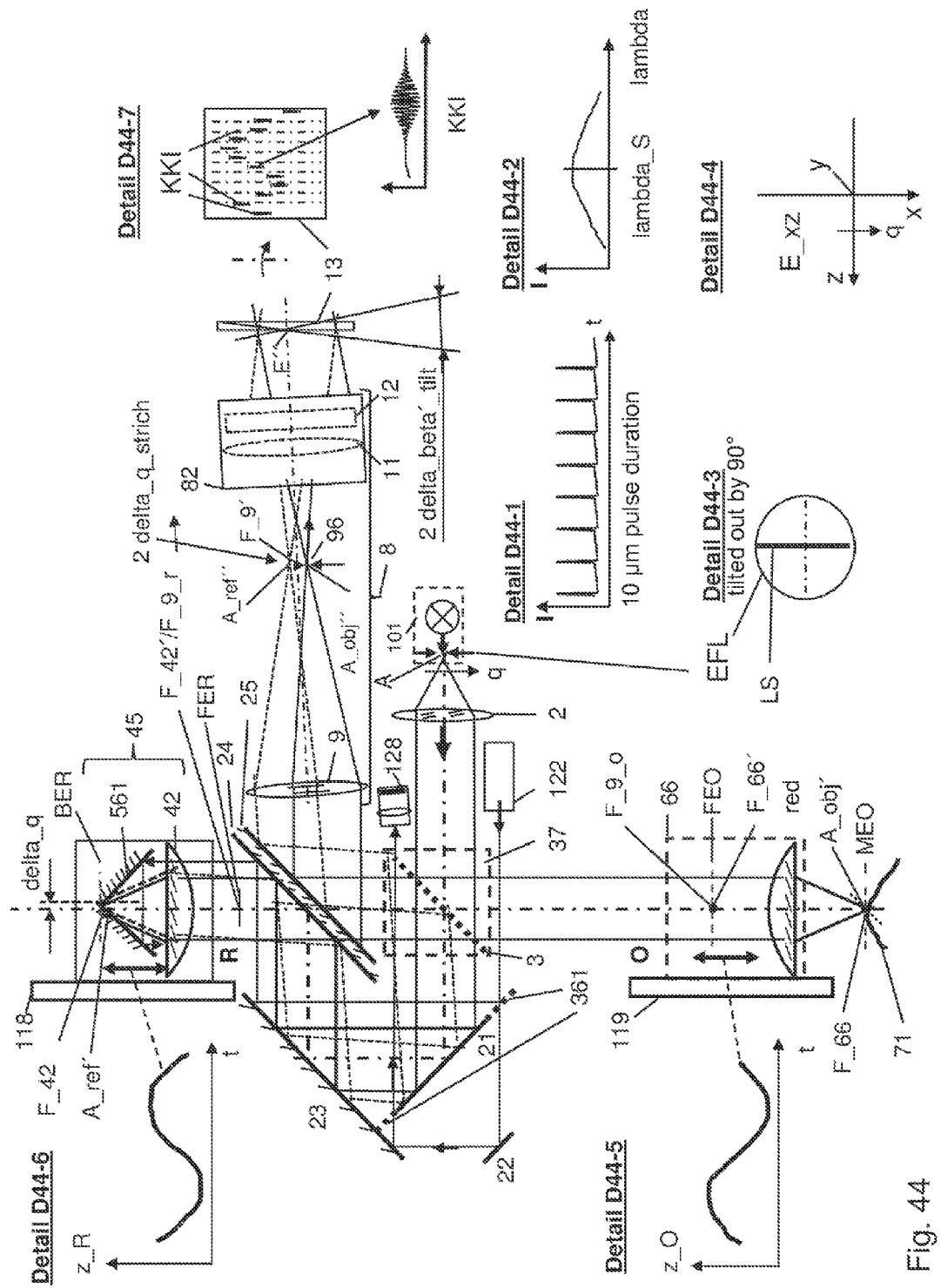
FIG. 44 illustrates an exemplary a hybrid interferometer in accordance with one or more aspects of the present disclosure.

FIG. 44 illustrates a hybrid interferometer. Synchronized counter-oscillation of the two objectives 66 and 42 for further compensation of restoring forces upon very fast acceleration of the objective masses takes place. The assembly is used as a highly mobile skin scanner for cancer cell detection for every body region on a human being.

The light coming from a pulsed short-coherent light source 1—behind a slit, lightened by this light source, of 10 μm slit width and 5 mm illuminated slit width—is detected and collimated by a collimator 2, operating in a diffraction-limited way, with half the aperture angle alpha_y_source of 2.8°, which yields a numerical aperture of 0.05.

The most important parameters of the pulsed short-coherent line light source 1 used, see also detail D44-1, in NIR, see also detail 44-2, at 800 nm to 900 nm are: 4 kHz pulse rate and 4% relative switch-on time of the pulsed short-coherent light source 1. The light pulses are generated by means of a non-illustrated rotating chopper wheel and have an average pulse time of 10 μs. The coherence length of the light source 1 is 8 μm. The continuous-wave performance of the pulsed short-coherent light source 1 is 100 mW in the NIR. The digital camera 13 with 1024×256 pixels has a frame rate of 4 kHz and is strictly synchronized with respect to the motion of the chopper wheel.

The collimated light reaches a highly symmetrically formed beam splitter cube 37 in the interferometer, said cube being matched to better than 10 μm glass path length difference. The interferometer operates at least approximately at the optical path difference of zero. In the reference arm R, after a threefold 90° deflection in air, the transmitted beam bundle reaches a diffraction-limited reference objective 42 with a roof edge reflector 561 fixedly arranged in the focus position thereof, with the roof edge DK thereof being in the focal plane of the reference objective 42. The optical axes of the reference objective 42 and a structurally identical measuring objective 66 are flush. The roof edge reflector 561 has a transverse offset delta_q with respect to the optical axis of the reference objective 42. The radiated light is offset transversely by 2 delta_q by means of the roof edge reflector 561 and is subjected to a wavefront inversion at the roof edge reflector 561 and, after passing the reference objective 42, is incident on the beam splitter cube 37 again in an inclined way, where the light is partly reflected and enters the detection optical path. The beam bundle reflected at the beam splitter cube 37 after entry of light reaches the measuring objective 66, which focusedly images the slit image with its NA of 0.14 in a diffraction-limited way in line from in the object space. Here, the mechanical scan range of the mechanically moved measuring objective 106 is +/−1 mm deviation. Also focused light can slightly enter the human skin 71. It is scattered and propagates toward the measuring objective 66. This measuring objective 66 detects the light returning from the human skin 71 and directs it partially in transmission toward the beam splitter cube 37, where it is reflected into the detection optical path. The near-surface area of the skin is scanned with a maximum depth of 100 μm. It can be seen from details D44-5 and D44-6 that the objectives counter-oscillate during the measurement process in order to compensate for the restoring forces.

Figure 45:
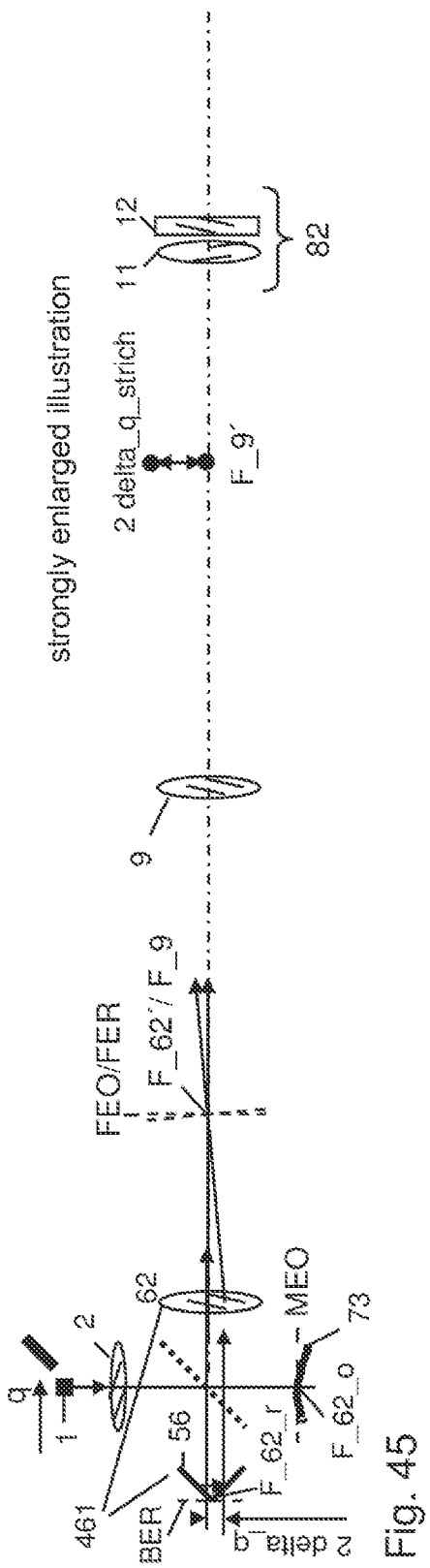
FIG. 45 illustrates an exemplary Michelson interferometer in accordance with one or more aspects of the present disclosure.

FIGS. 45 to 54 illustrate some interferometer arrangements that are technically and economically practical. FIG. 45 illustrates a Michelson interferometer with the usually used output and an object-imaging objective, which is used in single pass. Two tilted wavefronts form in the Fourier plane FEO or in the front focal plane F_9 of the tube objective 9.

Figure 46:
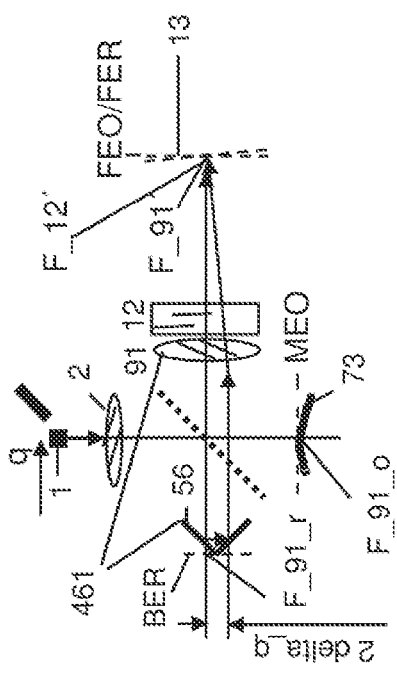
FIG. 46 illustrates an exemplary Michelson interferometer with an objective imaging the object in accordance with one or more aspects of the present disclosure.

FIG. 46 illustrates a Michelson interferometer with the usual output and object-imaging objective.

Figure 47:
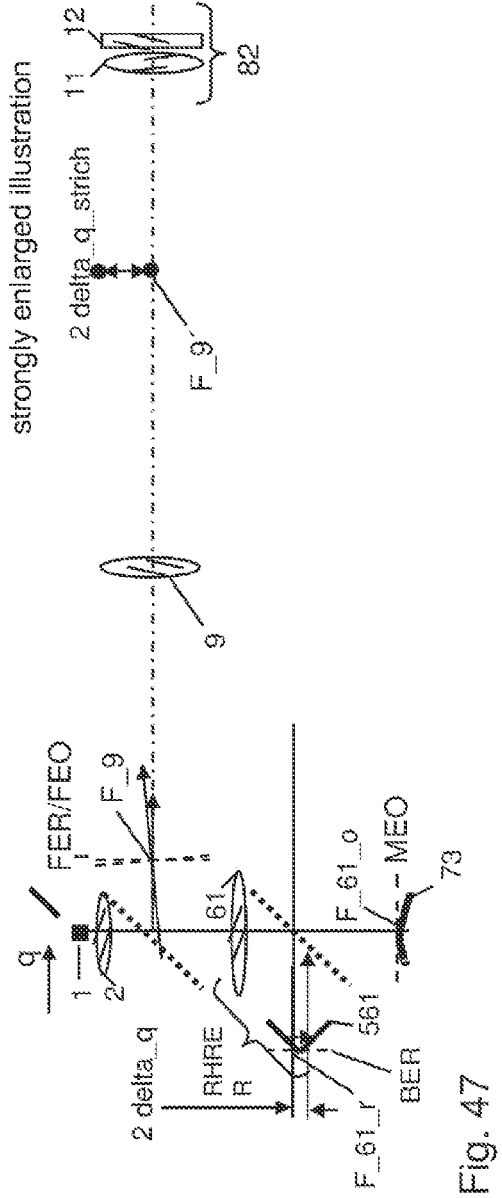
FIG. 47 illustrates an exemplary Michelson interferometer with a g output in accordance with one or more aspects of the present disclosure.

FIG. 47 illustrates a Michelson interferometer with a g output. The effect thereof is identical with a Mirau interferometer. The objective 61 is used in double pass.

Figure 48:
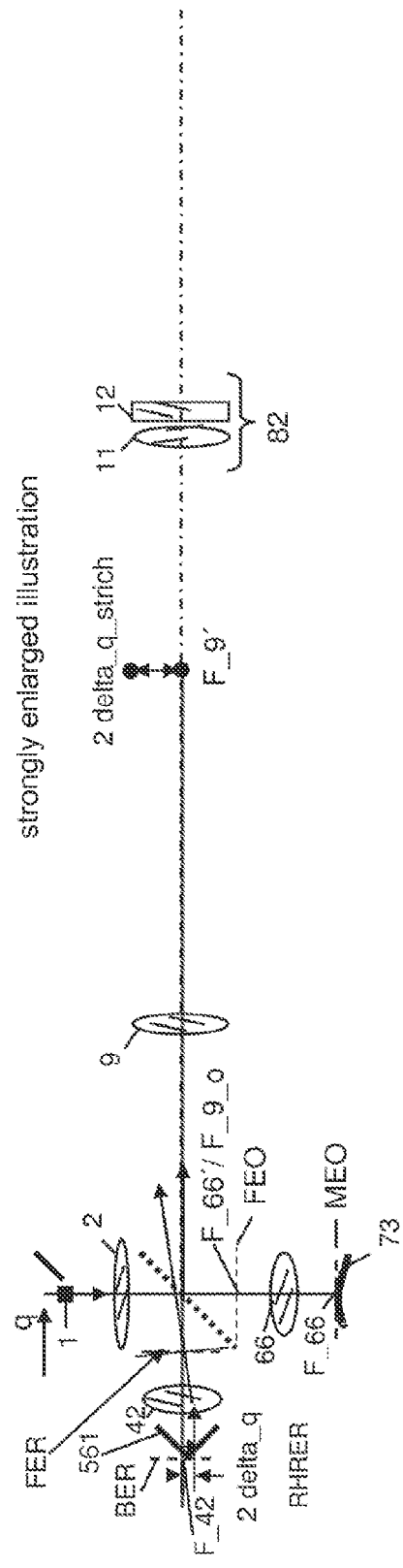
FIG. 48 illustrates an exemplary Linnik interferometer with a "standard" output in accordance with one or more aspects of the present disclosure.

FIG. 48 illustrates a Linnik interferometer with a "usual" output.

FIG. 49 illustrates a hybrid Linnik interferometer. Due to the unequal optical path lengths, a frequency comb light source is used for compensation here.

FIG. 50 illustrates a hybrid Linnik interferometer with rather undesired interferences of the same inclination in the field. Therefore, only a very small field is possible. The hollow roof edge reflector 5 already forms a hybrid retro reference end reflector without an objective and introduces the tilt of the reference wavefront with respect to the object wavefront.

Figure 51:
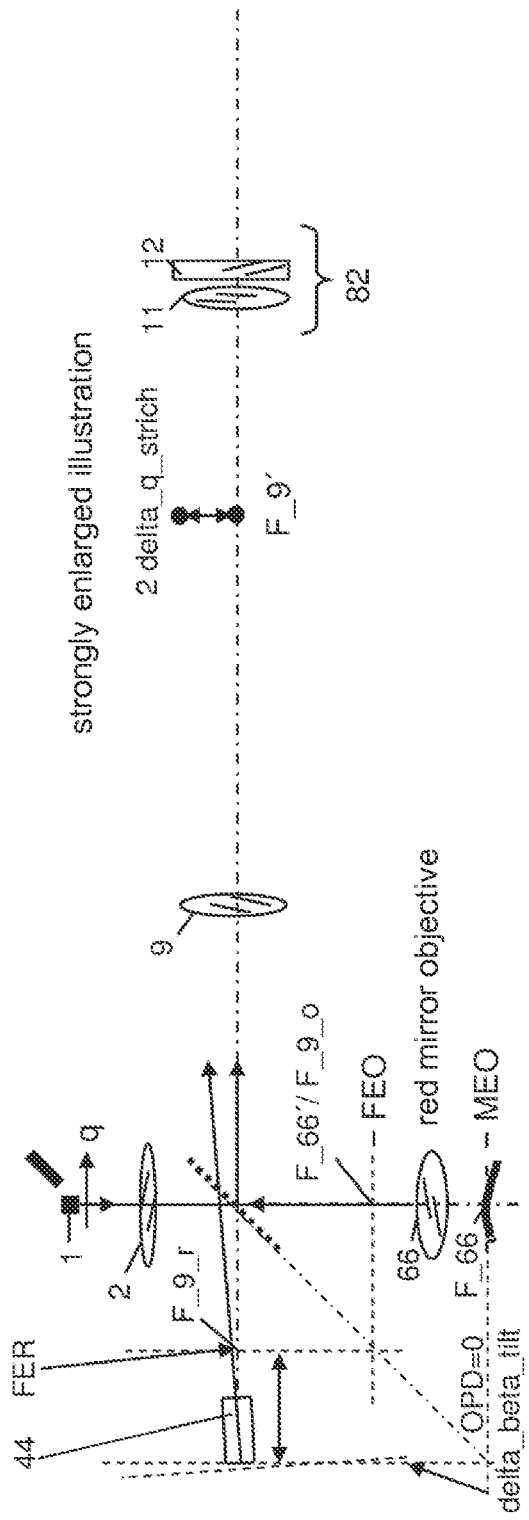
FIG. 51 illustrates an exemplary hybrid Linnik interferometer with cylinder mirror objective and plane end mirror in the reference arm in accordance with one or more aspects of the present disclosure.

FIG. 51 illustrates a hybrid Linnik interferometer with cylinder mirror objective and plane end mirror in the reference arm R.

Figure 52:
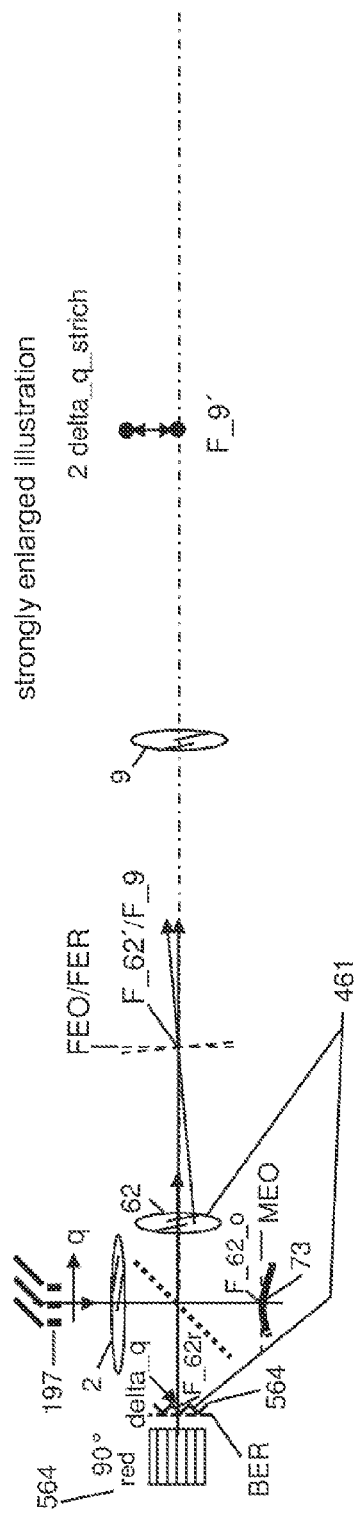
FIG. 52 illustrates an exemplary Michelson interferometer with an object-imaging objective and a tube objective in accordance with one or more aspects of the present disclosure.

FIG. 52 illustrates a Michelson interferometer with "usual" output and object-imaging objective and a tube objective.

Figure 53:
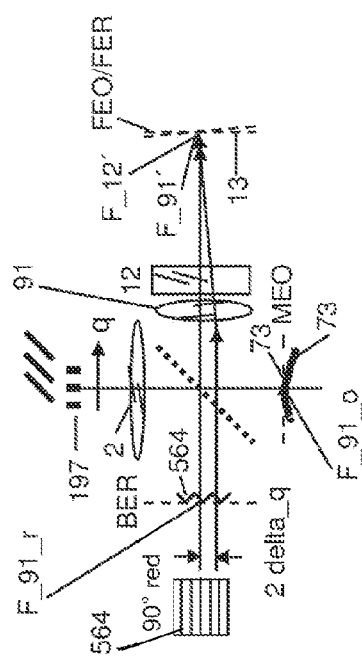
FIG. 53 illustrates an exemplary Michelson interferometer with an object-imaging objective in accordance with one or more aspects of the present disclosure.

FIG. 53 illustrates a Michelson interferometer with usual output and objective imaging the object 73. Alternatively, a triple matrix array may also be used in the reference arm R. In this case, the light source is formed as a matrix point source array. The raster constant in the field is made equal by light source array and triple matrix array.

FIG. 54 illustrates a Michelson interferometer with a g output. The effect of the Michelson interferometer is identical with a Mirau interferometer. The object objective 61 is used dually. Alternatively, a triple matrix array may also be used in the reference arm R. In this case, the light source is formed as a matrix point source array 199. The raster constant in the field is made equal by light source array and triple matrix array.

FIG. 55 illustrates a Linnik interferometer for shape measurement of a small weak asphere. This weak asphere 75 is illuminated in a structured way with a finely formed, rasterized point light source matrix 199 via the object optical path of the Linnik interferometer. The tube lens 9 images the more or less defocused point pattern at the output of the interferometer. The sharp images of the point sources, which are imaged via the reference optical path, form in the focal plane with the focal point F_9' of the tube lens 9. The more or less focused images of the point light sources of the point light source matrix 199, which were imaged via the weak asphere 75, form in the focal plane with the focal point F_9' of the tube lens 9. Behind the microlens array 84, spatial interferograms form on the rasterized detector 13, shown greatly enlarged here, see also detail D55. In the two outer spatial interferograms, it also possible to see the defocus resulting from the curvature of the weak asphere 75, since these surface areas are not located in the DOV anymore. The inclination of the illuminated surface areas of the weak asphere 75 outside the focal plane of the Linnik objective 66 and the offset from the focal plane of the tube lens 9 with the focal point F_9' can be calculated from the interferogram.

Figure 56:
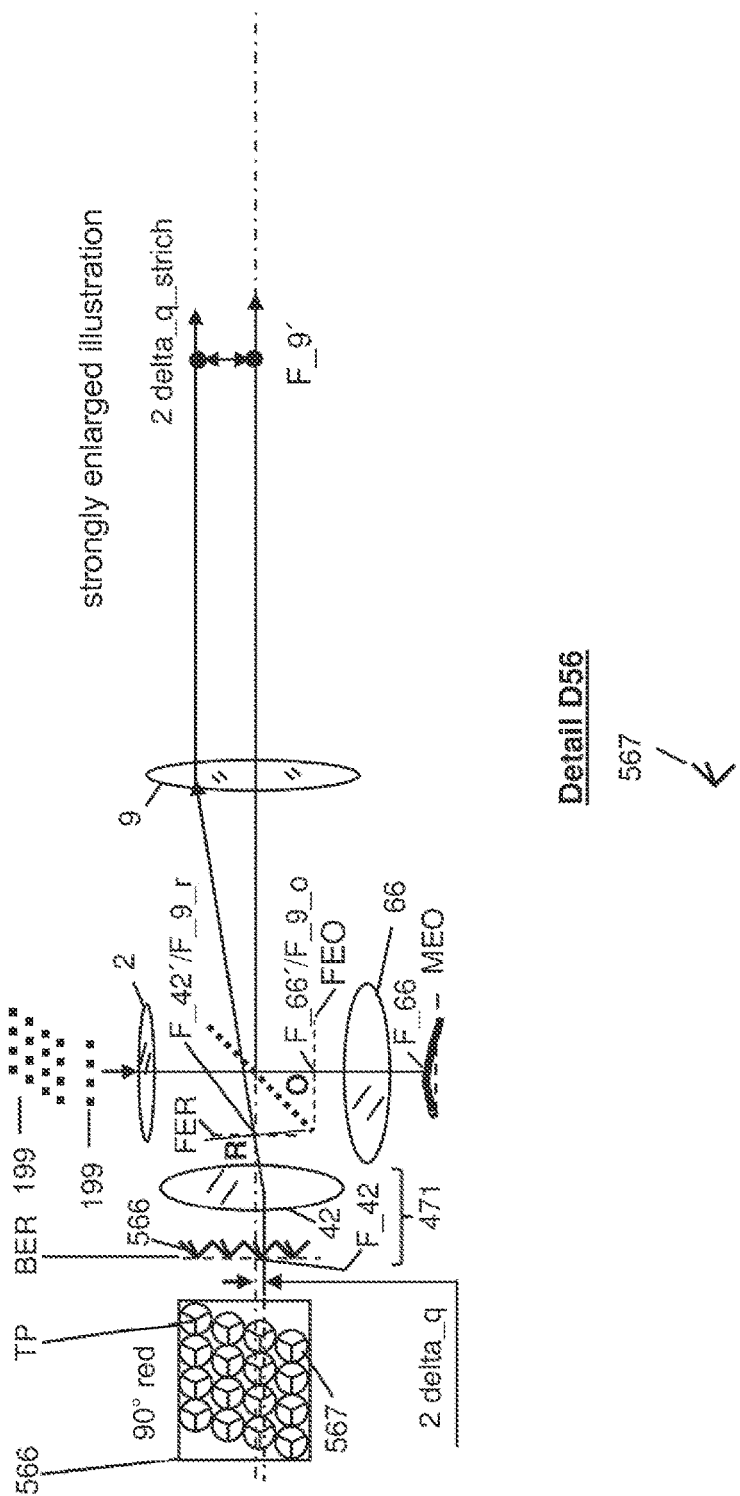
FIG. 56 illustrates an exemplary Linnik interferometer with point light source matrix array and triple array in accordance with one or more aspects of the present disclosure.

FIG. 56 illustrates a Linnik interferometer with point light source matrix array and triple array 566. The triple array 566 forms a full retro reflector system 471 with the objective 42. There are two tilted wavefronts in the Fourier plane of an objective downstream of the reference arm R in the light direction to the detector 13 or in the front focal plane F_9 of the tube objective 9.

Figure 57:
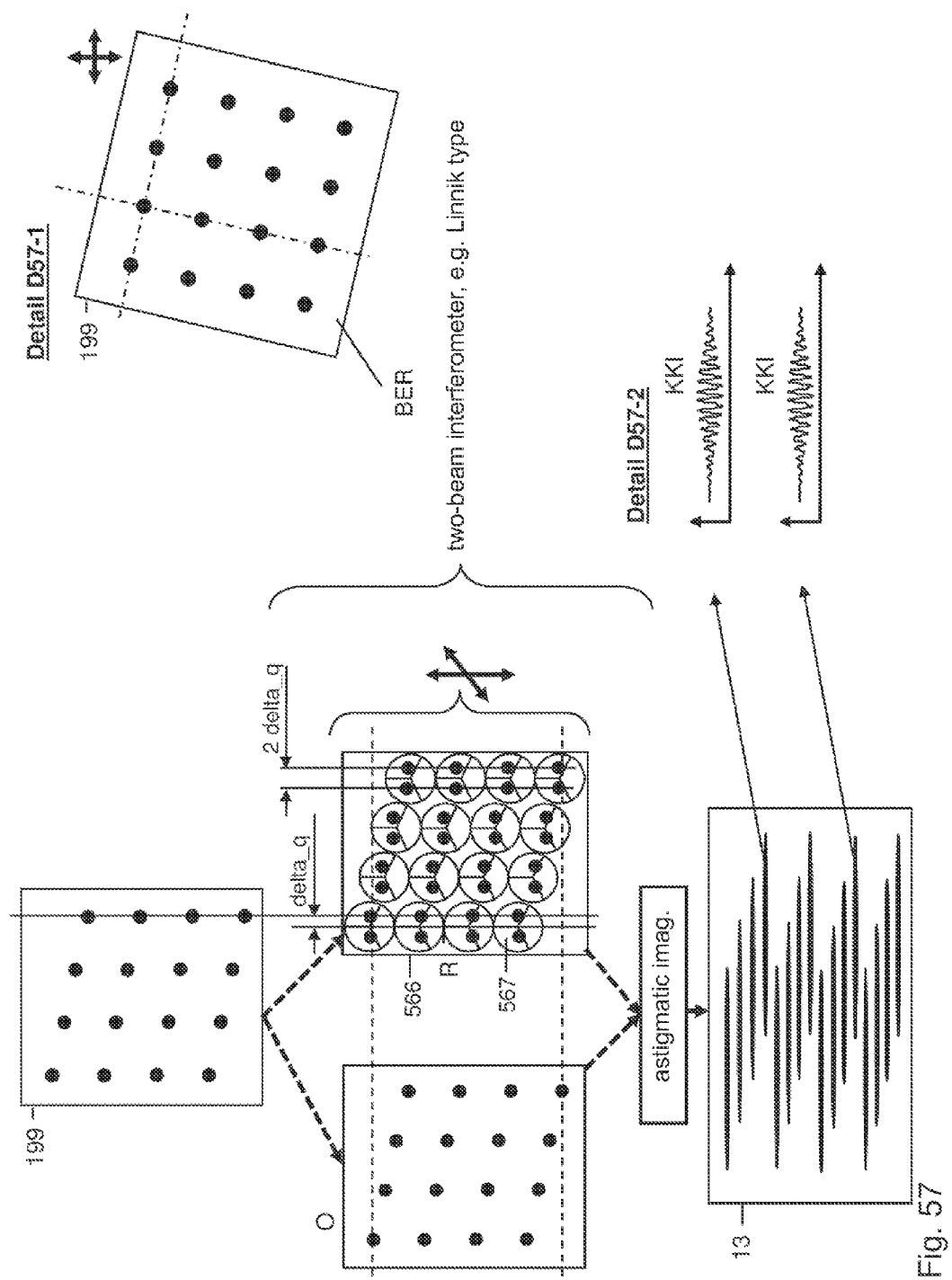
FIG. 57 illustrates an exemplary full retro reference end reflector array with triple reflector in accordance with one or more aspects of the present disclosure.

FIG. 57 illustrates a full retro reference end reflector array with triple reflector. Here, non-illustrated means for a computer-controlled lateral displacement are assigned to the array. The point light source array with light spots below the diffraction-limited resolution is offset laterally to the reference full retro end reflector array. Each light source point is offset laterally by 2delta_q. Details D57-1 and D57-2 illustrate the finely formed point light source matrix 199 and typical short-coherence interferograms, respectively.

Figure 58:
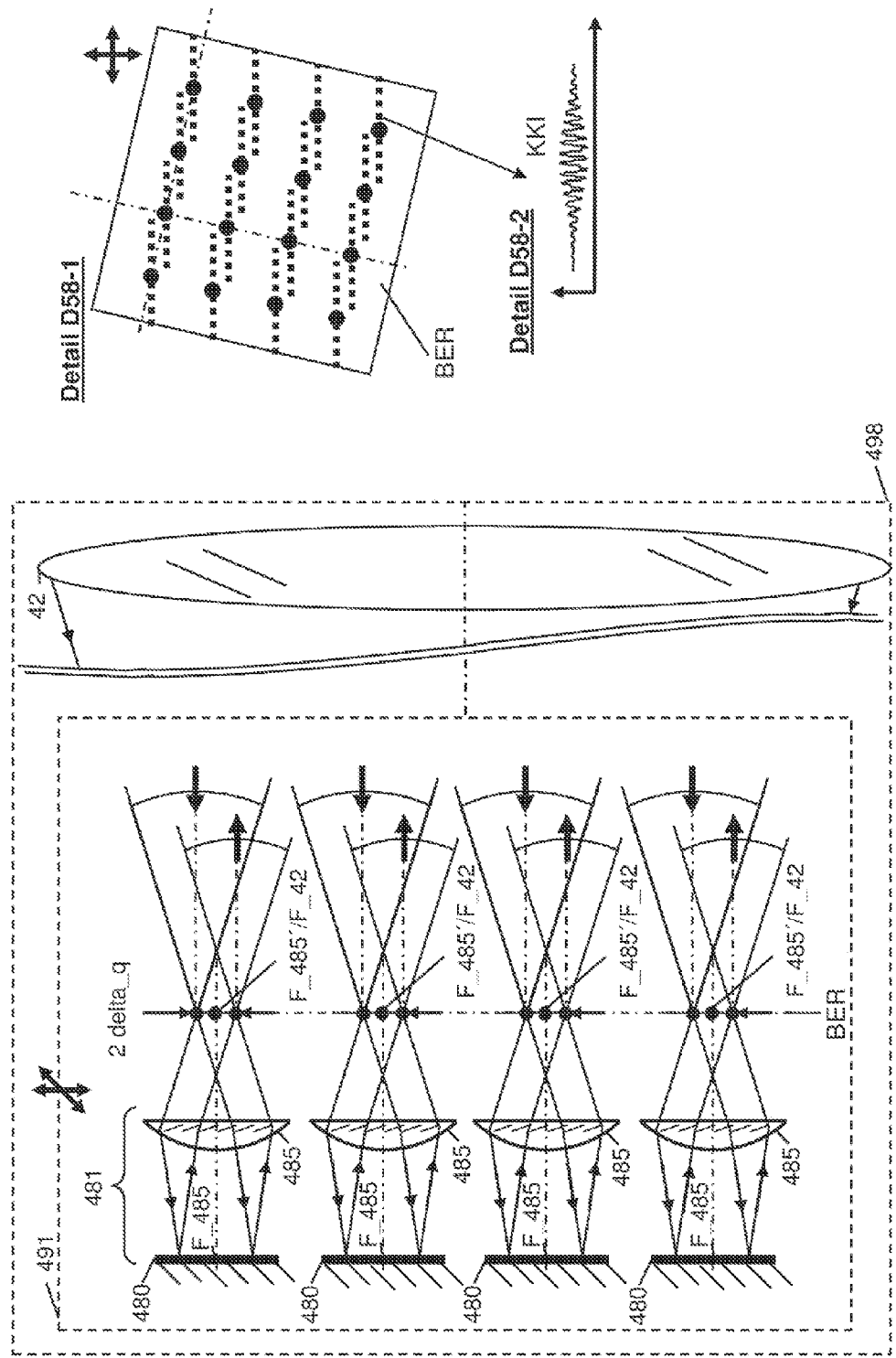
FIG. 58 illustrates an exemplary micro end reflector array system with a micro end reflector array with full retro micro end reflectors of the rotationally symmetric lens cat's eye type in accordance with one or more aspects of the present disclosure.

FIG. 58 illustrates a micro end reflector array system 498 with a micro end reflector array 491 with full retro micro end reflectors 481 of the rotationally symmetric lens cat's eye type. Each full retro micro end reflector is offset by delta_q. The arrangement is formed with a frequency comb light source 103 and a compensation plate 569 in the object arm O. Here, non-illustrated means for a computer-controlled lateral displacement are assigned to 493. Detail D58-1 illustrates the measurement cells on the rasterized detector 13. The patent document DE 10 2006 007 172 B4 indicates the relations for the uninterrupted arrangement of elongated measurement cells on a rasterized receiver, with a rotation of the elongated measurement cells to the receiver matrix.

Figure 59:
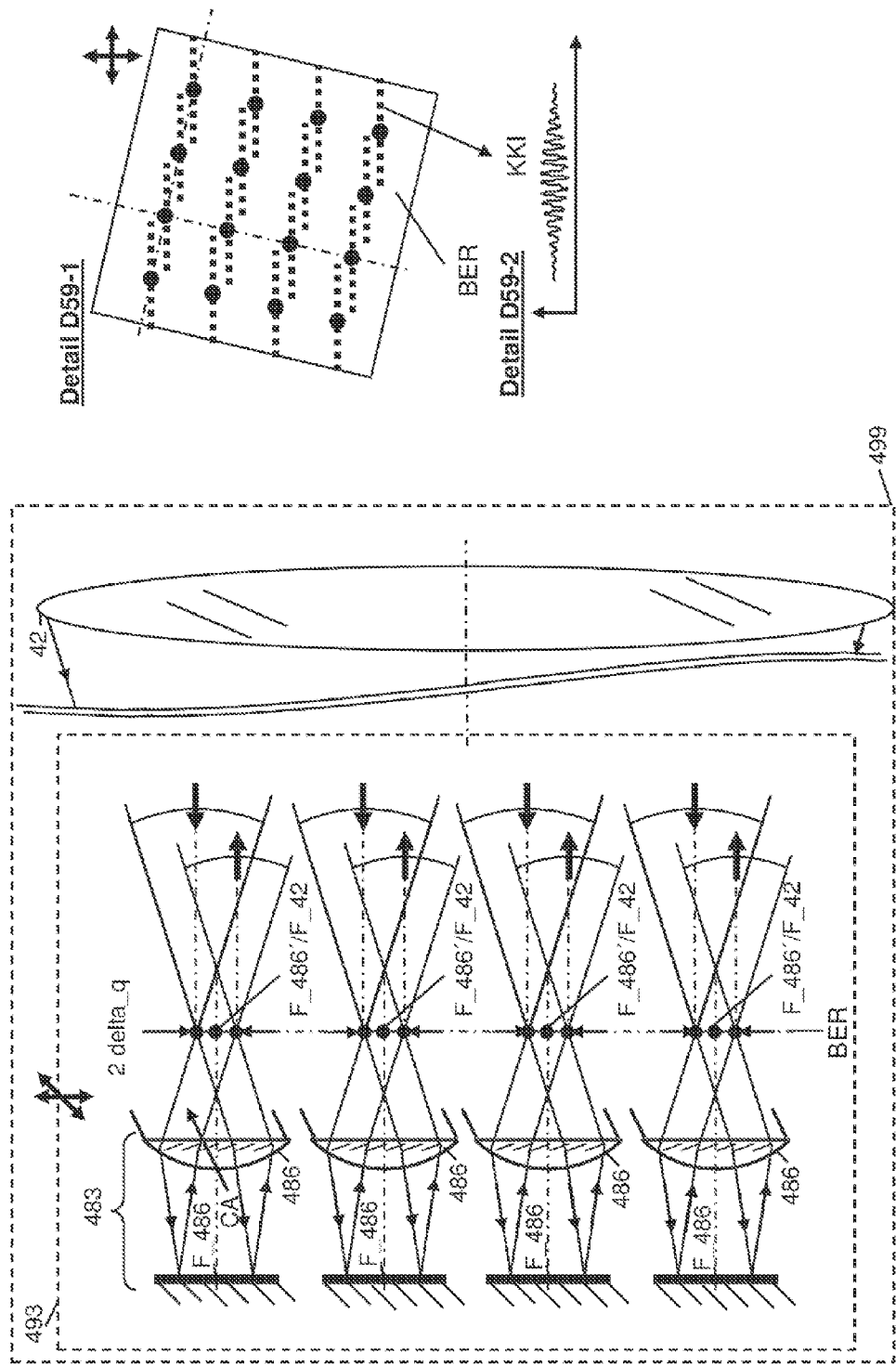
FIG. 59 illustrates an exemplary micro end reflector array system with a micro end reflector array with hybrid retro micro end reflectors of the cylinder objective cat's eye type in accordance with one or more aspects of the present disclosure.

FIG. 59 illustrates a micro end reflector array system 499 with a micro end reflector array 493 with hybrid retro micro end reflectors 483 of the cylinder lens cat's eye type. Each hybrid retro micro end reflector 483 is offset by delta_q. This approach is applied in combination with a frequency comb light source 103 and a compensation plate 568 in the reference arm. The means for a computer-controlled two-dimensional lateral displacement to achieve a full-surface scan of the object are assigned to the micro end reflector array 493, but not illustrated here. Details 59-1 and D59-2 illustrate the measurement cells in their arrangement on the rasterized detector 13 and a detected short-coherence interferogram, respectively.

FIG. 60 illustrates a Mirau interferometer, which can be used for microform measurement. The interferometer is made to be asymmetrical in a predetermined way. A telecentric optical path exits. Illumination is performed by means of short pulses. Due to the asymmetry, as illustrated in FIG. 61, a depth separation def_r-o of image spots results in the detection optical path. FIG. 62 illustrates the light field interferences with different phase positions, which results from the different height positions on the rough metal surface 73. The microlens array 84 can be moved across the rough metal surface 73 in a temporally and laterally synchronized way with the spots of the illumination of the spatial light modulator 104 in order to be able to obtain more single-shot data. The single-shot data from several measurements can be combined in a computerized way by means of feature correlations algorithms.

Figure 63:
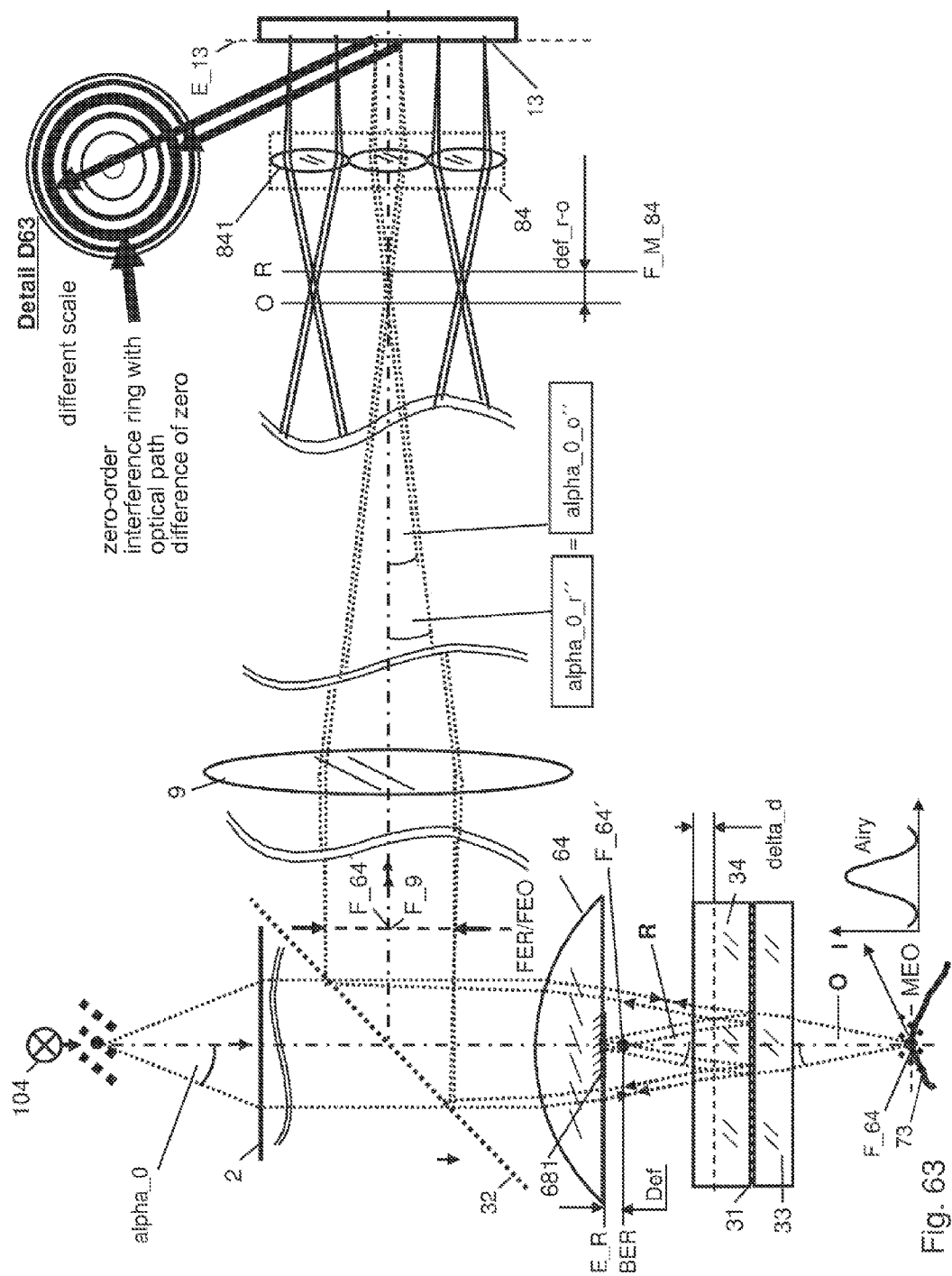
FIG. 63 illustrates the exemplary Mirau interferometer of FIG. 60, with an angle alpha_0 from the angular spectrum of the illumination, for which the optical path difference becomes zero during the detection in accordance with one or more aspects of the present disclosure.

FIG. 63 illustrates the Mirau interferometer of FIG. 60, with an angle alpha_0 from the angular spectrum of the illumination, for which the optical path difference becomes zero during the detection. The detail D63 illustrates the light field interferogram with a zero-order interference ring, which is indicated in bold here. The angle alpha_0_o" is precisely the angle in the object space angular spectrum for which—for a provided object point—the optical path difference in the plane E_13 on the rasterized detector 13 becomes zero. Thus, for this object point, the zero-order interference ring forms approximately in the center of the angular spectrum or interference ring system. Since there is a radial shear to the reference beams, the entire optical system must be correctly very well until detection, in particular also chromatically.

FIG. 64 illustrates an ensemble of light field interferograms—each with a zero-order interference ring—which is captured by a rasterized detector 13.

FIGS. 65 and 66 illustrate short-coherence wavelets with chirping introduced in a predetermined way. The design and the assembly are adjusted to a largest possible deviation SH in short-coherence wavelets with adjustment. The reference point aTS is determined as an alternative trigger threshold for the measurement. Due to the spherical component, the short-coherence wavelet is nonlinear, which must be taken into account explicitly in the evaluation. Each measurement channel on the basis of a spatial interferogram is trained, in a computer-controlled way, to recognize and evaluate its own wavelet in conjunction with a reference measuring object by means of teaching algorithms. The interferometer setup must only be highly stable over time with regard to the employed components and their positions to each other.

FIG. 67 illustrates an interferometer setup that is operated with pulsed illumination, with small mirror objectives 85 as a Fourier transform component in a mirror objective array 86 behind the tube objective 9. The spatial interferograms are formed on the rasterized detector 13 by means of a 4f transfer stage 87, illustrated in FIG. 68. A micro red barrier filter array 89 with micro red barrier filters 891 is arranged in the common focal plane of the 4f transfer stage 87 in order to block reference light in the red spectral range, see FIG. 69, which illustrates the blocking-out of the reference light. In this way, it is possible to detect angular spectra of individual object points after the 4f transfer stage 87 behind the coupling-out beam splitter 36 by means of a camera 132, which is made sensitive solely in the red spectral range by means of a red-transmission filter.

Figure 70:
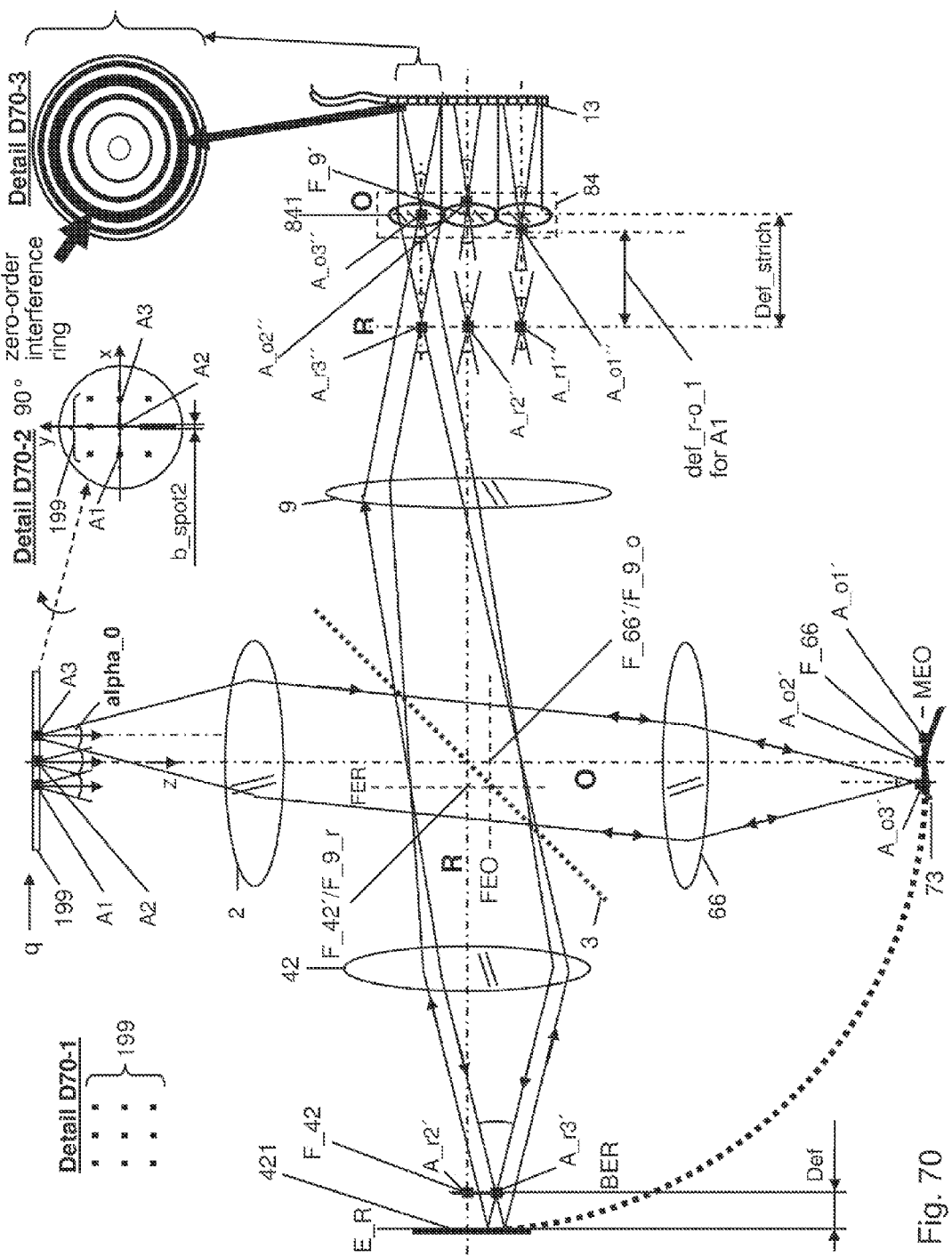
FIG. 70 illustrates an exemplary Linnik interferometer with a finely formed point light source matrix in accordance with one or more aspects of the present disclosure.

FIG. 70 presents a Linnik interferometer with a finely formed point light source matrix 199, illustrated in detail D70-1, wherein detail D70-2 illustrates the position of the point light source matrix 199. Slight defocusing Def is fixedly introduced into the reference arm R as a device constant. This defocusing Def was achieved by a slight displacement of the objective 42 toward the beam splitter 3, from which the ring number results, while when shifting the interferometer end mirror 421 and the objective 42 together, the optical path difference changes, i.e. the zero-order stripe in the interference field moves radially in the spatial interferogram. Here, the Linnik interferometer was adjusted such that for the angle alpha_0 in the angular spectrum of the illumination, during detection on the rasterized detector 13, the zero-order stripe forms approximately in the center of the spatial interferogram, illustrated in detail D70-3 for an individual spatial interferogram. The depth separation def_r-o is determined by the current object point position and the defocusing Def fixedly set in the reference arm R.

Figure 71:
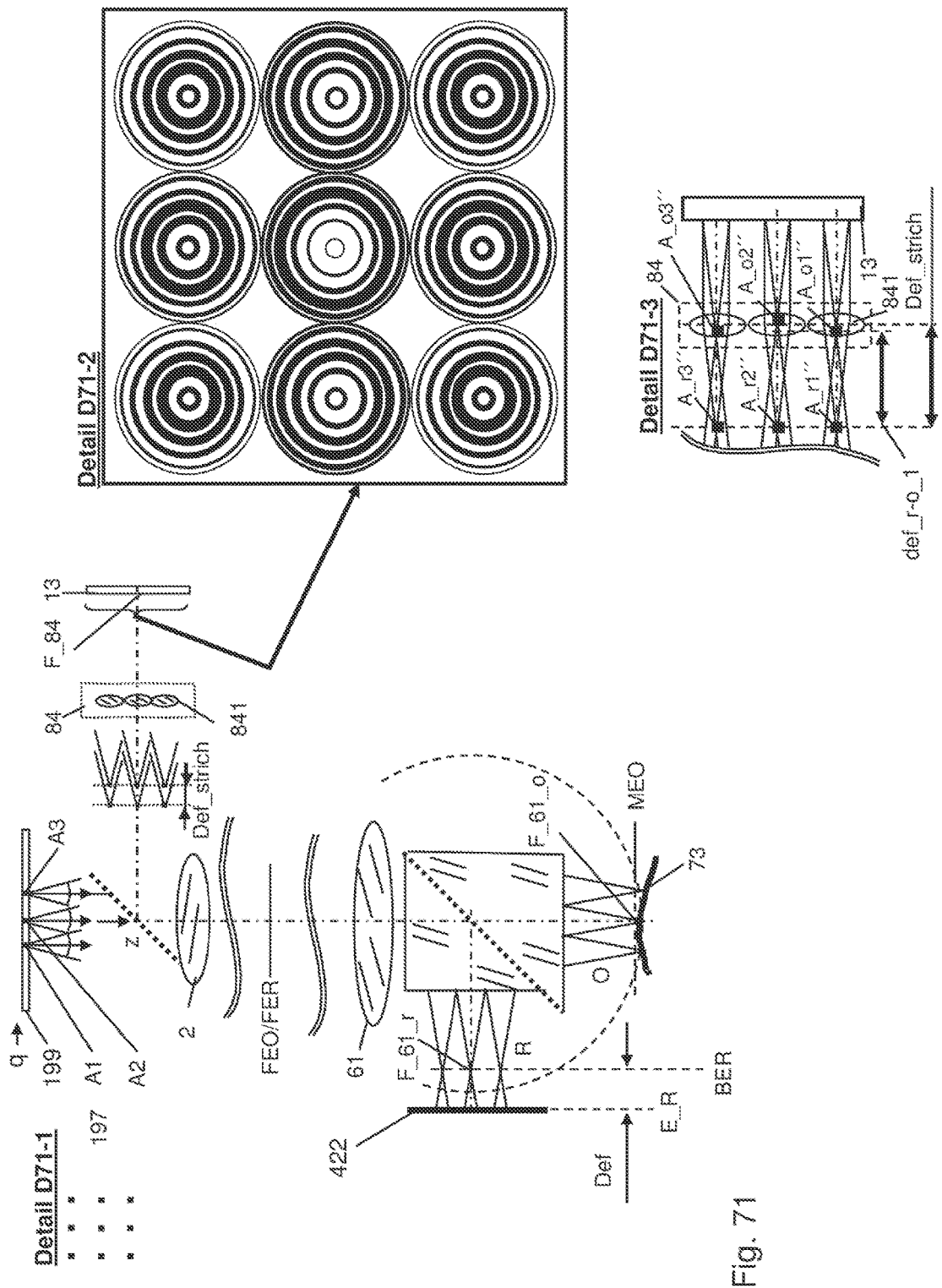
FIG. 71 illustrates an exemplary Twyman Green interferometer in which the desired asymmetry is created by dissimilar optical paths in different optical materials in accordance with one or more aspects of the present disclosure.

FIG. 71 illustrates a Twyman-Green interferometer, in which the desired asymmetry is created by unequal optical paths in different optical materials. Illumination is performed by means of a finely formed point light source matrix 199, see also detail D71-1. There is defocusing Def at the optical path difference of zero in the reference arm R. This causes defocusing Def_strich in the detection optical path. The spatial interferograms, also referred to as light field interferograms here, are imaged onto the rasterized detector 13 by means of a microlens array 84. Detail D71-2 shows the light field interferograms that have different phases in the light field interferograms due to different height positions of the object points. Detail D71-3 illustrates an arrangement with the detector 13 in the Fourier plane of the microlens 841. The image points from the reference arm and the object arm are clearly separated, so that interferograms shown in detail D71-2 can form.

Figure 72:
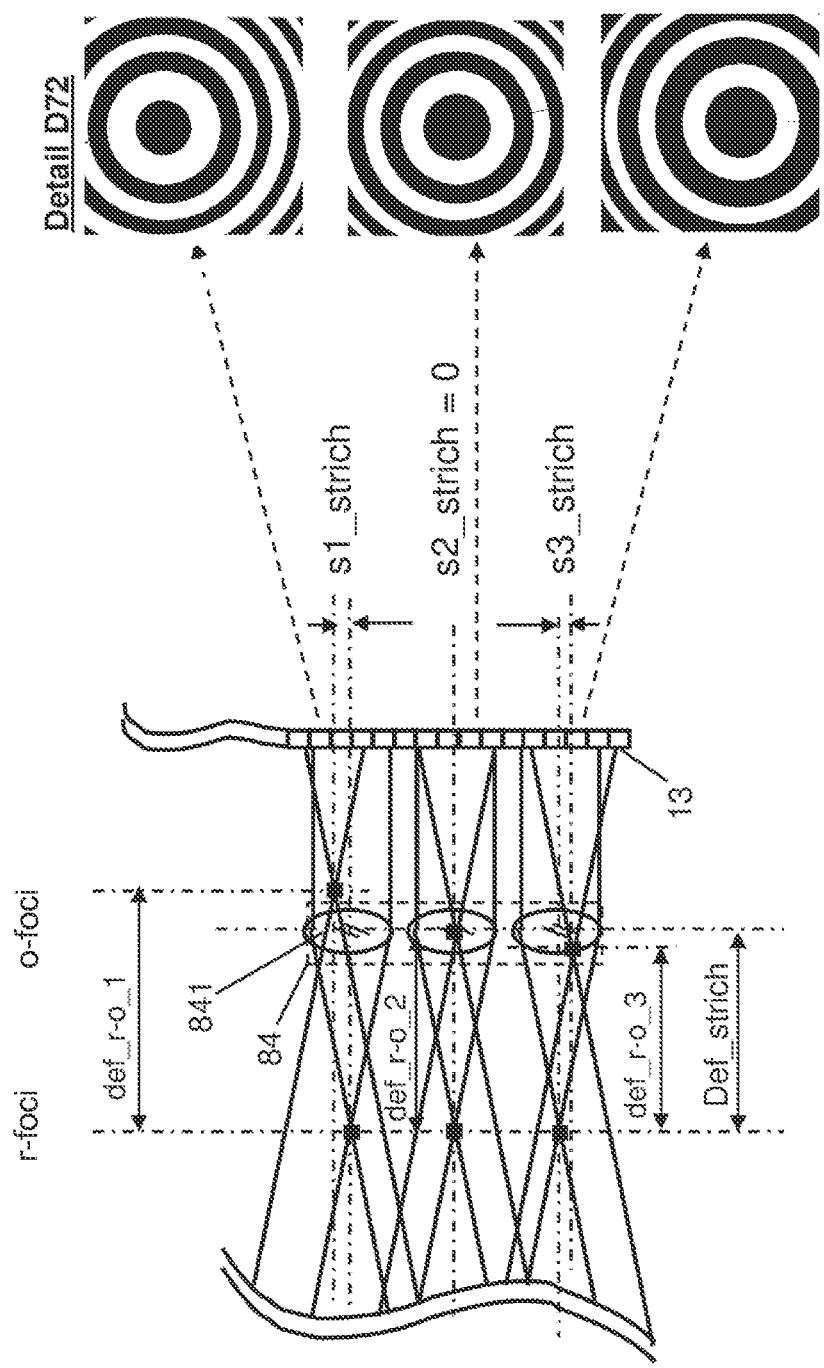
FIG. 72 illustrates an exemplary microlens array in accordance with one or more aspects of the present disclosure.

FIG. 72 illustrates a microlens array 84 with the microlenses 841. This microlens array 84 is arranged in a Twyman-Green interferometer behind the tube objective 9, as is illustrated in detail D71-3 in FIG. 71. The interference in the Fourier plane of the microlens 841 on the rasterized detector 13 is detected. The thus-forming light field interference are illustrated in detail D72. If short-coherent light is used and with a corresponding system design, it also possible to detect a zero-order ring. Also decentered interference ring systems form on the rasterized detector 13, as an optically smooth object with a curved surface, in which a detected subregion of the surface is slightly defocused and thus there is an inclination of the measured surface, is measured. The wavefront from the object, which is brought to a state of interference, carries also always the information on the object shape itself in the case of defocusing in the object illumination in the interferometer, so that the object wavefront is also aspherical in the interference on the rasterized detector 13 for an aspherical defocused object.

Figure 73:
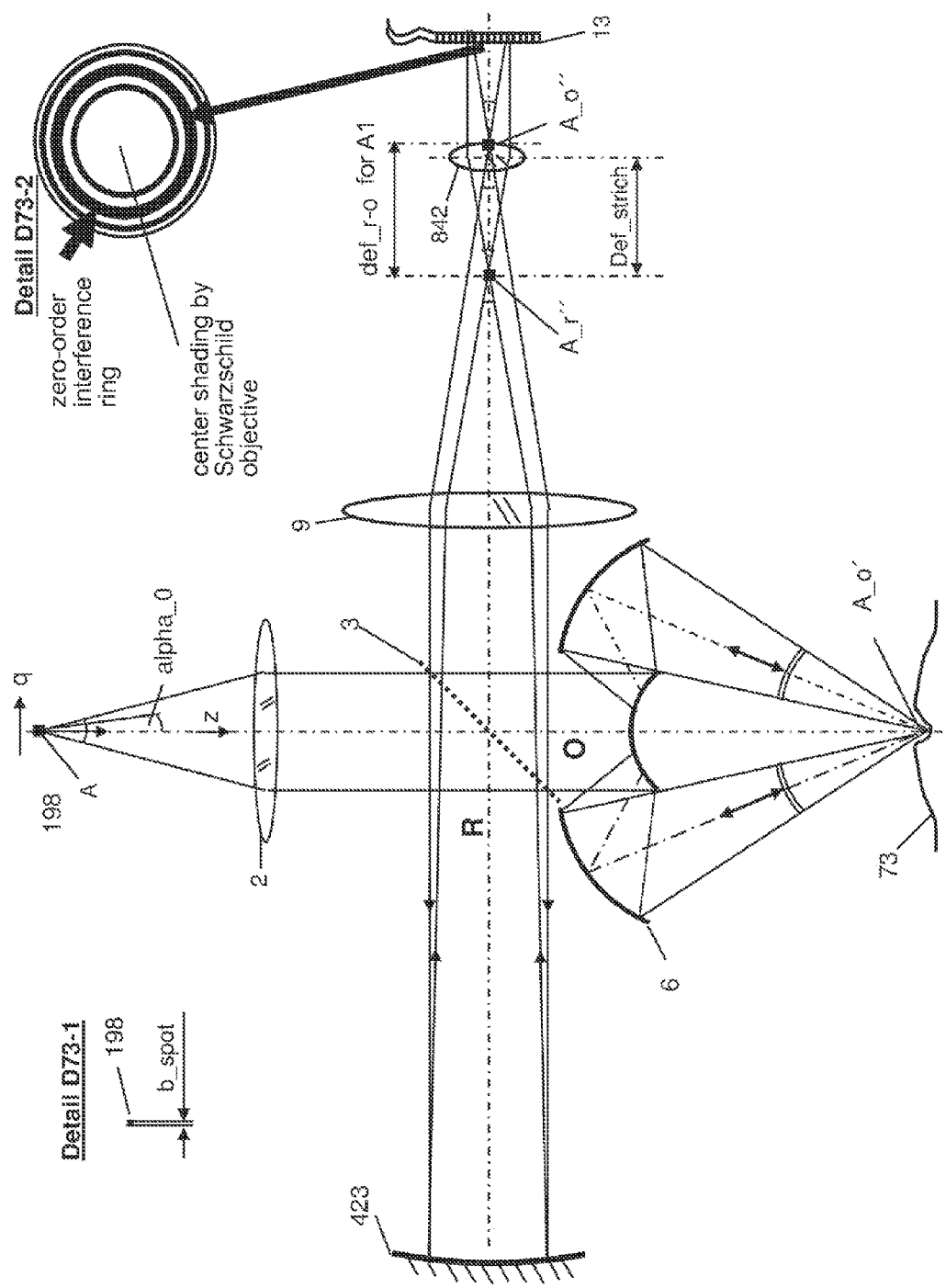
FIG. 73 illustrates an exemplary two-beam interferometer with an object-imaging Schwarzschild objective in the object arm in accordance with one or more aspects of the present disclosure.

FIG. 73 illustrates a two-beam interferometer with an object-imaging Schwarzschild objective 6 in the object arm O. The point light source 188 generates a fine light spot, the lateral extension b_spot of which being below the diffraction-limited resolution of the following collimator objective 2, see also detail D73-1. The light source 188 is formed with a frequency comb light source not illustrated here. This frequency comb light source exhibits an optical delay length Y, which is at least approximately made equal to the optical path difference in the interferometer, or the optical path difference in the interferometer is an integer multiple of the optical delay length y. A concave, rotationally symmetric mirror 423 with a slight curvature is arranged in the reference arm R. The ring number on the rasterized detector 13 results from the curvature in cooperation with the two-beam interferometer.

The geometry of the two-beam interferometer is matched to the frequency comb light source such that in the detection on the rasterized detector 13, with a position of an object in the center of the wave-optical depth of field, the zero-order stripe forms approximately in the center of the spatial interferogram, illustrated in detail D73-3. The depth separation def_r-o is determined by the current object point position and the mirror curvature fixedly specified by the concave, rotationally symmetric mirror 423 in the reference arm R.

FIGS. 74 and 75 each illustrate a miniaturized variant of the single-shot approach in the form of a multi-channel Linnik interferometer solely with optical systems in array form.

FIG. 74 shows how the light going out from a line light source 189 with fine light spots A1, A2, A3 is collimated through the micro collimator objectives of a line-like array 23. Here, this light is generated by means of spectrally broadband, powerful LEDs, which have a downstream pinhole each. The pinhole size is below the diffraction-limited resolution of the following micro collimator objective of the line-like array 23. Reference and object beam bundles form at the beam splitter 3 of the multi-channel Linnik interferometer. In the reference arm R with a line form-type microlens array 401 with rotationally symmetric microlenses 407, there is a fixedly set, slight defocusing Def. The multi-channel Linnik interferometer is adjusted such that the foci in the reference arm R at the optical path difference of zero are in an intrafocal position. The reflected light bundles are weakly convergent and, after the beam splitter 3, hit the tube microlenses 907 of the line-like microlens array 901. Due to the slight defocusing Def in the reference optical path, in the case of an object point position in the wave-optical depth of field of the object arm O, a clear separation of the foci def_r-o of object O and reference arms R is provided in the detection optical path as a result. Thus, an interference figure with rings and also a zero-order interference ring forms on the rasterized detector 13 from each detected object point in the wave-optical depth of field in the plane of the detection. To this end, the Fourier planes of the microlenses of the microlens array 401 are at least approximately imaged sharply onto the rasterized detector. The detail D74 shows the forming interference figures, illustrated exemplarily for the three channels here. Depending on the depth position of an object point of the object, a different position results for the zero-order interference ring, which is evaluated by means of a computer program.

In addition to FIG. 74, FIG. 75 illustrates the approach in an areal arrangement with 3×3 measurement channels. The detail D75 shows the interference figures, illustrated exemplarily for the nine measurement channels here. Only the nine microlenses of the illumination array 24 and of the tube array 902 were presented here for illustrative purposes only. Depending on the current depth position of an object point, also a different position results for the zero-order interference ring due to the then-existing optical path difference.

A particularly stable formation for the multi-channel Linnik interferometer results for the arrangements in FIGS. 74 and 75, which is not illustrated here, if the beam splitter is formed as a compact beam splitter cube and the microlens arrays 401 and/or 402 and the plane interferometer end mirror in the reference arm 424 are rigidly connected to the beam splitter in cube form by gluing or luting. The advantage of this arrangement is that there are no additional glass paths both in the reference arm R and in the object arm O. This allows using microlenses having a comparably high numerical aperture, for example also microlenses having a numerical aperture of 0.5.

FIG. 76, according to ref. [11], image 6, illustrates a multi-channel Mirau interferometer approach. It may be comprised of a miniaturized interferometer arrangement also according to FIG. 60 and a common coupling-out beam splitter 32 and a tube microlens array 901 according to FIGS. 74 and 75. Also in the multi-channel Mirau interferometer, just like in the multi-channel Linnik interferometer, the Mirau interferometer components can be connected rigidly to each other, since there does not need to be a shift of components of the Mirau interferometer with respect to each other for one-shot single formation in principle.

In the multi-channel Mirau, compared to the multi-channel Linnik interferometer, there is no necessity for a precise microlens pupil adjustment, incorrect positions of the microlens pupils may lead to wavefront errors and to decentered interference rings in the Linnik interferometer.

The detail D76 shows a single Mirau interferometer, i.e. a single measurement channel, of the array interferometer arrangement, also referred to as a multi-channel interferometer arrangement, according to FIG. 76. The beam splitter plate 391 and the compensation plate 34 are made of the same glass material BK7 and have only slightly different geometric thicknesses with d_o and d_r, for example a thickness difference in the lower two-digit micrometer range. The resulting focus shift causes a focus spot shifted toward the plane reference mirror 681. In this way, the object wave is always overlaid with a slightly curved reference wave after reflection in the return path of the light in the focal plane F_654', the Fourier plane. This Fourier plane is imaged onto the rasterized detector 13 in each measurement channel. Matching of the Mirau interferometers with d_o and d_r as well as the existing numerical aperture and the main wavelength is performed such that for the focus position of the object points in the center of the wave-optical depth of field, one zero-order ring results at least approximately at half the radius of the largest detectable ring each.

Further examples include:

Example 1

An assembly for robust one-shot interferometry, comprising a light source, a rasterized detector with receiver elements for electromagnetic radiation, and a two-beam interferometer having reference and object arms with the following components:

a light source objective following or downstream of the light source, for imaging same in an at least approximately diffraction-limited way, an objective imaging the object, wherein in the reference arm of the two-beam interferometer there is arranged an end reflector formed as a retro end reflector, which is designed to generate one or more tilted reference wavefronts; and/or there are arranged means for defocusing the reference light, wherein the two-beam interferometer is designed to generate at least a pair of mutually tilted and/or differently curved reference and object wavefronts and to make them interfere.

The end reflector may be part of the means for defocusing the reference light. Thus, either a full or a partial retro reflection with transverse offset and/or slight defocusing of reference light takes place in the reference arm of the interferometer, wherein structured or confocal illumination can be used. In the detection process, a plurality of spatial interferograms (e.g. a plurality of circular spatial interferograms) is formed by making an inclined and/or curved reference wavefront interfere with an object wavefront for each measurement point. The resulting spatial interferograms are detected in a single detector frame and are evaluated by means of a computer program.

Example 2

The assembly according to example 1, further comprising optical means for introducing astigmatism into the detection optical path, which are assigned to or downstream of the objective for imaging the object and which are upstream of the rasterized detector, wherein the wavefronts that are brought to a state of interference have at least approximately a cylinder shape and are formed by the optical means for introducing astigmatism into the detection optical path.

Example 3

The assembly according to example 1 or 2, wherein
the light source is at least one line light source formed to be narrow in a transverse axis direction (q) or a line light source array formed with a plurality of at least approximately parallel line spots formed to be narrow in a transverse axis direction, and for the following light source objective in this transverse axis direction, the line light source or the line spots of the line light source array is/are each formed to be narrow in a transverse axis direction such that it is/they are at least approximately equal to or below the diffraction-limited lateral resolution thereof, wherein the lateral resolution is determined by the numerical aperture of the light source objective and by the employed wavelength of light or by the employed wavelengths of light of the line light source or the line light source array, and wherein at least approximately diffraction-limited imaging of the line light source or of the line spots of the line light source array onto the object is performed by means of the object-imaging objective.

Example 4

The assembly for robust one-shot interferometry according to example 3, wherein
(i) the end reflector is a hybrid retro reference end reflector and the hybrid retro reference end reflector has at least one 90° roof edge end reflector, wherein the roof edge of the 90° roof edge end reflector is positioned at least approximately in the focal plane of a reference objective arranged in the reference arm, or of an objective arranged outside the reference arm; and
is arranged at least approximately perpendicular to the transverse axis direction if no focusing reference objective is arranged in the reference arm; or is arranged at least approximately parallel to the transverse axis direction if a focusing reference objective is arranged in the reference arm; and
there is a transverse offset delta_q of the roof edge at least approximately parallel to the direction of the transverse axis direction either in the focal plane of the reference objective assigned to the hybrid retro reference end reflector or in the focal plane (BER) of an objective assigned both to the reference arm and to the object arm,
the transverse offset delta_q is at most equal to the tenth part of the focal length of this objective and at least equal to or greater than the objective-based Airy disk radius for the main wavelength in the detected spatial interferogram;
or
(ii) the end reflector is a hybrid retro reference end reflector, which is formed either as a cylinder optics hybrid retro reference end reflector with a cylinder objective having a cylinder axis and a plane mirror in the focal plane of the cylinder objective, wherein the cylinder axis is respectively perpendicular to the transverse axis direction, or which is formed as a roof edge reflector, wherein there is a preferably comparably slight tilt (delta_beta_tilt) of the hybrid retro reference end reflector about a tilt axis that is at least approximately perpendicular to both the transverse axis direction and to the direction of light propagation, in each case based on an unfolded optical path of the two-beam interferometer, and
wherein the tilt angle is at most equal to or smaller than 6 degrees (6°) and at least equal to or greater than half a main wavelength in the detected spatial interferogram, based on the illuminated pupil diameter of the objective at the interferometer output;
or
(iii) the end reflector is a hybrid retro reference end reflector, wherein the hybrid retro reference end reflector is formed either as a micro reference end reflector array with hybrid retro micro reference end reflectors of the roof edge mirror type or roof edge prism type or as a micro reference end reflector array with hybrid retro micro reference end reflectors of the cylinder lens cat's eye type or of the cylinder mirror cat's eye type, and
there is a transverse offset (delta_q) of the hybrid retro micro reference end reflectors of the cylinder cat's eye type or of the roof edge type in the micro reference end reflector array either in the focal plane of a reference objective arranged in the reference arm and assigned to the hybrid retro reference end reflector, or in the focal plane of an objective arranged outside the reference arm and assigned both to the reference arm and to the object arm, and
the transverse offset (delta_q) is at least approximately parallel to the direction of the transverse axis direction and at most equal to the tenth part of the focal length of this reference objective or of the objective arranged outside the reference arm, and at least equal to or greater than the objective-based Airy disk radius for the main wavelength in the detected spatial interferogram.

A hybrid retro micro reference end reflector may be a reflector that reflects (back) an incident beam (in the geometrical-optical model) parallel to itself independent of its angle of incidence only in one single marked plane of incidence. For example, a hybrid retro micro reference end reflector may be set up by means of a miniaturized roof edge mirror, a miniaturized roof edge prism, or a miniaturized focusing system with refractive or reflective miniaturized cylinder optical system and downstream mirror. The above-mentioned marked plane of incidence is either perpendicular to the roof edge or perpendicular to the cylinder axis of the cylinder optical system. Roof edge mirrors are always hollow mirrors in this case.

A hybrid retro micro reference end reflector may also be referred to as a one-dimensionally acting retro reflector or (micro) retro reflector (cf. e.g. EP 0 929 978 B1, para. 0038, line 1, component 22).

Example 5

The assembly for robust one-shot interferometry according to example 1, wherein
the light source is at least one point light source or a point light source matrix with a plurality of spots, wherein the point light source or the spots of the point light source matrix is/are each formed to be so fine that for the following light source objective it is/they are at least approximately equal to or below the diffraction-limited lateral resolution thereof, wherein the lateral resolution is determined by the numerical aperture of the light source objective and by the employed wavelength of light or by the employed wavelengths of the light source or the point light source matrix, and
the end reflector is formed as a full retro micro reference end reflector system with a reference objective and with full retro micro reference end reflectors respectively in either a micro end reflector array with full retro micro reference end reflectors of the rotationally symmetric lens cat's eye type or a micro end reflector array with full retro reference micro end reflectors of the rotationally symmetric mirror cat's eye type;

or a micro triple prism mirror end reflector array with micro triple prism mirror micro end reflectors;

or a micro hollow triple mirror end reflector array with micro triple mirror end reflectors and in the micro end reflectors, respectively a transverse offset delta_q exists in the focal plane of the associated reference objective, said transverse offset being made at most equal to the tenth part of the focal length of this reference objective and at least equal to or greater than the objective-based Airy disk radius for the main wavelength in the detected spatial interferogram.

A full retro micro reference end reflector may be a miniaturized retro reflector that reflects (back) any incident beam (in the geometrical-optical model) at least approximately parallel to itself independent of its angle of incidence and its azimuthal orientation. For example, a full retro micro reference end reflector may be set up with a miniaturized hollow triple mirror, or a miniaturized triple prism, or a miniaturized focusing system (with refractive or reflective or mirror lenses) with a reflective surface through the focal point facing away. Here, the distance from a marked point of the full retro micro reference end reflector (triple point, spatial corner point, or front focal point of the focusing system) of the outgoing beam is equal to that of the returning beam. Triple mirror systems (hollow mirrors) are also referred to as trihedral mirror optical systems. By contrast, cat's eye arrangements are a special case of the retro reflector with focusing and mirror optical systems.

Example 6

The assembly for robust one-shot interferometry according to at least one of the above examples, wherein the light source is a light source according to example 2, and wherein the direction of the longitudinal axes of the cylinder wavefronts is respectively at least approximately made to coincide with the transverse axis direction in the unfolded optical path of the two-beam interferometer, and the tilt axis of the at least one reference wavefront is respectively arranged at least approximately perpendicular to the transverse axis direction (q).

Example 7

The assembly for robust one-shot interferometry according to at least one of the above examples, wherein the light source is rasterized, and wherein the raster constant of rasterized light source and rasterized reference end reflector array, based on the focal plane of the tube objective or on the focal plane of the object-imaging objective, is at least approximately equal.

Example 8

The assembly for robust one-shot interferometry according to example 1,
wherein the light source is a point light source or a point light source matrix with a plurality of spots, and
wherein
the point light source or the spots of the point light source matrix is/are each formed to be so fine that for the following light source objective it is/they are at least approximately equal to or below the diffraction-limited lateral resolution thereof, wherein the lateral resolution is determined by the numerical aperture of the light source objective and by the employed wavelength of light or by the employed wavelengths of the finely formed light source or the finely formed point light source matrix, there is asymmetry in the two-beam interferometer, which is caused by different travel paths of the light in different materials of different refractive power; and/or by refractive powers of optical components distributed, which are distributed unevenly in the two interferometer arms; and/or by components with refractive power positioned unevenly in the depth of the two interferometer arms; and in the space behind the tube objective or an at least approximately focusing objective or an at least approximately focusing objective from the illuminating optical path, which is also used for detection, there are two separated focal planes in depth, which are at least approximately separated from each other by an amount Def_strich in a predetermined way, wherein the amount Def_strich is at least equal to or greater than half the main wavelength lambda_S in the detected signal of spatial interferograms divided by the square of the effectively used numerical aperture of the tube objective (9) or of the at least approximately focusing objective or of the at least approximately focusing objective from the illumination optical path, which is also used for detection, and the amount Def_strich is smaller than the focal length of the tube objective or of an at least approximately focusing objective or of the at least approximately focusing objective from the illumination optical path, which is also used for detection.

Example 9

The assembly for robust one-shot interferometry according to example 8, wherein in the image plane of the two-beam interferometer, an optical array with elements of positive or negative refractive power is arranged in the style of a light-field camera or plenoptic camera, and each pair consisting of a diffraction-limited image spot from the reference arm and the object arm, which each represent coherent spots, is assigned at least one of these elements of positive or negative refractive power.

Preferably, the optical array with elements of positive or negative refractive power is formed to be slightly curved at least approximately. Moreover, the focal length of the elements of positive or negative refractive power in the array may correspond at least approximately to the predetermined depth separation (Def_strich). The focused object image spots may be located at least approximately in the pupil of the elements of positive or negative refractive power in the array.

Example 10

The assembly for robust one-shot interferometry according to at least one of examples 8 or 9, wherein there is at least approximately the optical path difference of zero in the two-beam interferometer.

Example 11

The assembly for robust one-shot interferometry according to at least one of the above examples, wherein the array in the detection optical path is formed with diffractive optical elements on the basis of a switchable spatial light modulator.

Example 12

A method for robust one-shot interferometry, comprising:
providing an assembly for robust one-shot interferometry according to one of the above examples,
introducing, in the focal plane upstream of a detector objective, a transverse offset of mutually coherent light spots or foci or image points from the reference and object arms and/or introducing a depth separation of mutually coherent light spots or foci or image points from the reference and object arms;
forming and bringing to a state of interference, in the plane of the rasterized detector, at least a pair of wavefronts, one from the object arm and one from the reference arm, wherein the wavefronts in the pair are tilted with respect to each other and/or are curved differently;
forming at least one spatial interferogram and detecting said interferogram (KKI) by means of the rasterized detector.

Example 13

A method for robust one-shot interferometry, comprising:
providing one with an assembly for robust one-shot interferometry according to one of the above examples,
introducing, in the focal plane upstream of a detector objective, a transverse offset 2 delta_q_strich or 2 delta_q of mutually coherent light spots") from the reference and object arms by means of the end reflector,
forming and bringing to a state of interference, in the plane of the rasterized detector, at least two mutually tilted interfering wavefronts, one from the object arm and one from the reference arm, wherein the wavefronts have at least approximately a cylinder shape, and wherein the wavefronts are formed and brought to a state of interference by optical means, upstream of the rasterized detector, for introducing astigmatism into the detection optical path, which are assigned to or downstream of the objective for imaging the object,
forming at least one spatial interferogram and detecting said interferogram by means of the rasterized detector.

Example 14

The method for robust one-shot interferometry according to example 12 or 13, wherein
the assembly is an assembly according to example 2, the transverse offset 2 delta_q_strich or 2 delta_q in case (i) is introduced by the transverse offset delta_q of the roof edge of the 90° roof edge end reflector; and in (ii) is introduced by the tilt delta_beta_tilt of the hybrid retro reference end reflector; and respectively two mutually tilted interfering wavefronts, one from the object arm and one from the reference arm (R), which have at least approximately a cylinder shape, are formed and made to interfere; or
the assembly is an assembly according to example 3, the transverse offset 2 delta_q or 2 delta_q_strich is introduced by the transverse offset delta_q of the hybrid retro reference micro end reflectors, and a plurality of respectively two mutually tilted interfering wavefronts, one from the object arm and one from the reference arm, wherein the wavefronts have at least approximately a cylinder shape, are formed and made to interfere; or
the assembly is an assembly according to example 4, the transverse offset 2 delta_q or 2 delta_q_strich is introduced by the transverse offset delta_q of the micro end reflectors in the focal plane of the associated reference objective, and a plurality of respectively two mutually tilted interfering wavefronts, one from the object arm and one from the reference arm, wherein the wavefronts have at least approximately a cylinder shape, are formed and made to interfere.

Example 15

The method for robust one-shot interferometry according to one of examples 12 to 14 and example 2, wherein the direction of the longitudinal axes of the cylinder wavefronts is respectively at least approximately made to coincide with the transverse axis direction (q) in the unfolded optical path of the two-beam interferometer, and the tilt axis of the at least one reference cylinder wavefront is respectively arranged at least approximately perpendicular to the transverse axis direction (q).

Example 16

The method for robust one-shot interferometry according to one of examples 12 to 15 and example 3, wherein
in the section including the transverse axis direction (q), the Fourier plane of the object-imaging objective is at least approximately imaged sharply onto the rasterized detector by optical means; and
in the section perpendicular thereto, which in the unfolded optical path is parallel to the longitudinal direction of the line source, the measurement plane of the object is imaged sharply onto the rasterized detector by optical means, so that astigmatic imaging occurs in the detection optical path.

Example 17

The method for robust one-shot interferometry according to one of examples 10 to 16, wherein
in the imaging process in an intermediate image plane, confocal discrimination at least for the object light is performed by means of optical means; and/or
in the imaging process in an intermediate image plane, low-pass filtering for the object light is performed by means of optical means.

Example 18

A method for robust one-shot interferometry, comprising:
providing an assembly for robust one-shot interferometry (e.g. an assembly according to one of examples 12 to 14), said assembly preferably comprising:
at least one point light source or a point light source matrix with a plurality of spots;
at least one rasterized detector with receiver elements for electromagnetic radiation,
a two-beam interferometer with reference and object arms, comprising the following components:
an end reflector arranged in the reference arm of the two-beam interferometer;

at least one light source objective following the light source, for at least approximately imaging same or the spots in a diffraction-limited way, at least one objective imaging the object, wherein:

the point light source or the spots of the point light source matrix are each formed to be so fine that for the following light source objective it is/they are at least approximately equal to or below the diffraction-limited lateral resolution thereof, wherein the lateral resolution is determined by the numerical aperture of this light source objective and by the employed wavelength of light or by the employed wavelengths of the finely formed light source or the finely formed point light source matrix, and wherein the method comprises:

illuminating object points of the object, wherein in the case of optically rough objects, the object points are illuminated with at least approximately diffraction-limited sharply focused image points of the point light source or the point light source matrix; and in the case of optically smooth objects, are illuminated with slightly defocused image points of the point light source or the point light source matrix;

performing geometrically-optically defocused imaging of the illuminated object points onto the detector after beam unification, wherein light from each object point illuminates a subregion with a plurality of detector elements of the rasterized detector, and performing, in the reference arm R, geometrically-optically defocused imaging of points of the point light source or the point light source matrix, wherein light from each luminous point of the point light source or the point light source matrix illuminates a subregion with a plurality of elements of the rasterized detector after beam unification; and wherein the subregion surfaces on the rasterized detector of mutually coherent beam bundles from the object arm and from the reference arm are at least approximately made to overlap;

forming at least one spatial interferogram of coherent radiation from the reference arm and from the object arm, wherein the interference area (in a lateral extension) is at least 30% of the maximum extension of the two subregion surfaces, wherein at the output of the two-beam interferometer, in the space behind the tube objective or an at least approximately focusing objective or an at least approximately focusing objective from the illuminating optical path, which is also used for detection, both image points from the point light source or the point light source matrix, which are imaged via the reference arm R, and image points of the point light source or the point light source matrix, which are imaged via the object arm, are formed in a way separated from each other at least in depth the minimum of the depth separation def_r-o has the amount:

half the main wavelength in the detected signal of the spatial interferogram divided by the square of the effectively used numerical aperture of the tube objective, or of the at least approximately focusing objective, or of the at least approximately focusing objective from the illumination optical path, which is also used for detection.

and the amount of the maximum of the depth separation amount def_r-o is equal to the focal length of the tube objective, or of the at least approximately focusing objective, or of the at least approximately focusing objective from the illumination optical path, which is also used for detection.

The lateral extension (of the interference area) represents the overlap area of the interfering partial bundles.

Sharply focused image points or spots specifically are image points or spots that are (at least approximately) within the image-side wave-optical depth of field t'w (or depth of focus) for at least approximately diffraction-limited imaging of the image points, which is taken as a basis here. Slightly defocused image points or spots specifically are image points or spots that are e.g. within 100 times, preferably within 20 times the images-side wave-optical depth of field t'w (or depth of focus) for at least approximately diffraction-limited imaging of the image points. Typically, they are within 10 times of the image-side wave-optical depth of field t'w.

The image-side wave-optical depth of field t'w is defined by the quotient of wavelength and product of the associated refractive index and the square of the numerical aperture. The refractive index in air is assumed to be 1.

Example 19

The method for robust one-shot interferometry according to example 18, wherein the depth separation of foci of light from the reference arm and from the object arm in the detection optical path, in the case of an at least approximately equal optical path length in the two arms of the two-beam interferometer, is either provided in a predetermined way by using slightly different travel paths in differently optically dense media in the reference and object arms of the two-beam interferometer, or is provided in a predetermined way by forming slightly defocused spots in the reference arm on the end reflector.

Example 20

The method for robust one-shot interferometry according to example 18 or 19, wherein prior to detection, beam shaping is performed with elements of positive or negative refractive power of an array having focal planes thereof at least approximately in a common plane, and these focal planes coincide with the detection plane of the rasterized detector or are made optically conjugated thereto by means of an optical transfer stage.

Example 21

The method for robust one-shot interferometry according to examples 18 to 20, wherein the ring ordinal number is determined from the spherical component in the spatial interferogram.

TABLE I

Reference numeral list with explanations

| Reference numeral | Description |
|---|---|
| 1 | fine line source in NIR with longitudinal direction in y direction, preferably spectrally broadband, in transverse direction q with width below the diffraction-limited lateral resolution of the respective following optical system |
| 101 | pulsed line source in NIR, preferably spectrally broadband, in transverse direction q with width below the diffraction-limited lateral resolution of the respective following optical system |
| 102 | fine point light source, in transverse direction q with width below the diffraction-limited lateral resolution of the respective following optical system |
| 103 | fine line source formed by means of frequency comb light source, preferably a frequency comb laser (FCL), spectrally broadband fine line source, preferably spectrally broadband pulsed fine line source, preferably spectrally broadband |
| 104 | spatial light modulator, DMD, digital micro mirror device, generates light patterns at or below the lateral resolution of the following optical system for imaging same in the object space |
| 105 | spatial light modulator, transmissive or reflective LCD, generates light patterns at or below the lateral resolution of the following optical system for imaging same in the object space |
| 187 | light source with two pinhole chains rotated 90° with respect to each other, fed by a pulsed, spectrally broadband light source |
| 188 | fine matrix light source with fine ligth spots, one spot at the end of a single-mode fiber each. The fiber ends are arranged in a matrix structure. The light is coupled into the fibers by comparably spectrally broadband fiber-coupled super luminescent diodes. The resulting effective light spot size is below the diffraction-limited resolution of the following optical system. |
| 189 | finely line light source with fine light spots, generated by means of spectrally broadband LEDs and pinholes. The spot size, here the pinhole size, is below the diffraction-limited resolution of the following optical system. |
| 190 | fine matrix light source with fine light spots, generated by means of spectrally broadband LED matrix and downstream pinholes. The spot size, here the pinhole size, is below the diffraction-limited resolution of the following optical system. |
| 191 | fine line light source formed with spatial computer-controlled light modulator. Allows the computer-controlled lateral displacement of one or more fine light slits, which are below the diffraction-limited resolution of the following optical system. |
| 192 | fine line light source, preferably spectrally broadband |
| 193 | pulsed fine line light source (pulse lengths in the millisecond range or in the one-digit microsecond range) comparably spectrally broadband and represented with a frequency comb laser (FCL) with the optical delay length Y |
| 194 | fine slit illuminated with single-mode laser radiation, in the transvers direction q with width below the diffraction-limited resolution of the respective following optical system |
| 195 | fine point light source chain, preferably spectrally broadband, in the transvers direction q with width below the diffraction-limited resolution of the respective following optical system |
| 196 | fine light slit in y direction, light preferably spectrally broadband, in the transvers direction q with width below the diffraction-limited resolution of the respective following optical system |
| 197 | line light source array (rasterized) with several fine, at least approximately parallel line spots, preferably spectrally broadband, in the transverse direction q with width of the line spots below the diffraction-limited resolution of the respective following optical system. The line light source array may also be formed to be electronically controllable by means of a spatial light modulator. |
| 198 | finely formed point light source, preferably spectrally broadband, with extension of the light spots below the diffraction-limited resolution of the respective following optical system |

TABLE I-continued

Reference numeral list with explanations

| Reference numeral | Description |
|---|---|
| 199 | finely formed (rasterized) point light source matrix, preferably spectrally broadband, with extension of the light spots below the diffraction-limited resolution of the respective following optical system |
| LS | fine light slit, with width below the diffraction-limited resolution of the respective following optical system |
| LSO' | image of the fine line slit in the object space |
| LSR' | image of the fine line slit in the reference space |
| LSR" | image of the fine line slit in the reference space after first reflection at the hollow roof edge reflector |
| 2 | collimator objective, light source objective |
| 21 | focusing light source objective |
| 23 | line-like array of micro collimator lenses |
| 24 | areal array of micro collimator lenses |
| 3 | beam splitter, generally |
| 31 | beam splitter layer in a Mirau interferometer, on a plate |
| 32 | beam splitter layer in a Mirau interferometer with compensation plate |
| 33 | plate in a beam splitter, carrying the beam splitter layer |
| 34 | compensation plate in a beam splitter |
| 35 | coupling-out beam splitter |
| 36 | coupling-out beam splitter |
| 361 | beam splitter layer |
| 37 | beam splitter cube |
| 38 | beam splitter layer for Michelson interferomete for interferometric reference system for position control of the highly dynamic linear drive for reference objective |
| 39 | beam splitter system with several individual beam splitters |
| 391 | beam splitter plate carrying several beam splitter layers |
| 4 | rotationally symmetric reference Schwarzchild objective in the hybrid retro reference end refractor in the reference arm |
| 401 | microlens array in line form in the reference are of a multi-channel Linnik interferometer |
| 402 | mircolens array in matrix form in the reference arm of a multi-channel Linnik interferometer |
| 407 | rotationally symmetric microlens in a microlens array in line form 401 in the reference arm R of a multi-channel Linnik interferometer |
| 408 | rotationally symmetric microlens in a microlens array in matrix form 402 in the reference arm R of a multi-channel Linnik interferometer |
| 41 | cylinder mirror objective in ZSHRRER (44), cylinder objective axis (CA) is perpendicular to the longitudinal direction lo of the line source 1 |
| 42 | rotationally symmetric reference objective in the reference end reflector, also arranged in 45, 46, 47, 471 |
| 421 | plane interferometer end mirror in the reference arm R of a Linnik interferometer |
| 422 | plane interferometer end mirror in the reference arm R of a Twyman Green interferometer |
| 423 | concave, rotationally symmetric end mirror in the reference arm of a hybrid Linnik interferometer |
| 424 | plane interferometer end mirror in the reference arm of a multi-channel Linnik interferometer |
| 43 | plane mirror in the cylinder objective (41) in the cylinder mirror hybrid retro reference end reflector (ZSHRRER) |
| 44 | cylinder mirror hybrid retro reference and reflector (ZSHRRER) A ZSHRRER also represents a (special) hybrid retro reflector, which is used as an end reflector in the reference arm and which creates a mirror-symmetric wavefront inversion. The ZSHRRER is slightly tilted about an axis parallel to the longitudinal direction (optical path of the interferometer unfolded) of the line source and perpendicular to the cylinder objective axis. |
| 441 | cylinder objective hybris retro reference end reflector (ZLHRRER) |
| 45 | hybrid retro reference end reflector (HRRER), generic term without specification |
| 46 | hybrid retro reference end reflector system with a hollow 90° roof edge reflector array (564) and a rotationally symmetric reference objective 42, 4 in the reference arm (R) |
| 460 | hybrid retro reference end reflector system with a 90° micro roof edge prism mirror end reflector array (565) and a rotationally symmetric reference objective 42, 4 in the reference arm (R) |

TABLE I-continued

Reference numeral list with explanations

| Reference numeral | Description |
|---|---|
| 461 | hybrid retro reference end reflector system with a hollow 90° roof edge reflector array (564) and a rotationally symmetric objective 61, 62, or 91 outside the reference arm R |
| 462 | hybrid retro reference end reflector system with a hollow 90° roof edge prism mirror reflector array (565) and a rotationally symmetric objective 61, 62, or 91 outside the reference arm (R) |
| 47 | full retro reference end reflector (VRRER) with a hollow triple reflector (567) and a rotationally symmetric reference objective 42 |
| 471 | full retro reference end reflector system (VRRERS) with a hollow triple reflector array (566) and a rotationally symmetric reference objective 42 |
| 480 | micro plane mirror in a full retro micro end reflector |
| 481 | full retro reference micro end reflector of the rotationally symmetric lens cat's eye type |
| 482 | full retro reference micro end reflector of the rotationally symmetric mirror cat's eye type |
| 483 | hybrid retro micro reference end reflector of the cylinder objective cat's eye type |
| 484 | hybrid retro micro reference end reflector of the cylinder mirror cat's eye type |
| 485 | rotationally symmetric micro objective in a full retro micro reference end reflector 481 |
| 486 | cylinder microlens in a hybrid retro micro reference end reflector 483 |
| 491 | micro end reflector array with full retro reference micro end reflectors of the rotationally symmetric lens cat's eye type |
| 492 | reference micro end reflector array with full retro micro end reflectors of the rotationally symmetric mirror cat's eye type |
| 493 | reference micro end reflector array with hybrid retro reference micro end reflectors of the cylinder objective cat's eye type |
| 494 | reference micro end reflector array with hybrid retro reference micro end reflectors of the cylinder mirror cat's eye type |
| 498 | full retro reference micro end reflector system |
| 499 | hybrid retro reference micro end reflector system The reference end reflector 45 and the reference end reflector arrays 481 to 484 and 491 to 494 are preferably formed with a fine computer-controllable lateral translator, which is preferably synchronized with the spatial light modulator 104, 105 for approaching defined measurement positions on the object (71, 72, 73, 74). This serves for fast lateral scanning of the measurement field by several measurements in the "clearances" in order to be able to obtain a quasi full surface 3D data set of the object (71, 72, 73, 74). |
| 5 | 90° hollow roof edge reflector, standing alone in the reference arm, very tight 90° tolerance, roof edge is parallel to the longitudinal direction lo of the line light source and perpendicular to the transverse direction q |
| 51 | deflecting mirror |
| 52 | deflecting mirror |
| 53 | deflecting mirror |
| 54 | deflecting mirror |
| 55 | deflecting mirror |
| 56 | 90° hollow roof edge end reflector in conjunction with a rotationally symmetric objective (62, 91) outside the interferometer 90°, forming a hybrid retro reference end reflector |
| 561 | $1^{st}$ hollow 90° roof edge end reflector in the reference arm in combination with a rotationally symmetric reference objective 42 in HRRER, rather little 90° tolerance, roof edge standing in y direction, roof edge is parallel to the longitudinal direction lo of the line light source and perpendicular to the transverse direction q |
| 562 | $2^{nd}$ hollow 90° roof edge end reflector in the reference arm in combination with a rotationally symmetric reference objective 42 in HRRER, roof edge arranged in x direction (lying), rather little 90° angle tolerance |

TABLE I-continued

Reference numeral list with explanations

| Reference numeral | Description |
|---|---|
| 564 | 90° hollow roof edge mirror micro end reflector array in combination with a rotationally symmetric reference objective 42 in the reference arm |
| 565 | 90° roof edge prism mirror micro end reflector array in combination with a rotationally symmetric reference objective 42 in the reference arm |
| 566 | hollow triple mirror micro end reflector array (Each triple micro end reflector is formed as a spatial corner.) |
| 567 | hollow triple mirror micro end reflector (spatial corner) |
| 568 | triple prism mirror micro end reflector array<br>All micro end reflector arrays 564 to 566 and 568 are preferably formed with a fine computer-controllable lateral translator, which is preferably synchronized with the spatial light modulator 104, 105. This serves for fast lateral scanning of the measurement field by several measurements in order to be able to obtain a full surface or quasi full surface 3D data set of the object 71 to 74. |
| 569 | compensation plate in the object arm<br>(Plate for at least approximate compensation of the thickness d of the optical medium for a 90° roof edge prism reflector array, 90° roof edge prism (58), or triple prism or for cat's eye lenses, also for a cat's eye lenses array) |
| 57 | 90° hollow light-weight roof edge end reflector in combination with a rotationally symmetric objective 42 in the RHRER, rather little 90 ° angle tolerance |
| 58 | 90° roof edge prism in the objective 42, 64, stationary, 90° angle tolerance of the 90° roof edge prism rather great |
| 581 | 90° roof edge prism in the objective 42, 64, rotated by 90°, stationary |
| 59 | 90° roof edge prism moved in z direction in the reference arm |
| 6 | rotationally symmetric Schwarzschild objective in the object arm O, the measuring beam path |
| 61 | rotationally symmetric objective assigned to the Michelson interferometer, used in double beam pass |
| 62 | rotationally symmetric objective at the interferometer output, used in single beam pass, detector objective, objective 62 images object in infinity |
| 63 | Schwarzschild measuring objective us part of a Mirau interferometer, rotationally symmetric |
| 64 | measuring objective as part of a Mirau interferometer, rotationally symmetric |
| 651 | microlens array in line form in the object arm of a multi-channel Linnik interferometer |
| 652 | microlens array in matrix form in the object arm of a multi-channel Linnik interferometer |
| 653 | microlens array in matrix form in a multi-channel Mirau interferometer |
| 654 | rotationally symmetric microlens in a microlens array in matrix form in a multi-channel Mirau interferometer |
| 657 | rotationally symmetric microlens in a microlens array in line form in the object arm of a multi-channel Linnik interferometer |
| 658 | rotationally symmetric microlens in a microlens array in matrix form in the object arm of a multi-channel Linnik interferometer |
| 66 | measuring objective, rotationally symmetric, but otherwise unspecified, here usually in a Linnik interferometer |
| 67 | Mirau objective interferometer with measuring objective 64, rotationally symmetric |
| 68 | Mirau objective interferometer with rotationally symmetric Schwarzschild objective 63 |
| 681 | plane reference mirror in a Mirau objective interferometer |
| 69 | guided sensor array consisting of a plurality of Mirau systems-but at least two-formed with 90° hollow roof edge reflector 56 |
| 71 | human skin |
| 72 | living organ |
| 73 | rough metal surface |
| 74 | optically smooth metal surface |

TABLE I-continued

Reference numeral list with explanations

| Reference numeral | Description |
| --- | --- |
| 75 | polished aspherical surface, optically smooth |
| 8 | astigmatic imaging system |
| 81 | astigmatic imaging system with two rotationally symmetric lenses in 4f arrangement, one thereof the tube objective 9, with downstream cylinder objective 12, the focal plane thereof coinciding with the last focal plane of the 4f arrangement where the rasterized detector is located |
| 82 | astigmatic detector objective consisting of a rotationally symmetric objective 11 and a cylinder objective 12 |
| 821 | astigmatic detector objective for second channel, consisting of a rotationally symmetric objective 11 and a cylinder objective 12 |
| 83 | Schwarzschild cylinder objective for detector 13 |
| 84 | microlens array operates as an optical Fourier processor |
| 841 | microlens in a microlens array |
| 842 | Microlens |
| 85 | small mirror objective as Fourier transform component |
| 86 | mirror objective array as Fourier transform array |
| 87 | 4f transfer stage |
| 88 | red-transmission filter |
| 89 | micro red-barrier filter array |
| 891 | micro red-barrier filter |
| 9 | rotationally symmetric tube objective |
| 901 | tube microlens array in line form in the detection optical path of a multi-channel Linnik interferometer |
| 902 | tube microlens array in matrix form in the detection optical path of a multi-channel Linnik interferometer |
| 903 | tube microlens array in matrix form in the detection optical path of a multi-channel Mirau interferometer |
| 907 | rotationally symmetric tube microlens in a tube microlens array in line form |
| 908 | rotationally symmetric tube microlens in a tube microlens array in matrix form |
| 95 | fine slit diaphragm for spatial filtering of light coming from the reference arm |
| 96 | fine slit diaphragm for spatial filtering of light coming from the object arm |
| 961 | fine slit diaphragm also serves for suppressing background light from the depth of measured skin |
| 97 | fine slit diaphragm array for spatial filtering of light from the object |
| 98 | plane deflecting mirror |
| 99 | plane deflecting mirror with fine slit diaphragm |
| 11 | rotationally symmetric objective |
| 111 | rotationally symmetric microlens in a microlens array |
| 115 | rotationally symmetric objective |
| 116 | highly dynamic linear drive for Mirau objective |
| 117 | highly dynamic linear drive for 90° roof edge prism, preferably a piezo actuator |
| 118 | highly dynamic linear drive for reference objective |
| 119 | highly dynamic linear drive for measuring objective |
| 12 | cylinder objective |
| 121 | cylindrical microlens in a cylinder microlens array |
| 122 | single-mode laser for interferometric reference measuring system as sensor for position control of the drive for the reference objective 104 |
| 128 | astigmatic imaging system for reference measuring system with quadruple photodiode block |
| 129 | mirror cylinder objective |
| 13 | rasterized detector for electromagnetic radiation |
| 132 | a second rasterized detector for electromagnetic radiation, chip of a digital camera |
| 133 | observation camera |
| A | luminous point on the light source or the luminous light slit |
| A_r' | image of a luminous point in the reference arm R |
| A_o' | image of a luminous point in the object arm O |
| A_r" | image of a luminous point in the detection optical path, coming from the reference arm R |
| A_o" | image of a luminous point in the detection optical path, coming from the object arm O The images A_o" and A_r" of a luminous point are optically conjugated to each other. |

TABLE I-continued

Reference numeral list with explanations

| Reference numeral | Description |
|---|---|
| alpha_y_source | aperture angle that is at least approximately still detected by the diffraction-limited light source imagining system |
| alpha_0 | aperture angle in the angular spectrum of the illumination, in which the optical path difference on the rasterized detector 13 becomes zero. |
| ASL | Airy disc symmetry line |
| aTS | adaptive trigger threshold, corresponds to a reference point in a short-coherence interferogram with chirping in the surrounding of the zero-order stripe, which can still be clearly identified |
| BER | outer focal plane (focal plane facing away from the beam splitter) of the reference objective in the reference arm R |
| b_spot | width of the line light source |
| b_spot_g' | geometrically-optically imaged width of the line light source in the object space |
| b_spot | line spot width of the luminous line spot |
| b_spot_g' | geometrically-optically imaged width of the luminous line spot b spot of the light source in the object space |
| 2 bl_Airy | full width up to the first two zeros in the Airy pattern in the object space, also referred to as the full Airy width here |
| CA | cylinder axis in a cylindrical objective |
| d_r | geometric thickness of the beam splitter plate in the reference arm R in a Mirau interferometer |
| d_o | geometric thickness of the beam splitter plate in the object arm O in a Mirau interferometer |
| DK | roof edge of a roof edge reflector |
| DKL | roof edge line of the hybrid retro reference end reflector (in the reference arm) with centrosymmetric wavefront inversion (centrosymmetric) |
| HRRER | hybrid retro reference end reflector (in the reference arm) with centrosymmetric wavefront inversion |
| 2 delta_beta_tilt | tilt angle of the interfering wavefronts in the reference arm after they have passed the hybrid retro reference end reflector with centrosymmetric wavefront inversion, tilt axis is the y axis |
| 2 delta_beta'_tilt | tilt angle of the interfering wavefronts during the detection, preferably also formed as cylinder waves and with the tilt angle between the focus lines of the cylinder waves, tilt axis is the y axis |
| delta_beta_HRRER | tilt of the hybrid retro reference end reflector (in the reference arm) is equal to beta_tilt, tilt axis is the y axis |
| delta_beta_DK | tilt of the roof edge about y axis |
| delta_d | geometric thickness difference of the two beam splitter plates in a Mirau interferometer |
| delta_q | transverse offset of the hybrid retro reference end reflector |
| 2 delta_q = s | lateral shear between an object wavefront and a reference wavefront in the reference arm after they have passed the hybrid retro reference end reflector |
| 2 delta_q_strich = s' | lateral shear considering the magnification of the optical system at the output of the two-beam interferometer between an object point (A_o'') and an optically conjugated reference point (A_r'') as the necessary prerequisite for a tilt of object and reference wavefronts with respect to each other in the plane of rasterized detector 13 |
| d_H | diameter of the beam bundle on the hybrid retro reference end reflector in y direction |
| DK_hollow | roof edge in hollow 90° roof edge mirror reflector |
| Dm_spot | diameter of a luminous point spot of the light source |
| Dm_spot_g' | diameter of the geometrical-optical image of a luminous point spot in the object space, which is imaged geometrically-optically |
| DOV | wave-optical depth of field of the sensor (depth of field)_ |
| def_r-o | current, object point-dependent (variable) depth separation (z direction) of a reference image point and an object image point in the detection optical path behind the objective (62, 91, 9). This represents a parameter determined both by construction and adjustment as well as by the current object point position. def_r-o1 describes the depth separation of the image points in the detection optical path, which are formed from the luminous point A1 of the point light source 199. |

TABLE I-continued

Reference numeral list with explanations

| Reference numeral | Description |
|---|---|
| def_r-o_strich | current, object point-dependent (variable) depth separation (z direction) of a reference image point and an object image point in the detection optical path in a further imaging situation behind the objective (9, 62, 91, optionally also 2 in the backward optical path). def_r-o_strich represents a variable parameter determined both by construction and adjustment as well as by the respective current object point position. |
| Def | fixed depth separation (z direction) of the foci in the interferometer as images of the point light source, based on an unfolded interferometer optical path. Def represents a fixed parameter in the optical system, which is determined by construction and adjustment. |
| Def_strich | fixed depth separation (z direction) of the foci in the detection optical path, Def_strich may correspond to the focal length of the microlens 841. |
| Def_strich_2 | fixed depth separation (z direction) of the foci in the detection optical path after a further imaging, usually behind the tube objective 9 |
| E_R | plane where the reflection of the reference waves is localized |
| EFL | plane E_xy in the selected coordinate system fixedly assigned to the line light source |
| E_xz | plane E_xz in the selected coordinate system fixedly assigned to the line light source |
| F, F', F" | focal points |
| F, also F_o and F_r | focal points in the object space O and in the reference space R, respectively (these focal points in the object space are always without a prime, whereas the Fourier plane is given a prime for "F", i.e. "F'") |
| F' also F_o' and F_r' | focal points in the Fourier plane of the object space O and in the reference space R, respectively |
| F_11' | image focal point of the cylinder objective 11 |
| F_MLA | object-side focal plane of the microlens array |
| F_MLA' | image-side focal plane of the microlens array |
| FCL | frequency comb laser |
| FEO | Fourier plane in object space O |
| FER | Fourier plane in the reference space R |
| HRRER (45, 46) | hybrid retro reference end reflector By definition, a hybrid retro reference end reflector generates a reference wavefront always tilted toward the object wavefront. This transverse offset is generated by means of a roof edge reflector in the focal plane of the objective (4, 42). |
| h_spot' | height/length of the image of the luminous line spot in the object space |
| KKI | short-coherence interferogram |
| Lambda | wavelength of the detected electromagnetic radiation |
| Lambda_S | main wavelength of the detected electromagnetic radiation |
| lb | lateral region in the depth of field T of the sensor when the surface is ideally smooth |
| LKI | long-coherence interferogram, is formed when the light source has a great coherence length |
| l_lat | lateral region in which a smooth object surface of a tilted sensor is in the wave-optical depth of field T |
| L-opt_P | optical path difference in the prism for single light penetration |
| L-opt_T | optical path difference in the splitter plate for single light penetration |
| LS | fine light slit |
| LS_r' | image of the fine light slit in the reference arm |
| LS_o' | image of the fine slit in the object arm |
| MEO | measurement plane in the object space |
| n | integer |
| n* | refractive index of an optical medium |
| 2q1_Airy | full diameter up to the first two zeros in the Airy pattern, also referred to as the full Airy diameter here, in the object space |
| OPD | optical path difference |
| OPD-FCL_c | optical path difference compensated by FCL, region of high spatial coherence |

TABLE I-continued

Reference numeral list with explanations

| Reference numeral | Description |
|---|---|
| RL | line of the hybrid retro reference end reflector. It defines the plane E_R, where the reflection of at least one reference wave is located in a model-like way |
| | RL is a parallel line to a cylinder axis CA in a cat's eye reflector, where the focusing of cylinder waves, generated from a plane input wave, is localized. |
| | In the case of a 90° roof edge mirror end reflector, RL coincides with the roof edge line DKL. |
| RS_hin | outgoing reference beam |
| OWF | object wavefront |
| RWF | reference wavefront |
| RS_rück | returning reference beam |
| SH | signal deviation between maximum value in the zero stripe order and the smallest of the two maxima in the first-order stripe, the adaptive trigger threshold aTS |
| v | optical image offset by thickness d of the optical medium (glass, plastics, liquid) and refractive index n of same with respect to the air way |
| VRRERA | full retro reference end reflector array |
| | A full retro reference end reflector array with triple reflectors always generates a tilted reference wavefront, i.e. there must always be at least one associated objective (42) |
| Y | optical delay length in FCL |
| y | direction of longitudinal extension of the (first) line source |
| y_tilt | tilt axis of the hybrid retro reference end reflector with minor-symmetric wavefront inversion for the tilt delta_beta_y of same |
| ZBE | intermediate image plane |
| z_Tsep | depth separation of the coherent foci of object arm O and reference arm R |

We claim:

1. An assembly for robust one-shot interferometry, comprising:
   a light source;
   a rasterized detector with receiver elements for electromagnetic radiation; and
   a two-beam interferometer having a reference arm and an object arm including the following components:
     a light source objective following or downstream of the light source, for imaging same in an at least approximately diffraction-limited way, wherein the light source is at least a line light source formed to be narrow in at least a transverse axis direction or a line light source array comprising a plurality of line sources each formed to be narrow in a transverse axis direction, the plurality of line sources being at least approximately parallel to each other,
     wherein a width in the transverse axis direction of the line light source or each of the plurality of line sources, of the line light source array, is at least approximately equal to or below a diffraction-limited lateral resolution of the light source objective in at least the transverse axis direction, and
     wherein the lateral resolution is determined by a numerical aperture of the light source objective and by an employed wavelength of light or by employed wavelengths of light of the line light source or the line light source array; and
     a first objective for imaging an object, wherein in the reference arm of the two-beam interferometer, there is arranged an end reflector formed as a retro end reflector, which is designed to generate one or more tilted reference wavefronts and/or there is arranged at least a first lens for defocusing reference light,
   wherein the line light source is imaged onto the object in a diffraction-limited way in at least one dimension by means of the first objective,
   wherein the end reflector is a hybrid retro reference end reflector that reflects an incident light beam parallel to itself independent of its angle of incidence only in one single plane of incidence, and the hybrid retro reference end reflector has at least one 90° roof edge end reflector,
   wherein a roof edge of the 90° roof edge end reflector is positioned at least approximately in a focal plane of a reference objective arranged in the reference arm or of a second objective arranged outside the reference arm, and
   wherein the roof edge of the 90° roof edge end reflector is arranged at least approximately perpendicular to the transverse axis direction if no focusing reference objective is arranged in the reference arm, or is arranged at least approximately parallel to the transverse axis direction if a focusing reference objective is arranged in the reference arm,
   wherein there is a transverse offset of the roof edge at least approximately parallel to the direction of the transverse axis direction either in the focal plane of the reference objective assigned to the hybrid retro reference end reflector or in the focal plane of a third objective assigned to the reference arm and to the object arm,
   wherein the transverse offset is at most equal to one-tenth of the focal length of the second and/or third objective, and at least equal to or greater than an objective-based Airy disk radius for a main wavelength in a detected spatial interferogram, wherein the main wavelength corresponds to at least one of the employed wavelength of light or employed wavelengths of light of the line light source, and wherein the two-beam interferometer is designed to generate at least a pair of mutually tilted and/or differently curved reference and object wavefronts and to make the pair of wavefronts interfere.

2. An assembly for robust one-shot interferometry, comprising:

a light source;

a rasterized detector with receiver elements for electromagnetic radiation; and a two-beam interferometer having a reference arm and an object arm including the following components:

a light source objective following or downstream of the light source, for imaging same in an at least approximately diffraction-limited way, wherein the light source is at least a line light source formed to be narrow in at least a transverse axis direction or a line light source array comprising a plurality of line sources each formed to be narrow in a transverse axis direction, the plurality of line sources being at least approximately parallel to each other, wherein a width in the transverse axis direction of the line light source or each of the plurality of line sources, of the line light source array, is at least approximately equal to or below a diffraction-limited lateral resolution of the light source objective in at least the transverse axis direction, and wherein the lateral resolution is determined by a numerical aperture of the light source objective and by an employed wavelength of light or by employed wavelengths of light of the line light source or the line light source array; and a first objective for imaging an object, wherein in the reference arm of the two-beam interferometer, there is arranged an end reflector formed as a retro end reflector, which is designed to generate one or more tilted reference wavefronts and/or there is arranged at least a first lens for defocusing reference light, wherein the line light source is imaged onto the object in a diffraction-limited way in at least one dimension by means of the first objective, wherein the end reflector is a hybrid retro reference end reflector that reflects an incident light beam parallel to itself independent of its angle of incidence only in one single plane of incidence, the hybrid retro reference end reflector comprising either a cylinder optics hybrid retro reference end reflector with a cylinder objective having a cylinder axis and a plane mirror in a focal plane of the cylinder objective, wherein the cylinder axis is respectively perpendicular to the transverse axis direction, or a 90° roof edge reflector, wherein there is a tilt of the hybrid retro reference end reflector about a tilt axis that is at least approximately perpendicular to the transverse axis direction and to a direction of light propagation, in each case based on an unfolded optical path of the two-beam interferometer, and a tilt angle is at most equal to or smaller than 6 degrees and at least equal to or greater than half a main wavelength in a detected spatial interferogram, based on an illuminated pupil diameter of the cylinder objective at an interferometer output, wherein the main wavelength corresponds to at least one of: the employed wavelength of light or employed wavelengths of light of the line light source, and wherein the two-beam interferometer is designed to generate at least a pair of mutually tilted and/or differently curved reference and object wavefronts and to make the pair of wavefronts interfere.

3. An assembly for robust one-shot interferometry, comprising:

a light source;

a rasterized detector with receiver elements for electromagnetic radiation; and a two-beam interferometer having a reference arm and an object arm including the following components:

a light source objective following or downstream of the light source, for imaging same in an at least approximately diffraction-limited way, wherein the light source is at least a line light source formed to be narrow in at least a transverse axis direction or a line light source array comprising a plurality of line sources each formed to be narrow in a transverse axis direction, the plurality of line sources being at least approximately parallel to each other, wherein a width in the transverse axis direction of the line light source or each of the plurality of line sources, of the line light source array, is at least approximately equal to or below a diffraction-limited lateral resolution of the light source objective in at least the transverse axis direction, and wherein the lateral resolution is determined by a numerical aperture of the light source objective and by an employed wavelength of light or by employed wavelengths of light of the line light source or the line light source array; and a first objective for imaging an object, wherein in the reference arm of the two-beam interferometer, there is arranged an end reflector formed as a retro end reflector, which is designed to generate one or more tilted reference wavefronts and/or there is arranged at least a first lens for defocusing reference light, wherein the line light source is imaged onto the object in a diffraction-limited way in at least one dimension by means of the first objective, wherein the end reflector is a hybrid retro reference end reflector that reflects an incident light beam parallel to itself independent of its angle of incidence only in one single plane of incidence, the hybrid retro reference end reflector comprising either a reference end reflector array with a plurality of roof edge mirror or roof edge prism hybrid retro, or as a reference end reflector array with a plurality of cylinder lens cat's eye or cylinder mirror cat's eye hybrid retro reference end reflectors, wherein there is a transverse offset of the cylinder cat's eye hybrid retro reference end reflectors or of the roof edge hybrid retro reference end reflectors in the reference end reflector array either in a focal plane of a reference objective arranged in the reference arm and assigned to the hybrid retro reference end reflector, or in a focal plane of a second objective arranged outside the reference arm and assigned to the reference arm and to the object arm, wherein the transverse offset is at least approximately parallel to the direction of the transverse axis direction and at most equal to one-tenth of a focal length of the reference objective or of the second objective arranged outside the reference arm, and at least equal to or greater than an objective-based Airy disk radius for a main wavelength in a detected spatial interferogram, wherein the main wavelength corresponds to at least one of: the employed wavelength of light or employed wavelengths of light of the line light source, and wherein the two-beam interferometer is designed to generate at least a pair of mutually tilted and/or differently curved reference and object wavefronts and to make the pair of wavefronts interfere.

* * * * *